(12) United States Patent
Shepard

(10) Patent No.: US 7,419,968 B1
(45) Date of Patent: *Sep. 2, 2008

(54) METHODS FOR TREATING THERAPY-RESISTANT TUMORS

(75) Inventor: H. Michael Shepard, Encinitas, CA (US)

(73) Assignee: Celmed Oncology (USA), Inc., Montreal, Quebec (CA)

( * ) Notice: Subject to any disclaimer, the term of this patent is extended or adjusted under 35 U.S.C. 154(b) by 497 days.

This patent is subject to a terminal disclaimer.

(21) Appl. No.: 10/048,033

(22) PCT Filed: Jul. 21, 2000

(86) PCT No.: PCT/US00/20007

§ 371 (c)(1),
(2), (4) Date: Nov. 27, 2002

(87) PCT Pub. No.: WO01/07088

PCT Pub. Date: Feb. 1, 2001

Related U.S. Application Data

(60) Provisional application No. 60/153,855, filed on Sep. 14, 1999, provisional application No. 60/145,364, filed on Jul. 22, 1999.

(51) Int. Cl.
*A61K 31/70* (2006.01)

(52) U.S. Cl. .......................................... 514/51; 514/50

(58) Field of Classification Search ................... 514/50, 514/51
See application file for complete search history.

(56) References Cited

U.S. PATENT DOCUMENTS

| | | | |
|---|---|---|---|
| 3,852,266 A * | 12/1974 | Kiyanagi et al. ......... | 536/28.55 |
| 4,247,544 A | 1/1981 | Bergstrom et al. | |
| 4,267,171 A | 5/1981 | Bergstrom et al. | |
| 4,542,210 A | 9/1985 | Sakata et al. | |
| 4,668,777 A | 5/1987 | Caruthers et al. | |
| 4,816,570 A | 3/1989 | Farquhar | |
| 4,948,882 A | 8/1990 | Ruth | |
| 4,963,263 A | 10/1990 | Kauvar | |
| 4,963,533 A | 10/1990 | de Clercq et al. | |
| 4,975,278 A | 12/1990 | Senter et al. | |
| 5,070,082 A * | 12/1991 | Murdock et al. ............. | 514/105 |
| 5,077,282 A * | 12/1991 | Murdock et al. .............. | 514/80 |
| 5,077,283 A * | 12/1991 | Murdock et al. .............. | 514/94 |
| 5,085,983 A | 2/1992 | Scanlon | |
| 5,116,822 A | 5/1992 | De Clercq et al. | |
| 5,116,827 A * | 5/1992 | Murdock et al. .............. | 514/82 |
| 5,133,866 A | 7/1992 | Kauvar | |
| 5,137,724 A | 8/1992 | Balzarini et al. | |
| 5,212,161 A * | 5/1993 | Moriniere et al. ............. | 514/50 |
| 5,212,291 A * | 5/1993 | Murdock et al. ............. | 536/6.4 |
| 5,217,869 A | 6/1993 | Kauvar | |
| 5,233,031 A | 8/1993 | Borch et al. | |
| 5,264,618 A | 11/1993 | Felgner et al. | |
| 5,274,162 A | 12/1993 | Glazier | |
| 5,300,425 A | 4/1994 | Kauvar | |
| 5,338,659 A | 8/1994 | Kauvar et al. | |
| 5,430,148 A | 7/1995 | Webber et al. | |
| 5,433,955 A | 7/1995 | Bredehorst et al. | |
| 5,457,187 A * | 10/1995 | Gmeiner et al. ............ | 536/25.5 |
| 5,459,127 A | 10/1995 | Felgner et al. | |
| 5,502,037 A | 3/1996 | Kondratyev | |
| 5,516,631 A | 5/1996 | Frisch | |
| 5,521,161 A | 5/1996 | Malley et al. | |
| 5,527,900 A | 6/1996 | Balzarini et al. | |
| 5,556,942 A | 9/1996 | Kauvar et al. | |
| 5,596,018 A | 1/1997 | Baba et al. | |
| 5,616,564 A * | 4/1997 | Rapaport et al. .............. | 514/44 |
| 5,627,165 A | 5/1997 | Glazier | |
| 5,643,893 A | 7/1997 | Benson et al. | |
| 5,645,988 A | 7/1997 | Vande Woude et al. | |
| 5,663,321 A | 9/1997 | Gmeiner et al. | |
| 5,733,896 A | 3/1998 | Holy et al. | |
| 5,798,340 A | 8/1998 | Bischofberger et al. | |
| 5,968,910 A | 10/1999 | Balzarini | |
| 5,981,507 A | 11/1999 | Josephson et al. | |
| 6,057,305 A | 5/2000 | Holy et al. | |
| 6,245,750 B1 * | 6/2001 | Shepard ........................ | 514/51 |
| 6,339,151 B1 * | 1/2002 | Shepard et al. ............ | 536/26.8 |

(Continued)

FOREIGN PATENT DOCUMENTS

DE 32 29 169 A1 2/1984

(Continued)

OTHER PUBLICATIONS

Firestone et al., "A Comparison of the Effects of Antitumor Agents Upon Normal Human Epidermal Keratinocytes and Human Squamous Cell Carcinoma," Journal of Investigate Dermatology, 94(5), 657-661 (May 1990).*

Dagle et al., "Targeted Degradation of mRNA in *Xenopus oocytes* and Embryos Directed by Modified Oligonucleotides: Studies of An2 and Cyclin in Embryogenesis," Nucleic Acids Research, 18(16), 4751-4757 (Aug. 25, 1990).*

Hakimelahi et al., "Design, Synthesis, and Structure-Activity Relationship of Novel Dinucleotide Analogs as Agents Against Herpes and Human Immunodeficiency Viruses," Journal of Medicinal Chemistry, 38(23), 4648-4659 (Nov. 10, 1995).*

Naesens et al., "Anti-HIV Activity and Metaboli . . . ," Poster Session 1, The Tenth International Conference on Antiviral Research, Hotel Nikko, Atlanta, GA, Apr. 6-11, 1997; published in Antiviral Research, 34(2), p. A54 (Abstract 40), Apr. 1997).*

(Continued)

*Primary Examiner*—Shaojia Anna Jiang
*Assistant Examiner*—Lawrence E. Crane
(74) *Attorney, Agent, or Firm*—Foley & Lardner LLP

(57) ABSTRACT

This invention provides methods for using novel substituted pyrimidine compounds, derivatives and analogs thereof to treat diseases such as cancer. Examples of compounds and derivatives for use in the methods are (E)-5-(2-bromovinyl)-2'-deoxy-5'-uridyl phenyl L-alaninylphosphoramidate and (E)-5-(2-bromovinyl)-2'-deoxy-5'-uridyl phenyl L-alaninyl monophosphate.

4 Claims, 15 Drawing Sheets

U.S. PATENT DOCUMENTS

| | | | |
|---|---|---|---|
| 6,495,553 B1 * | 12/2002 | Shepard | 514/256 |
| 6,589,941 B1 | 7/2003 | Fahrig et al. | |
| 6,599,499 B1 | 7/2003 | Rosen et al. | |
| 6,677,314 B2 | 1/2004 | Klecker et al. | |
| 6,677,315 B2 | 1/2004 | Klecker et al. | |
| 6,682,715 B2 | 1/2004 | Klecker et al. | |
| 6,683,045 B2 | 1/2004 | Klecker et al. | |
| 6,683,061 B1 * | 1/2004 | Shepard et al. | 514/50 |
| 6,703,374 B1 | 3/2004 | Klecker et al. | |
| 6,753,309 B2 | 6/2004 | Klecker et al. | |
| 2001/0034440 A1 * | 10/2001 | Shepard et al. | 536/26.1 |
| 2002/0022001 A1 | 2/2002 | Klecker et al. | |
| 2002/0034473 A1 | 3/2002 | Klecker et al. | |
| 2002/0119094 A1 | 8/2002 | Klecker et al. | |
| 2002/0147175 A1 * | 10/2002 | Shepard et al. | 514/49 |
| 2002/0151519 A1 * | 10/2002 | Shepard | 514/50 |
| 2002/0165199 A1 | 11/2002 | Klecker et al. | |
| 2003/0049201 A1 | 3/2003 | Klecker et al. | |
| 2003/0095921 A1 | 5/2003 | Klecker et al. | |

FOREIGN PATENT DOCUMENTS

| | | |
|---|---|---|
| EP | 0095294 | 11/1983 |
| EP | 0283065 | 9/1988 |
| EP | 0 311 107 A2 | 4/1989 |
| EP | 0 311 108 A2 | 4/1989 |
| EP | 0 316 592 | 5/1989 |
| GB | 982776 * | 2/1965 |
| RO | 88451 | 1/1986 |
| WO | WO 89/05817 | 6/1989 |
| WO | WO 90/03978 | 4/1990 |
| WO | WO 91/17424 | 11/1991 |
| WO | WO 92/19767 | 11/1992 |
| WO | WO 92/20344 | 11/1992 |
| WO | WO 93/06120 | 4/1993 |
| WO | WO 94/03467 | 2/1994 |
| WO | WO94/22483 A2 * | 10/1994 |
| WO | WO 94/22483 A2 * | 10/1994 |
| WO | WO 95/01806 | 1/1995 |
| WO | WO95/08556 A1 * | 3/1995 |
| WO | WO 95/08556 A1 * | 3/1995 |
| WO | WO 95/09865 | 4/1995 |
| WO | WO 95/12678 | 5/1995 |
| WO | WO 96/03151 A2 * | 2/1996 |
| WO | WO96/03151 A2 * | 2/1996 |
| WO | WO 96/07431 A1 * | 3/1996 |
| WO | WO96/07431 A1 * | 3/1996 |
| WO | WO 96/10300 A1 * | 4/1996 |
| WO | WO96/10300 A1 * | 4/1996 |
| WO | WO 96/23506 | 8/1996 |
| WO | WO 96/29336 | 9/1996 |
| WO | WO 96/33168 | 10/1996 |
| WO | WO 96/40088 | 12/1996 |
| WO | WO96/40708 A1 * | 12/1996 |
| WO | WO 96/40708 A1 * | 12/1996 |
| WO | WO 96/40739 | 12/1996 |
| WO | WO 97/25342 | 7/1997 |
| WO | WO97/28179 A1 * | 8/1997 |
| WO | WO 97/28179 A1 * | 8/1997 |
| WO | WO 97/49717 | 12/1997 |
| WO | WO 98/49177 | 11/1998 |
| WO | WO 99/06072 | 2/1999 |
| WO | WO 99/08110 | 2/1999 |
| WO | WO 99/20741 A1 * | 4/1999 |
| WO | WO99/20741 A1 * | 4/1999 |
| WO | WO 99/23104 | 5/1999 |
| WO | WO 99/37753 | 7/1999 |
| WO | WO 00/18775 | 4/2000 |
| WO | WO 00/33888 | 6/2000 |
| WO | WO 01/07088 | 2/2001 |
| WO | WO 01/07454 A1 * | 2/2001 |
| WO | WO01/07454 A1 * | 2/2001 |
| WO | WO 01/83501 | 11/2001 |
| WO | WO 01/85749 | 11/2001 |

OTHER PUBLICATIONS

Evrard et al., "An in vitro Nucleoside Analog Screening Method for Cancer Gene Therapy," Cell Biology and Toxicology, 12, 345-350 (1996).*

Berkow et al. (eds.), The Merck Manual of Diagnosis and Therapy, 16th Ed., Merck & Co., Rahway, NJ, May 1992, only p. 1278 supplied.*

Morrison & Boyd (eds.), Organic Chemistry, Allyn & Bacon, Inc., Boston, MA, 1973, only pp. 1170-1180 supplied.*

L. B. Townsend (ed.), Chemistry of Nucleosides and Nucleotides, vol. 3, Plenum Press, New York, NY, 1974, only Table of Contents, Bibliography pp. 529-535, and Index pp. 537-552 supplied.*

The American Heritage College Dictionary, Third Edition, Houghton Mifflin Co., New York, NY, 1997, only p. 668 supplied.*

Smith et al., "Second Passage Human Breast Cancer Cells," Cancer Research, 50(10), 2943-2948 (May, 1990).*

O'Neil et al. (eds.), The Merck Index, 13th Edition, Merck & Co., Whitehouse Station, NJ, 2001, only p. 1452 supplied, see Entry No. 8191 which identifies "Tomudex."*

Naesens et al., "Anti-HIV Activity and Metabolism of Phosphoramidate Derivatives of D4T-MP with Variations in the Amino Acid Moiety," Poster Session 1, The Tenth International Conference on Antiviral Research, Hotel Nikko, Atlanta, GA, Apr. 6-11, 1997; Published in *Antiviral Research*, 34(2), p. A54 (Abstract 40), (Apr. 1997).*

Berkow et al. (eds.) *The Merck Manual of Diagnosis and Therapy, 16th Ed.*, Merck & Co., Rahway, NJ, May 1992, only p. 1278 supplied.*

Morrison & Boyd (eds.), *Organic Chemistry*, Allyn & Bacon, Inc., Boston, MA, 1973, only pp. 1170-1180 supplied.*

L. B. Townsend (ed.), *Chemistry of Nucleosides and Nucleotides*, vol. 3, Plenum Press, New York, NY, 1974, only Table of Contents, Bibliography pp. 529-535, and Index pp. 537-552 supplied.*

*The American Heritage College Dictionary, Third Edition*, Houghton Mifflin Co., New York, NY, 1997, only p. 668 supplied.*

Smith et al., "Second Passage Human Breast Cancer Cells," *Cancer Research*, 50(10), 2943-2948 (May 1990).*

O'Neil et al. (eds.), *The Merck Index, 13th Edition*, Merck & Co., Whitehouse Station, NJ, 2001, only p. 1452 supplied, see Entry No. 8191 which identifies "Tomudex."*

Abraham et al. "Synthesis and biological activity of aromatic amino acid phosphoramidates of 5-fluoro-2'-deoxyuridine and 1-β-arabinofuranosylcytosine: Evidence of phosphoramidase activity" *J. Med. Chem.* (1996) 39:4569-4575.

Akdas et al. "Glutathione S-transferase and multidrug-resistant phenotype in transitional cell carcinoma of the bladder" *Eur. Urol.* (1996) 29(4):483-486.

Almasan et al. "Genetic instability as a consequence of inappropriate entry into and progression through S-phase" *Cancer Metast. Rev.* (1995) 14:59-73.

Andresen et al. "Detection of C-ERBB-2 related protein in sera breast cancer patients" *Acta Oncol.* (1995) 34(4):499-504.

Anglada et al. "N,N-cyclization of carbodiimides with 2-(bromomethyl)acrylic acid. A direct entry to the system 5-methylene-6H-pyrimidine-2,4-dione, A new class of thymine analogues" *J. Heterocyclic Chem.* (Jul.-Aug. 1996) 33: 1259-1270.

Antelman et al. "Inhibition of tumor cell proliferation in vitro and in vivo by exogenous p110$^{RB}$, the retinoblastoma tumor suppressor protein" *Oncogene* (1995) 10:697-704.

Asakura and Robins, "Cerium(IV) catalyzed iodination at C5 of uracil nucleosides" *Tetrahedron Lett.* (1988) 29(23):2855-2858.

Asakura and Robins "Cerium(IV)-mediated halogenation at C-5 of uracil derivatives" *J. Org. Chem.* (1990) 55:4928-4933.

Ayisi et al. "Comparison of the antiviral effects of 5-methoxymethyldeoxyuridine-5'-monophosphate with adenine arabinoside-5'-monophosphate" *Antivir. Res.* (1983) 3:161-174.

Bagshawe "Antibody-directed enzyme prodrug therapy: A review", *Drug Develop. Res.* (1995) 34(2):220-230.

Bajetta et al. "A pilot safety study of capecitabine, a new oral flouropyrimidine, in patients with advanced neoplastic disease" *Tumori* (1996) 82:450-452.

Balzarini et al. "Incorporation of 5-substituted pyrimidine nucleoside analogues into DNA of a thymidylate synthetase-deficient murine FM3A carcinoma cell line" *Meth. Find. Exp. Clin. Pharmacol.* (1985) 7(1):19-28.

Balzarini et al. "Thymidylate synthase is the principal target enzyme for the cytostatic activity of (E)-5-(2-bromovinyl)-2'-deoxyuridine against murine mammary carcinoma (FM3A) cells transformed with the herpes simplex virus type 1 or type 2 thymidine kinase gene" *Mol. Pharmacol.* (1987) 32:410-416.

Balzarini et al. "Differential mechanism of cytostatic effect of (E)-5-(2-bromovinyl)-2'-deoxyuridine, 9-(1,3-dihydroxy-2-propoxymethyl)guanine, and other antiherpetic drugs on tumor cells transfected by the thymidine kinase gene of herpes simplex virus type 1 or type 2" *J. Biol. Chem.* (1993) 268(9):6332-6337.

Balzarini et al. "Anti-HIV and anti-HBV activity and resistance profile of 2',3'-dideoxy-3'-thiacytidine (3TC) and its arylphosphoramidate derivative CF 1109" *Biochem. Biophy. Res. Co.* (1996) 225:363-369.

Balzarini et al. "Conversion of 2',3'-dideoxyadenosine (ddA) and 2',3'-didehydro-2',3'-dideoxyadenosine (d4A) to their corresponding aryloxyphosphoramidate derivatives markedly potentiates their activity against human immunodeficiency virus and hepatitis B virus" *FEBS Lett.* (1997) 410:324-328.

Banerjee et al. "Molecular mechanisms of resistance to antifolates, a review" *Acta Biochim. Pol.* (1995) 42(4):457-464.

Banerjee et al. "Role of E2F-1 in chemosensitivity" *Cancer Res.* (Oct. 1, 1998) 58:4292-4296.

Barbato, et al. "Synthesis of bridged pyrimidine nucleosides and triazo [4,3-c] pyrimidine nucleoside analogues" *Nucleos. Nucleot.* (1991) 10(4):853-866.

Barbour et al. "A naturally occurring tyrosine to histidine replacement at residue 33 of human thymidylate synthase confers resistance to 5-fluoro-2'-deoxyuridine in mammalian and bacterial cells" *Mol. Pharmacol.* (1992) 42:242-248.

Barr "Inhibition of thymidylate synthetase by 5-alkynyl-2'-deoxyuridylates" *J. Med. Chem.* (1981) 24(12):1385-1388.

Barr et al. "Thymidylate synthetase-catalyzed conversions of E-5-(2-bromovinyl)-2'-deoxyuridylate" *J. Biol. Chem.* (1983) 258(22):13627-13631, Nov. 25, 1983.

Barr et al. "Reaction of 5-ethynyl-2'-deoxyuridylate with thiols and thymidylate synthetase" *Biochemistry* (1983) 22:1606-1703.

Barrett "Trapping of the C5 methylene intermediate in thymidylate synthase" *J. Am. Chem. Soc.* (1998) 120:449-450.

Benzaria et al. "Synthesis, in vitro antiviral evaluation, and stability studies of bis(S-acyl-2-thioethyl) ester derivatives of 9-[2-(phosphonomethoxy)ethyl]adenine (PMEA) as potential PMEA prodrugs with improved oral bioavailability" *J. Med. Chem.* (1996) 39:4958-4965.

Bergstrom et al. "C-5-substituted pyrimidine nucleosides. 3. Reaction of allylic chlorides, alcohols, and acetates with pyrimidine nucleoside derived organopalladium intermediates" *J. Org. Chem.* (1981) 46(7):1432-1441.

Bergstrom et al. "Synthesis of (E)-5-(3,3,3-trifluoro-1-propenyl)-2'-deoxyuridine and related analogues: Potent and unusually selective antiviral activity of (E)5-(3,3,3-trifluoro-1-propenyl)-2'-deoxyuridine against herpes simplex virus type 1" *J. Med. Chem.* (1984) 27:279-284.

Bertino et al. "Resistance mechanisms to methotrexate in tumors" *Stem Cells* (1996) 14:5-9.

Bigge et al. "Palladium-catalyzed coupling reactions of uracil nucleosides and nucleotides" *J. Amer. Chem. Soc.* (Mar. 12, 1980) 102(6):2033-2038.

Blackledge "New developments in cancer treatment with the novel thymidylate synthase inhibitor raltitrexed ('Tomudex')" *British J. Cancer* (1998) 77(Supp 2):29-37.

Bosslet et al. "A novel one-step tumor-selective prodrug activation system" *Tumor Targeting* (1995) 1:45-50.

Bosslet et al. "Elucidation of the mechanism enabling tumor selective prodrug monotherapy" *Cancer Res.* (Mar. 15, 1998) 58:1195-1201.

Brison "Gene amplification and tumor progression" *Biochim. Biophys. Acta* (1993) 1155:25-41.

Carl et al. "Protease-activated 'prodrugs' for cancer chemotherapy" *PNAS USA* (Apr. 1980) 77(4):2224-2228.

Carreras and Santi "The catalytic mechanism and structure of thymidylate synthase" *Annu. Rev. Biochem.* (1995) 64:721-762.

Carter et al. "Humanization of an anti-p185$^{HER2}$ antibody for human cancer therapy" *PNAS USA* (May 1992) 89:4285-4289.

Cava and Levinson "Thionation reactions of Lawesson's reagents" *Tetrahedron* (1985) 41(22):5061-5087.

Chakravarty et al. "Plasmin-activated prodrugs for cancer chemotherapy. 2. Synthesis and biological activity of peptidyl derivatives of doxorubicin" *J. Med. Chem.* (1983) 26(5):638-644.

Chaudhuri and Kool "Very high affinity DNA recognition by bicyclic and cross-linked oligonucleotides" *J. Am. Chem. Soc.* (1995) 117:10434-10442.

Chen et al. "Sensitization of human breast cancer cells to cyclophosphamide and ifosfamide by transfer of a liver cytochrome P450 gene" *Cancer Res.* (Mar. 15, 1996) 56:1331-1340.

Cho and Johnson "(E)-5-(3-oxopropen-1-yl)-2'-deoxyuridine and (E)-5-(3-oxopropen-1-yl)-2',3'-dideoxyuridine; New antiviral agents: Synthesis and biological activity" *Tetrahedron Lett.* (1994) 35(8):11419-1152.

Clarke. "Animal models of breast cancer: Their diversity and role in biomedical research" *Breast Cancer Res. Tr.* (1996) 39:1-6.

Coderre et al. "Mechanism of action of 2',5-difluoro-1-arabinosyluracil" *J. Med. Chem.* (1983) 26(8):1149-1152.

Colacino "Mechanisms for the anti-hepatitis B virus activity and mitochondrial toxicity of fialuridine (FIAU)" *Antivir. Res.* (1996) 29:125-139.

Collins et al. "Suicide prodrugs activated by Thymidylate synthase: Rationale for treatment and noninvasive imaging of tumors with deoxyuridine analogues" *Clin. Cancer Res.* (Aug. 1999) 5:1976-1981.

Connors "Prodrugs in cancer chemotherapy" *Xenobiotica* (1996) 16(10/11):975-988.

Connors "Is there a future for cancer chemotherapy" *Ann. Oncol.* (1996) 7:445-452.

Connors and Knox "Prodrugs in cancer chemotherapy" *Stem Cells* (1995) 13:501-511.

Copur et al. "Thymidylate synthase gene amplification in human colon cancer cell lines resistant to 5-fluorouracil" *Biochem. Pharmacol.* (1995) 49(10):1419-1426.

Crisp "Synthesis of 5-alkenyl-2'-deoxyuridines via organostannanes" *Synth. Commun.* (1989) 19(11 & 12):2117-2123.

Dale et al. "The synthesis and enzymatic polymerization of nucleotides containing mercury: Potential tools for nucleic acid sequencing and structural analysis" *PNAS USA* (Aug. 1973) 70(8):2238-2242.

Davisson et al. "Expression of human thymidylate synthase in *Escherichia coli*" *J. Biol. Chem.* (1989) 264(16):9145-9148.

Davisson et al. "Expression of human thymidylate synthase in *Escherichia coli*. (Additions and corrections)" *J. Biol. Chem.* (Dec. 2, 1994) 269(48):30740.

DeClercq et al. "Nucleic acid related compounds. 40. Synthesis and biological activities of 5-alkynyluracil nucleosides" *J. Med. Chem.* (1983) 26:661-666.

Dicker et al. "Methotrexate resistance in an in vivo mouse tumor due to a non-active-site dihydrofolate reductase mutation" *PNAS USA* (Dec. 1993) 90:11797-11801.

Dirvin et al. "The role of human glutathione S-transferase isoenzymes in the formation of glutathione conjugates of the alkylating cytostatic drug thiotepa" *Cancer Res.* (Apr. 15, 1995) 55:1701-1706.

Dorr and von Hoff "PALA" In : *Cancer Chemotherapy Handbook*, 2nd Edition, Appelton & Lange, Norwalk Connecticut (1994) pp. 768-773.

Dunn, III et al., "Solution of the conformation and alignment tensors for the binding of trimethoprim and its analogs to dihydrofolate reductase: 3D-quantitative structure-activity relationship study using molecular shape analysis, 3-way partial least-squares regression, and 3-way factor analysis" *J. Med. Chem.* (1996) 39:4825-4832.

Dyer et al. "Nucleic Acids Chemistry: Improved and new synthetic procedures, methods, and techniques" Townsend, L. B. & Tipson, R. S., eds. (Wiley-Interscience, New York, NY) (1991) 4:79-83.

Eccles et al. "Significance of the c-erbB family of receptor tyrosine kinases in metastatic cancer and their potential as targets for immunotherapy" Invasion Metastasis (1994-95) 14(1-6):337-348.

Eisenbrand et al. "An approach towards more selective anticancer agents" J. Synthetic Organic Chem. (1996) 10:1246-1258.

Evard et al. "An in vitro nucleoside analog screening method for cancer gene therapy" Chem. Abstracts (1996) 126:Abstract No. 26514.

Farquhar et al. "Synthesis and antitumor evaluation of bis[(pivaloyloxy)methyl] 2'-deoxy-5-fluorouridine 5'-monophosphate (FdUMP): A strategy to introduce nucleotides into cells" J. Med. Chem. (1994) 37:3902-3909.

Farquhar et al. "5'-[4-pivaloyloxy)-1,3,2-dioxaphosphorinan-2-yl]-2'-deoxy-5-fluorouridine: A membrane-permeating prodrug of 5-fluoro-2'-deoxyuridylic acid (FdUMP)" J. Med. Chem. (1995) 38:488-495.

Farrugia et al. "Single agent infusional 5-fluorouracil is not effective second-line therapy after raltitrexed (Tomudex®) in advanced colorectal cancer" Eur. J. Cancer (1998) 34(7):987-991.

Felip et al. "Overexpression of c-erbB-2 in epithelial ovarian cancer" Cancer (Apr. 15, 1995) 75(8):2147-2152.

Finch, "Radiation Injury" In: Harrison's Principles of Internal Medicine, 12th Edition, McGraw-Hill, Inc., New York, NY (1991) 2204-2208.

Finer-Moore et al. "Refined structures of substrate-bound and phosphate-bound thymidylate synthase from Lactobacillus casei" J. Mol. Biol. (1993) 232:1101-1116.

Finer-Moore et al. "Crystal structure of thymidylate synthase from T4 phage: Component of a deoxynucleoside triphosphate-synthesizing complex" Biochemistry (1994) 33:15459-15468.

Firestone et al. "A comparison of the effects of antitumor agents upon normal human epidermal keratinocytes and human squamous cell carcinoma" Chem Abstracts (1990) 113:Abstract No. 254.

Freed et al. "Evidence for acyloxymethyl esters of pyrimidine 5'-deoxyribonucleotides as extracellular sources of active 5'-deoxyribonucleotides in cultured cells" Biochem. Pharmacol. (1989) 38(19):3193-3198.

Fries et al. "Synthesis and biological evaluation of 5-fluoro-2'-deoxyuridine phosphoramidate analogs" J. Med. Chem. (1995) 38(14):2672-2680.

Garrett et al. "Thymidylate synthetase. Catalysis of dehalogenation of 5-bromo-and 5-iodo-2'-deoxyuridylate" Biochemistry (1979) 18(13):2798-2804.

Goldberg et al. "Novel cell imaging techniques show induction of apoptosis and proliferation in mesothalial cells by asbestos" Am. J. Respir. Cell Mol. Biol. (1997) 17:265-271.

Goldstein and Brown "Genetic aspects of disease" In: Harrison's Principles of Internal Medicine, 12th Edition, McGraw-Hill, Inc., New York, NY (1991) pp. 21-76.

Goodwin et al. "Incorporation of alkylthiol chains at C-5 of deoxyuridine" Tetrahedron Lett. (1993) 34(35):5549-5552.

Gottesmann et al. "Genetic analysis of the multidrug transporter" Annu. Rev. Genet. (1995) 29:607-649.

Graham et al. "DNA duplexes stabilized by modified monomer residues: Synthesis and stability" J. Chem. Soc. Perkin Trans. (1998) 1:1131-1138.

Gros et al. "Isolation and expression of a complementary DNA that confers multidrug resistance" Nature (Oct. 1986) 323:728-731.

Gros et al. "Mammalian multidrug resistance gene: Complete cDNA sequence indicates strong homology to bacterial transport proteins" Cell (Nov. 7, 1986) 47:471-380.

Gros et al. "Isolation and characterization of DNA sequences amplified in multidrug-resistant hamster cells" PNAS USA (Jan. 1986) 83:337-341.

Gudkov et al. "Cloning and characterization of DNA sequences amplified in multidrug-resistant djungarian hamster and mouse cells" Somat. Cell Mol. Genet. (1987) 13(6):609-619.

Handfield and Levesque "Strategies for isolation of in vitro expressed genes from bacteria" FEMS Microbiol. Revs. (1999) 23:69-91.

Hardy et al. "Atomic structure of thymidylate synthase: Target for rational drug design" Science (Jan. 23, 1987) 235:448-455.

Harris et al. "Adenovirus-mediated p53 gene transfer inhibits growth of human tumor cells expressing mutant p53 proteion" Cancer Gene Ther. (1996) 3(2):121-130.

Hashimoto et al. "Simple separation of tritiated water and [$^3$H]deoxyuridine from [5-$^3$H]deoxyuridine 5'-monophosphate in the thymidylate synthase assay" Anal. Biochem. (1987) 167:340-346.

Hiedelberger et al. "Fluorinated pyrimidines and their nucleosides" Adv. Enzymol. Related Areas Mol. Biol. (1983) 54:57-119.

Hengstschläger et al. "The role of p16 in the E2F-dependent thymidine kinase regulation" Oncogene (1996) 12:1635-1643.

Hobbs, Jr. "Palladium-catalyzed synthesis of alkynylamino nucleosides. A universal linker for nucleic acids" J. Org. Chem. )1989) 54:3420-3422.

Horikoshi et al. "Quantitation of thymidylate synthase, dihydrofloate reductase, and DT-diaphorase gene expression in human tumors using the polymerase chain reaction" Cancer Res. (Jan. 1, 1992) 52:108-116.

Horn et al. "Fialuridine is phosphorylated and inhibits DNA synthesis in isolated rat hepatic mitochondria" Antivir. Res. (1997) 34:71-74.

Hostetler et al. "Enhanced oral absorption and antiviral activity of 1-O-octadecyl-sn-glycero-3-phospho-acyclovir and related compounds in hepatitis B virus infection, in vitro" Biochem. Pharmacol. (1997) 53:1815-1822.

Houze, et al. "Detection of thymidylate synthase gene expression levels in formalin-fixed paraffin embedded tissue by semiquantitative, nonradioactive reverse transcriptase polymerase chain reaction" Tumor Biol. (1997) 18:53-68.

Hsaio and Bardos".Synthesis of 5'-thymidinyl bis(1-aziridinyl)phosphinates as antineoplastic agents" J. Med. Chem. (1981) 24:887-889.

Hu et al. "Determination of absorption characteristics of AG337, a novel thymidylate synthase inhibitor, using a perfused rat intestinal model" J. Pharmaceutical Sciences (Jul. 1998) 87(7):886-890.

Huang and Santi "Active site general catalysts are not necessary for some proton transfer reactions of thymidylate synthase" Biochemistry (1997) 36:1869-1873.

Hudziak et al. "Amplified expression of the HER2-ERBB2 oncogene induces resistance to tumor necrosis factor $\alpha$ in NIH 3T3 cells" PNAS USA (Jul. 1988) 85:5102-5106.

Hudziak et al. "Selection for transformation and met protooncogene amplification in NIH 3T3 fibroblasts using tumor necrosis factor $\alpha$" Cell Growth & Differentiation (1990) 1:129-134.

Husak et al. "Pseudotumour of the tongue caused by herpes simplex virus type 2 in an HIV-1 infected immunosuppressed patient" Brit. J. Dermatol. (1998) 139:118-121.

Imai et al. "Studies on phosphorylation. IV. Selective phosphorylation of the primary hydroxyl group in nucleosides" J. Org. Chem. (Jun. 1969) 34(6):1547-1550.

Jackman et al. "Quinazoline-based thymidylate synthase inhibitors: Relationship between structural modifications and polyglutamation" Anti-Cancer Drug Design (1995) 10:573-589.

Johnston et al. "Production and characterization of monoclonal antibodies that localize human thymidylate synthase in the cytoplasm of human cells and tissue" Cancer Res. (Dec. 15, 1991) 51:6668-6676.

Johnston "The role of thymidylate synthase expression in prognosis and outcome of adjuvant chemotherapy in patients with rectal cancer" J. Clin. Oncol. (Dec. 1994) 12(12):2640-2647.

Kamb "Cyclin-dependent kinase inhibitors and human cancer" Curr. Top. Microbiol. Immunol. (1998) 227:139-148.

Kashani-Sabet et al. "Detection of drug resistance in human tumors by in vitro enzymatic amplification" Cancer Res. (Oct. 15, 1988) 48:5775-5778.

Katki et al. "Prodrugs activated by thymidylate synthase: Treatment of tumors with deoxyuridine analogs" Proc. Amer. Assoc. Cancer Res. (Mar. 1998) 39:Abstract No. 1275.

Klecker et al. "Toxicity, metabolism, DNA incorporation with lack of repair, and lactate production for 1-(2'-fluoro-2'-deoxy-$\beta$-D-arabinofuranosyl)-5-iodouracil in U-937 and MOLT-4 cells" Mol. Pharmacol. (1994) 46:1204-1209.

Knighton et al. "Structure of and kinetic channelling in bifunctional dihydrofolate reductase-thymidylate synthase" *Nature Struct. Biol.* (Mar. 1994) 1(3):186-194.

Kobayashi et al. "Effect of hammerhead ribozyme against human thymidylate synthase on the cytotoxicity of thymidylate synthase inhibitors" *Jpn. J. Cancer Res.* (Nov. 1995) 86:1014-1018.

Kodama et al. "Evaluation of antiherpetic compounds using a gastric cancer cell line: Pronounced activity of BVDU against herpes simplex virus replication" *Microbiol. Immunol.* (1996) 40(5):359-363.

Kumar et al. "Synthesis and biological evaluation of some cyclic phosphoramidate nucleoside derivatives" *J. Med. Chem.* (Sep. 1990) 33(9):2368-2374.

Kundu et al. "Synthesis and biological activities of [E]-5-(2-acylvinyl) uracils" *Eur. J. Med. Chem.* (1993) 28:473-479.

Kuroboshi and Hiyama "A facile synthesis of difluoromethylene compounds by oxidative fluorodesulfurization of dithioacetals using tetrabutylammonium dihydrogentrifluoride and N-halo compounds" *SYNLETT* (Dec. 1991) pp. 909-910.

Kuroboshi and Hiyama "A facile synthesis of α,α-difluoroalkyl ethers and carbonyl fluoride acetals by oxidative desulfurization-fluorination" *SYNLETT* (Apr. 1994) pp. 251-252.

Lam "Application fo combinatorial library methods in cancer research and drug discovery" *Anti-Cancer Drug Design* (1997) 12:145-167.

Larsson et al. "Thymidylate synthase in advanced gastrointestinal and breast cancers" *Acta Oncologica* (1996) 35(4):469-472.

Lasic "Doxorubicin in sterically stabilized liposomes" *Nature* (Apr. 11, 1996) 380:561-562.

Lewis et al. "A serum-resistant cytofection for cellular delivery of antisense oligodeoxynucleotides and plasmid DNA" *PNAS USA* (Apr. 1996) 93:3176-3181.

Li et al. "Lack of functional retinoblastoma protein mediates increased resistance to antimetabolites in human sarcoma cell lines" *PNAS USA* (Oct. 1995) 92:10436-10440.

Lin et al., "Rhenium 188 hydroxyethylidene diphosphonate: a new generator-produced radiotherapeutic drug of potential value for the treatment of bone metastases" *Eur. J. Nucl. Med.* 24(6):590-595 (Jun. 1997).

Livak et al. "Detection of single base differences using biotinylated nucleotides with very long linker arms" *Nucl. Acids Res.* (1992) 20(18):4831-4837.

Livingstone et al. "Altered cell cycle arrest and gene amplification potential accompany loss of wild-type p53" *Cell* (Sep. 18, 1992) 70:923-935.

Lönn et al. "Higher frequency of gene amplification in breast cancer patients who received adjuvant chemotherapy" *Cancer* (Jan. 1, 1996) 77(1):107-112.

Lovejoy et al. "Animal models and the molecular pathology of cancer" *J. Pathol.* (1997) 181:130-135.

Masters and Altardi "The nucleotide sequence of the cDNA coding for the human dihydrofolic acid reductase" *Gene* (1983) 21:59-63.

McGuigan et al. "Certain phosphoramidate derivatives of dideoxy uridine (ddU) are active against HIV and successfully by-pass thymidine kinase" *FEBS Let* (1994) 351:11-14.

McGuigan "Aryl phosphate derivatives of AZT retain activity against HIV1 in cell lines which are resistant to the action of AZT" *Antivir. Res.* (1992) 17:311-321.

McGuigan "Intracellular delivery of bioactive AZT nucleotides by aryl phosphate derivatives of AZT" *J. Med. Chem.* (1993) 36:1048-1052.

McGuigan "Aryl phosphoramidate derivatives of d4T have improved anti-HIV efficacy in tissue culture and may act by the generation of a novel intracellular metabolite" *J. Med. Chem.* (1996) 39:1748-1753.

McGuigan et al. "Synthesis and evaluation of some masked phosphate esters of the anti-herpetic drug 882C (netivudine) as potential antiviral agents" *Antivir. Chem. Chemoth.* (1998) 9:233-243.

McIntee "Probing the mechanism of action and decomposition of amino acid phosphomonoester amidates of antiviral nucleoside prodrugs" *J. Med. Chem.* (1997) 40:3323-3331.

McKay et al. "Broad spectrum aminoglycoside phosphotransferase type III *Enterococcus*: Overexpression, purification, and substrate specificity" *Biochemistry* (1994) 33:6936-6944.

Mead et al. "Pharmacologic aspects of homofolate derivatives in relation to amethopterin-resistant murine leukemia" *Cancer Res.* (Nov. 1966) 26(1):2374-2379.

Meden et al. "Elevated serum levels of a c-erbB-2 oncogene product in ovarian cancer patients and in pregnancy" *J. Cancer Res. Clin. Oncol.* (1994) 120:378-381.

Meier et al. "ADA-bypass by lipophilic cyclosal-ddAMP pronucleotides a second example of the efficiency of the *cyclo*sal-concept" *Bioorg. Med. Chem. Lett.* (1997) 7(12):1577-1582.

Meier et al. "Cyclic saligenyl phosphotriesters of 2',3'-dideoxy-2',3'-didehydrothymidine (d4T)—a new pro-nucleotide approach" *Bioorg Med. Chem. Lett.* (1997) 7(2):99-104.

Meier et al. "*Cyclo*Sal-pro-nucleotides: The design and biological evaluation of a new class of lipophilic nucleotide prodrugs" *Int'l. Antiviral News* (1997) 5(10):183-185.

Melton et al. "Antibody-directed enzyme prodrug therapy (ADEPT). Review article" *Drugs of the Future* (1996) 21(2):167-181.

Melton and Sherwood "Antibody-enzyme conjugates for cancer therapy" *J. Natl. Cancer Inst.* (Feb. 21, 1996) 88(3/4)153-165.

Midgley and Kerr "Colorectal cancer" *Lancet* (Jan. 30, 1999) 353:391-399.

Montfort and Weichsel "Thymidylate synthase: Structure, inhibition, and strained conformations during catalysis" *Pharmacol. Ther.* (1997) 76(1-3):29-43.

Montgomery et al., "Phosphonate analogue of 2'-deoxy-f-fluorouridylic acid" *J. Med. Chem.* (1979) 22(1):109-111.

Morgan et al. "Tumor efficacy and bone marrow-sparing properties of TER286, a cytotoxin activated by glutathione S-transferase" *Cancer Res.* (Jun. 15, 1998) 58:2568-2575.

Murakami and Sekiya "Accumulation of genetic alterations and their significance in each primary human cancer and cell line" *Mutat. Res.* (1998) 400(1-2):421-437.

Nakano et al., "Critical role of phenylalanine 34 of human dihydrofolate reductase in substrate and inhibitor binding and in catalysis" *Biochemistry* (1994) 33:9945-9952.

Nichol and Hakala "Comparative growth-inhibitory activity of homofolic aid against cell lines sensitive and resistant to amethopterin" *Biochem. Pharmacol.* (Oct. 1966) 15(10):1621-1623.

Nooter and Stoter "Molecular mechanisms of multidrug resistance in cancer chemotherapy" *Path. Res. Pract.* (1996) 192:768-780.

Osaki et al. "5-fluorouracil (5-FU) induced apoptosis in gastric cancer cells lines: Role of the p53 gene" *Apoptosis* (1997) 2:221-226.

Oshiro et al. "Genotoxic properties of (E)-5-(2-bromovinyl)-2'-deoxyuridine (BVDU)" *Fundam. Appl. Toxicol.* (1992) 18:491-498.

Pardo et al. "The incorporation of deoxyuridine monophosphate in DNA increases the sister-chromatid exchange yield" *Exp Cell Res.* (1987) 168:507-517.

Park et al. "Chemotherapy efficacy of E-5-(2-bromovinyl)-2'-deoxyuridine for orofacial infection with herpes simplex virus type 1 in mice" *J. Infectious Diseases* (Jun. 1982) 145(6):909-913.

Perry et al. "Plastic adaptation toward mutations in proteins: Structural comparison of thymidylate synthases" *Proteins* (1990) 8:315-333.

Pestalozzi et al. "Prognostic importance of thymidylate synthase expression in early breast cancer" *J. Clin. Oncol.* (May 1997) 15(5):1923-1931.

Peters et al. "Thymidylate synthase and drug resistance" *Eur. J. Can.* (1995) 31A(7/8):1299-1305.

Phelps et al. "Synthesis and biological activity of 5-fluoro-2'-deoxyuridine 5'-phosphorodiamidates" *J. Med. Chem.* (1980) 23:1229-1232.

Pupa et al. "The extracellular domain of the c-*erb*B-2 oncoprotein is released from tumor cells by proteolytic cleavage" *Oncogene* (1993) 8:2917-2923.

Roberts "An isotopic assay for thymidylate synthetase" *Biochemistry* (Nov. 1966) 5(11):3546-3548.

Robins and Barr "Nucleic acid related compounds. 31. Smooth and efficient palladium-copper catalyzed coupling of terminal alkynes with 5-iodouracil nucleosides" *Tetrahedron Lett.* (1981) 22:421-424.

Robins et al. "Nucleic acid related compounds. 38. Smooth and high-yield iodination and chlorination at C-5 of uracil bases and p-toluyl-protected nucleosides" *Can. J. Chem.* (1982) 60:554-557.

Robins and Barr "Nucleic acid compounds. 39. Efficient conversion of 5-iodo to 5-alkynyl and derived 5-substituted uracil bases and nucleosides" *J. Org. Chem.* (1983) 48:1854-1862.

Rode "Specificity of thymidylate synthase inactivation by 4,5-bisubstituted dUMP analogues" *M. Nencki Inst. Exp. Biol., Acta Biochimica Polonica* (1993) 40(3):363-368.

Rogulski et al. "Glioma cells transduced with an *Escherichia coli* CD/HSV-1 TK fusion gene exhibit enhanced metabolic suicide and radiosensitivity" *Hum. Gene Ther.* (Jan. 1, 1997) 8:73-85.

Roninson et al. "Amplification of specific DNA sequences correlates with multi-drug resistance in Chinese hamster cells" *Nature* (Jun. 14, 1984) 309:626-628.

Ruth and Bergstrom "C-5 sustituted pyrimidine nucleosides. 1. Synthesis of C-5 allyl, propyl, and propenyl uracil and cytosine nucleosides via organopalladium intermediates" *J. Org. Chem.* (1978) 43(14):2870-2876.

Santi "Perspectives on the design and biochemical pharmacology of inhibitors of thymldylate synthetase" *J. Med. Chem.* (Feb. 1980) 23(2):103-111.

Sastry et al. "Membrane-permeable dideoxyuridine 5'-monophosphate analogue inhibits human immunodeficiency virus infection" *Mol. Pharmacol.* (1992) 41:441-445.

Satyam et al. "Design, synthesis, and evaluation of latent alkylating agents activated by glutathione S-transferase" *J. Med. Chem.* (1996) 39:1736-1747.

Sauter et al. "Heterogeneity of *erb*B-2 gene amplification in bladder cancer" *Cancer Res.* (May 15, 1993) 53:2199-2203.

Schiffer et al. "Crystal structure of human thymidylate synthase: A structural mechanism for guiding substrates into the active site" *Biochemistry* (1995) 34:16279-16287.

Schimke "Gene amplification in cultured cells" *J. Biol.Chem.* (May 5, 1988) 263(13):5989-5992.

Schultz et al. "Role of thymidylate synthase in the antitumor activity of the multitargeted antifolate, LY231514" *Anticancer Res.* (1999) 19:437-444.

Segovia "*Leishmania* gene amplification: A mechanism of drug resistance" *Ann. Trop. Med. Parasit.* (1994) 88(2):123-130.

Shepard and Lewis "Resistance of tumor cells to tumor necrosis factor" *J. Clin. Immunol.* (1988) 8(5):333-341.

Simon and Schindler "Cell biological mechanisms of multidrug resistance in tumors" *PNAS USA* (Apr. 1994) 91:3497-3504.

Singh et al. "Studies on the preparation and isomeric composition of $^{186}$Re- and $^{188}$Re-pentavalent rhenium dimercaptosuccinic acid complex" *Nucl. Med. Commun.* (1993) 14:197-203.

Slamon et al. "Human breast cancer: Correlation of relapse and survival with amplification of the HER-2/*neu* oncogene" *Science* (Jan. 9, 1987) 235:177-182.

Slamon et al. "Studies of the HER-2*neu* proto-oncogene in human breast and ovarian cancer" *Science* (May 12, 1989) 244:707-712.

Slansky and Farnham "Transcripticnal regulaton of the dihydrofolate reductase gene" *BioEssays* (1996) 18(1):55-62.

Smith et al. "Regulation and mechanisms of gene amplification" *Phil. Trans. R. Soc. Lond. B* (1995) 347:49-56.

Snydman et al. "Analysis of trends in antimicrobial resistance patterns among clinical isolates of *Bacteroides fragilis* group species from 1990 to 1994" *Clin. Infect. Dis.* (1996) 23(Suppl. 1):S54-S65.

Staschke et al. "The in vitro anti-hepatitis B virus activity of FIAU [1-(2'-deoxy-2'-fluro-1-β-D-arabinofuranosyl-5-iodo)uracil] is selective, reversible, and determined, at least in part, by the host cell" *Antiviral Res.* (1994) 23:45-61.

Stout et al. "Structure-based design of inhibitors specific for bacterial thymidylate synthase" *Biochemistry* (1999) 38:1607-1617.

Stühlinger et al. "Clinical therapy and HER-2 oncogene amplification in breast cancer: Chemo vs radiotherapy" *J. Steroid Biochem. Molec. Biol.* (1994) 49(1):39-42.

Sugarman et al. "Recombinant human tumor necrosis factor-α: Effects on proliferation of normal and transformed cells in vitro" *Science* (Nov. 22, 1985) 230(4728):943-945.

Sukumar and Barbacid "Specific patterns of oncogene activation in transplacentally induced tumors" *PNAS USA* (Jan. 1990) 87:718-722.

Takeishi et al. "Nucleotide sequence of a functional cDNA for human thymidylate synthase" *Nucl. Acid Res.* (1985) 13(6):2035-2043.

Tannock "Treatment of cancer with radiation and drugs" *J. Clin. Oncol.* (Dec. 1996) 14(12):3156-3174.

Tennant et al. "Antiviral activity and toxicity of fialuridine in the woodchuk model of hepatitis B virus infection" *Hepatology* (Jul. 1998) 28(1):179-191.

Tolstikov et al. "Synthesis and DNA duplex stabilities of oligonucleotides containing C-5-(3-methoxypropynyl)-2'-deoxyuridine residues" *Nucleos. Nucleot.* (1997) 16(3):215-225.

Troutner "Chemical and physical properties of radionuclides" *Nucl. Med. Biol.* (1987) 14(3):171-176.

Ubeda and Habener "The large subunit of the DNA replication complex C (DSEB/RF-C140) cleaved and inactivated by Caspace-3 (CPP32/YAMA) during fas-induced apoptosis" *J. Biol. Chem.* (Aug. 1, 1997) 272(31):19562-19568.

Valette et al. "Decomposition pathways and in vitro HIV inhibitory effects of isoddA pronucleotides: Toward a rational approach for intracellular delivery of nucleoside 5'-monophosphates" *J. Med. Chem.* (1996) 39:1981-1990.

van de Vijver et al. "Amplification of the *neu* (c-*erbB*-2) oncogene in human mammary tumors is relatively frequent and is often accompained by amplification of the linked c-*erbA* oncogene" *Mol. Cell. Biol.* (May 1987) 7(5):2019-2023.

van Laar et al. "Comparision of 5-fluoro-2'-deoxyuridine with 5-fluorouracil and their role in the treatment of colorectal cancer" *Europoean J. Cancer* (1998) 34(3):296-306.

Volm et al. "Relationship of inherent resistance to doxorubicin, proliferative activity and expression of P-glycroprotein 170, and glutathione S-transferase-π in human lung tumors" *Cancer* (Aug. 15, 1992) 70(4):764-769.

Wahba and Friedkin "Direct spectrophotometric evidence for the oxidation of tetrahydrofolate during the enzymatic synthesis of thymidylate" *J. Biol. Chem.* (Mar. 1961) 236(3):C11-C12.

Wang et al. "Identification and characterization of Ich-3, a member of the interleukin-1β converting enzyme (ICE)/Ced-3 family and an upstream regulator of ICE" *J. Biol. Chem.* (Aug. 23, 1996) 271(34):20580-20587.

Wataya et al. "trans-5-(3,3,3-trifluoro-1-propenyl)2'-deoxyuridylate: A mechanism-based inhibitor of thymidylate synthetase" *J. Med. Chem.* (Apr. 1979) 22(4):339-340.

Wataya et al. "Interaction of thymidylate synthetase with 5-nitro-2'-deoxyuridylate" *J. Biol. Chem.* (Jun. 25, 1980) 255(12):5538-5544.

Wettergren et al. "Drug-specific rearrangements of chromosome 12 in hydroxyurea-resistant mouse SEWA cells: Support for chromosomal breakage model of gene amplification" *Somat. Cell Molec. Gen.* (1994) 20(4):267-285.

Yen et al. "Characterization of a hydroxyurea-resistant human KB cell line with supersensitivity to 6-thioguanine" *Cancer Res.* (Jul. 15, 1994) 54:3686-3691.

Yin et al. "Wild-type p53 restores cell cycle control and inhibits gene amplification in cells with mutant p53 alleles" *Cell* (Sep. 18, 1992) 70:937-948.

Zhou et al. "Target protease specificity of the viral serpin CrmA" *J. Biol. Chem.* (Mar. 21, 1997) 272(12):7797-7800.

Almansan et al. "Deficiency of retinoblastoma protein leads to inappropriate S-phase entry, activation of E2F-responsive genes, and apoptosis" PNAS, USA 92:5436-5440 (Jun. 1995).

Aschele et al. (Jun. 1999) "Immunohistochemical quantitation of thymidylate synthase expression in colorectal cancer metastases predicts for clinical outcome to fluorouracil-based chemotherapy" J. Clin. Oncol. 17(6):1760-1770.

Balzarini et al., "Increased sensitivity of thymidine kinase-deficient (TK-) tumor cell lines to the cell growth inhibitory effects of (E)-5-(2-bromovinyl)-2'-deoxyuridine (BVDU) and related compounds", Anticancer Research, vol. 6, 1986, pp. 1077-1084, Belgium, 1986.

Balzarini et al., "Marked inhibitory activity of masked aryloxy aminoacyl phosphoramidate derivatives of dideoxynucleoside analogues against visna virus infection", Journal of Acquired Immune Deficiency Syndromes and Human Retrovirology, vol. 17, pp. 296-302, Belgium, 1998.

Balzarini et al. "Mechanism of anti-HIV action of masked alaninyl d4T-MP derivatives" PNAS USA 93:7295-7299 (Jul. 1996).

Bastian et al. "Inhibition of thymidylate synthetase in thymidylate synthase" J. Med. Chem. 24:1385-1388 (1981).

Cruickshank et al. "Oligonucleotide labeling: A concise synthesis of a modified thymidine phoporamidite" Tetrahedron Lett. 29(41):5221-5224 (1988).

Curtin et al. "Mechanism of Cell Death following Thymidylate Synthase Inhibition: 2'-Deoxyuridine-5'-triphosphate Accumulation, DNA Damage, and Growth Inhibition following Exposure to CB3717 and Dipyridamole" Cancer Res. (May 1, 1991) 51:2346-2352.

Dolnick et al. "rTS Gene Expression is Associated with Altered Cell Sensitivity to Thymidylate Synthase Inhibitors" Adv. Enzyme Reg. (1996) 36:165-180.

Elder et al. "Immunohistochemically detected thymidylate synthase in colorectal cancer: An independent prognostic factor of survival" Clinical Cancer Research 6:488-492 (Feb. 2000).

Fan et al. "Functional roles of E2F in cell cycle regulation" Oncogene 14:1191-1200 (1997).

Freemantle et al. "Molecular characterisation of two cell lines selected for resistance to the folate-based thymidylate synthase inhibitor, ZD1694" British Journal of Cancer 71:925-930 (1995).

Funk "Cancer cell cycle control" Anticancer Research 19:4772-4780 (1999).

Goel et al. "Selective Intraperitoneal Biochemical Modulation of Methotrexate by Dipyridamole" J. Clin. Oncol. (Feb. 1989) 7(2):262-269.

Gorlick et al. "Drug Resistance in Colon Cancer" Semin. Olcol. (Dec. 1999) 26(6):606-611.

Griffith et al. "Differential Inhibition of Nucleoside Transport Systems in Mammalian Cells by a New Series of Compounds Related to Lidoflazine and Mioflazine" Biochem. Pharmacol. (1990) 40(10):2297-2303.

Howell et al. "Comparison of the Synergistic Potentiation of Etoposide, Doxorubicin, and Vinblastine Cytotoxicity by Dipyridamole" Cancer Res. (Jun. 15, 1989) 49:3178-3183.

Husain et al. "Elevation of topoisomerase I messenger RNA, protein, and catalytic activity in human tumors: Demonstration of tumor-type specificity and implications for cancer chemotherapy" Cancer Research 54:539-546 (Jan. 15, 1994).

Jackman "Folate-based thymidylate synthase inhibitors as anticancer drugs" Ann. Oncol. 6(9):871-881 (1995).

Jones and Mann "New methods of synthesis of β-aminoethylpyrazoles" J. Am. Cancer Soc. 75: 4048-4052 (1953).

Krajewska et al. "Pyrimidine ribonucleoside phosphorylase activity VS 5- and/or 6-substituted uracil and uridine analogues, including conformational aspects" Biochem. Pharmacol. 31(6):1097-1102 (1982).

Kraupp et al. "Membrane Transport of Nucleobases: Interaction with Inhibitors" Gen. Pharmacol. (1995) 26(6):1185-1190.

Lackey et al. "Enzyme-catalyzed therapeutic agent (ECTA) design: activation of the antitumor ECTA compound NB1011 by thymidylate synthase" Biochem. Pharmacol. (2001) 61:179-189.

Lee et al. "Inhibitio of mouse thymidylate synthase promoter activity by the wild-type p53 tumor suppressor protein" Exp. Cell Res. 234:270-276 (1997).

Lenz et al. "p53 and thymidylate synthase expression in untreated stage II colon cancer: associations with recurrence, survival, and site" Clinical Cancer Research 4:1227-1234 (May 1998).

Lehman et al. "Modulation of RTX cytotoxicity by thymidine and dipyridamole in vitro: implications for chemotherapy" Cancer Chemother. Pharmacol. (2000) 45:142-148.

Leichman et al. "Quantitation of Intratumoral Thymidylate Synthase Expression Predicts for Disseminated Colorectal Cancer Response and Resistance to Protracted-Infusion Fluorouracil and Weekly Leucovorin" J. Clin. Oncol. Oct. 1997) 15(1):3223-3229.

Lenz et al. "Thymidylate Synthase mRNA Level in Adenocarcinoma of the Stomach: A Predictor for Primary Tumor Response and Overall Survival" J. Clin. Oncol. (1995) 14(1):176-182.

Leś et al. "Modeling of reaction steps relevant to deoxyuridylate (dUMP) enzymatic methylation and thymidylate synthase mechanism-based inhibition" Journal of Biomolecular Structure & Dynamics 15(4):703-715 (1998).

Look et al. "Increased thymidine kinase and thymidylate synthase activities in human epithelial ovarian carcinoma" Anticancer Res. 17:2353-2356 (1997).

Maded et al. "Some characteristics of fetal and adult isoenzymes of thymidine kinase in human breast cancers" Bull. Cancer 75:187-194 (1998).

Mader et al. "Resistance to 5-fluorouracil" Gen. Pharma. 31(5):661-666 (1998).

Mahony et al. "Dipyridamole Kinetics" Clin. Pharmacol. Ther. (Mar. 1982) 31(3):330-338.

Mobashery et al. "Conscripting β-lactamase for use in drug delivery. Synthesis and biological activity of a cephalosporin C10-ester of an antibiotic dipeptide" J. Am. Chem. Soc. 108:1686-1688 (1986).

Negishi et al. "Enhancement of N4-aminocytidine-induced mutagenesis by Ni++ ion" Nucl. Acids Symposium 35:137-138 (1996).

Nelson et al. "Potentiation of Methotrexate Toxicity by Dipyridamole" Cancer Res. (Jun. 1984) 44:2493-2496.

Paradiso et al. "Thymidilate synthase and p53 primary tumour expression as predictive factors for advanced colorectal cancer patients" British J. of Cancer 82(3):560-567 (2000).

Pegram et al. "The effect of HER-2/neu overexperession on chemotherapeutic drug sensitivity in human breast and ovarian cancer cells" Oncogene 15:537-547 (1997).

Pluta et al., "Synthesis and biological properties of 4-hydroxy, 4-thio-5-pyrimidine derivatives" Boll. Chim. Farm. 138(1):30-33 (1999).

Ramu et al. "Circumvention of Adriamycin Resistance by Dipyridamole Analogues: A structure-activity relationship Study" Int. J. Cancer (1989) 43:487-491.

Romain et al. "Prognostic value of cytosolic thymidine kinase activity as a marker of proliferation in breast cancer" Int. J. Cancer 61:7-12 (1995).

Roth et al. "p53 tumor suppressor gene therapy for cancer" Oncology 13(10)(5):148-154 (1999).

Saboulard et al. "Characterization of the activation pathway of phosphoramidate triester prodrugs of stavudine and zidovudine" Mol. Pharmacol. 56:693-704 (1999).

Suki et al. "Risk classification for larger cell lymphoma using lactate dehydrogenase, beta-2 microglobulin, and thymidine kinase" Leukemia and Lymphoma 18:87-92 (1995).

Teh et al. "Tumor suppressor genes (TSG)" Anticancer Research 19:4715-4729 (1999).

van Larr et al. "Comparison of 5-fluoro-2'-deoxyuridine with 5-fluorouracil and their role in the treatment of colorectal cancer" European J. Cancer (1998) 34(3):296-306.

Wallis et al. "Synthesis and anti-HIV activity of C4-modified pyrimidine nucleosides" II Farmaco 54:83-89 (1999).

Zeid et al. "Synthesis of new thiolated acyclonucleosides with potential anti-HBV activity" Nucleosides & Nucleotides 18(1):95-111 (1999).

Balzarini et al. "Highly Selective Cytostatic Activity of (E)-5-(2-Bromovinyl)-2'-deoxyuridine Derivatives for Murine Mammary Carcinoma (FM3A) Cells Transformed with the Herpes Simplex Virus Type 1 Thymidine Kinase Gene" Molecular Pharmacology (1985) 29:581-587.

Balzarini et al. "The cytostatic activity of 5-(1-azidovinyl)-2'-deoxyuridine (AzVDU) against herpes simplex virus thymidine kinase gene-transfered FM3A cells is due to inhibition of thymidylate synthase and enhanced by UV light ($\lambda = 254$ nm) exposure" FEBS Lett. 373:41-44 (1995).

Barbato et al. "Synthesis of bridged pyrimidine nucleosides and triazo [4,3-c] pyrimidine nucleoside analogues" Nucleosides & Nucleotides 8(4):515-528 (1989).

Bathe et al. "Increased thymidylate synthase gene expression in liver metastases from colorectal carcinoma: implications for chemotherapeutic options and survival" Cancer J. Sci. Am. 5(1):34-40 (1999).

Bible et al. "Cytotoxic synergy between flavopiridol (NSC 649890, L86-8275) and various antineoplastic agents: the importance of sequence of administration" Cancer Res. 57(16):3375-80 (Aug. 15, 1997).

Bronzert, D.A. "Purification and Properties of Estrogen-responsive Cytoplasmic Thymidine Kinase from Human Breast Cancer" Can. Res. (Feb. 1981) 41:604-610.

Cass et al. "Recent advances in the molecular biology of nucleoside transporters of mammalian cells" Biochem. Cell Biol. 76(5):761-770 (1998).

Chou and Talalay, "Quantitative analysis of dose-effect relationships: the combined effects of multiple drugs or enzyme inhibitors" Adv. Enzyme Regul. 22:27-55 (1984).

Cordon-Cardo and Prives "At the crossroads of inflammation and tumorigenesis" J. Exp. Med. 190(10):1367-1370 (Nov. 15, 1999).

Costi et al. "Phthalein derivatives as a new tool for selectivity in thymidylate synthase inhibition" J. Med. Chem. 42(12):2112-2124 (1999).

Costi, et al. "Thymidylate Synthase Inhibition: A Structure-Based Rationale for Drug Design" Medical Research Review 18(1):21-42 (1998).

Curt "Cancer drug development: new targets for cancer treatment" Oncologist 1(3):II-III (1996).

DeClercq et al. "Antiviral Activity of Novel Deoxyuridine Derivatives" Current Chemotherapy: Proceedings of the International Congress of Chemotherapy 1:352-354 (Sep. 18, 1978).

DeClercq "Antiviral Activity Spectrum and Target of Action of Different Classes of Nucleoside Analogues" Nucleosides & Nucleosides 13(6&7):1271-1295 (1994).

DeClercq "In search of a selective antiviral chemotherapy" Clin. Micro. Review 10(4):674-693 (Oct. 1997).

Drake et al. "Resistance to Tomudex (ZD1694): Multifactorial in Human Breast and Colon Carcinoma Cell Lines" Biochem. Pharmacol. 51(10):1349-1355 (1996).

Farrow et al. "Synthesis and biological properties of novel phosphotriesters: A new approach to the introduction of biologically active nucleotides into cells" J. Med. Chem. 33(5):1400-1406 (1990).

Grem "Biochemical modulation of fluorouracil by dipyridamole: preclinical and clinical experience" Semin Oncol. 19(2 Suppl 3):56-65 (Apr. 1992).

Griengl et al. "Phosphonoformate and phosphonoacetate derivatives of 5-substituted 2'deoxyuridines: Synthesis and antiviral activity" J. Med. Chem. 31(9):1831-1839 (1988).

Hengstschlager, M. and E. Wawra "Cytofluorometric determination of thymidine kinase activity in a mixture of normal and neoplastic cells" Br. J. Cancer (1993) 67:1022-1025.

Johnston et al. "Thymidylate synthase gene and protein expression correlate and are associated with response to 5-fluorouracil in human colorectal and gastric tumors" Cancer Res. 55:1407-1412 (1995).

Komaki et al. "Difference in thymidylate synthetase activity in involved nodes compared with primary tumor in breast cancer patients" Breast Cancer Res. Treat. 35(2):157-162 (1995).

Leichman "Thymidylate synthase as a predictor of response" Oncl. 12(8Suppl.6):43-47 (Aug. 1998).

Libra, et al. "Thymidylate synthase mRNA levels are increased in liver metastases of colorectal cancer patients resistant to fluoropyrimidine-based chemotherapy" BMC Cancer 4:11 (2004).

Livingston et al. "Studies with tetrahydrohomofolate and thymidylate synthetase from amethopterin-resistant mouse leukemia cells" Biochem. 7(8):2814-2818 (1968).

Miao et al. "A Stepwise One Pot Synthesis of Alkyl Thiophosphoramidate Derivatives of Nucleosides" Synthetic Communications 32(8):1159-1167 (2002).

Niculescu-Duvaz et al. "Gene-directed enzyme prodrug therapy: A review of enzyme/prodrug combinations" Expert. Opin. Invest. Drugs 6(6):685-703 (1997).

Patterson et al. "Thymidine phosphorylase moderates thymidine-dependent rescue after exposure to the thymidylate synthase inhibitor ZD1694 (tomudex) in vitro" Cancer Res. 58:2737-2740 (1998).

Pedersen-Lane et al. "High-level expression of human thymidylate synthase" Protein Expression and Purification 10:256-262 (1997).

Rooney et al. "Comparative Genomic Hybridization Analysis of Chromosomal Alterations Induced by the Development of Resistance to Thymidylate Synthase Inhibitors" Cancer Res. 58:5042-5045 (Nov. 15, 1998).

Smith et al. "Response to doxorubicin of cultured normal and cancerous human mammary epithelial cells" J. Nat'l Cancer Inst. 74(2):341-347.

Touroutoglou et al. "Thymidylate synthase inhibitors" Clin. Cancer Res. 2(2):227-243 (Feb. 1996).

Tsavaris et al. "Multimodal biochemical modulation of 5-fluorouracil activity in advanced colorectal cancer with allopurinol, folinic acid and dipyridamol" J. Chemother. 2(2):123-126 (1990).

van Laar "Therapeutic efficacy of fluoropyrimidines depends on the duration of thymidylate synthase inhibition in the murine colon 26-B carcinoma tumor model" Clin. Cancer Res. 2(8):1327-1333 (1996).

van Triest et al. "Thymidylate synthase level as the main predictive parameter for sensitivity to 5-fluorouracil, but not for folate-based thymidylate synthase inhibitors, in 13 nonselected colon cancer lines" Clin. Cancer Res. 5(3):643-654 (1999).

Vlaykava et al. "Increased Thymidylate Synthase Gene Expression in Metastatic Melanoma" Oncology 54:146-152 (1997).

Whalen et al. "Human glutathione S-transferases" Seminars in Liver Disease 18(4):345-358 (1998).

Wildner et al. "Enzyme prodrug gene therapy: Synergistic use of the herpes simplex virus-cellular thymidine kinase/ganciclovir system and thymidylate synthase inhibitors for the treatment of colon cancer"n Cancer Res. 59(20):5233-5238 (1999).

Willson et al. "Phase I Clinical Trial of a Combination of Dipyridamole and Acivicin Based Upon Inhibition of Nucleoside Salvage" Cancer Res. 48:5585-5590 (Oct. 1, 1998).

Wolfe et al. "Antibody-directed enzyme prodrug therapy with the T268G mutant of human carboxypeptidase A1: in vitro and in vivo studies with prodrugs of methotrexate and the thymidylate synthase" Bioconjugate Chemistry 10(1):38-48 (1999).

* cited by examiner

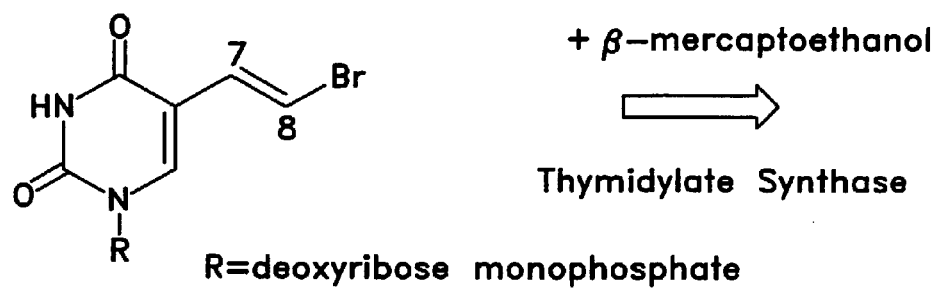
R=deoxyribose monophosphate
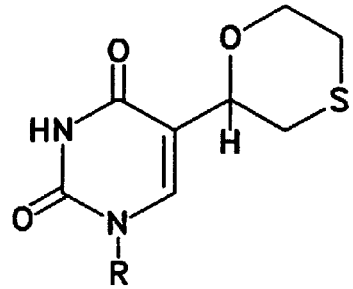
I.
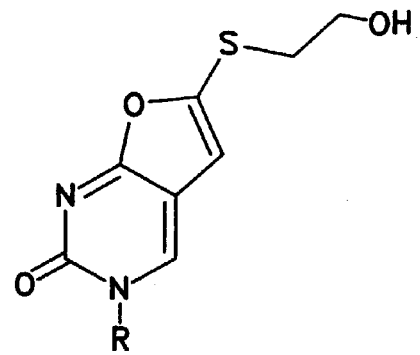
II.
Fig. 5

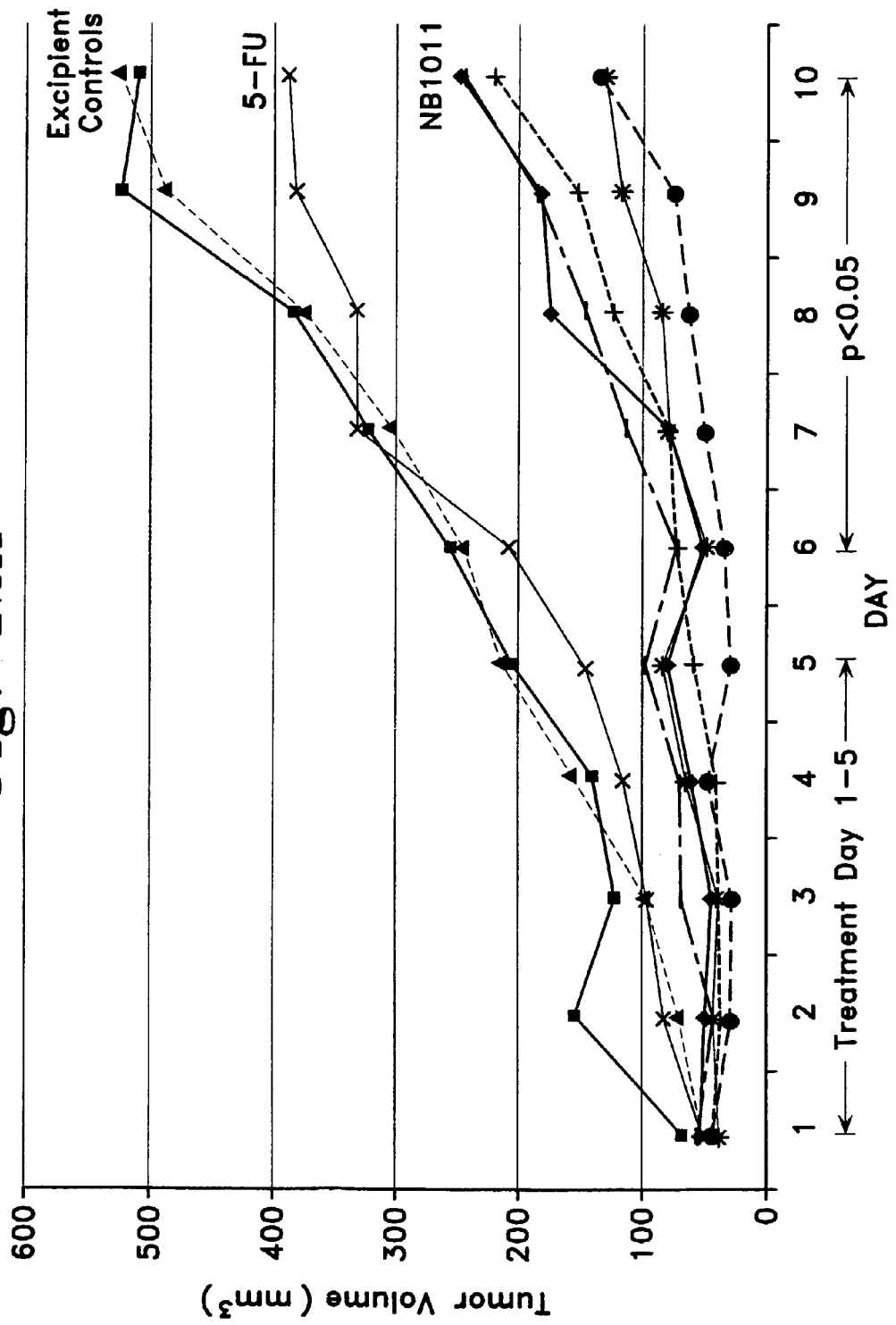

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial
<220> FEATURE:
<223> OTHER INFORMATION: Corresponding to bases 208-226 of thymidylate
      synthase cDNA sequence

<400> SEQUENCE: 1
gggcagatcc aacacatcc                                                  19

<210> SEQ ID NO 2
<211> LENGTH: 20
<212> TYPE: DNA
<213> ORGANISM: Artificial
<220> FEATURE:
<223> OTHER INFORMATION: antisense primer corresponding to bases 564-583

<400> SEQUENCE: 2
ggtcaactcc ctgtcctgaa                                                 20

<210> SEQ ID NO 3
<211> LENGTH: 19
<212> TYPE: DNA
<213> ORGANISM: Artificial
<220> FEATURE:
<223> OTHER INFORMATION: corresponding to bases 2643-2661 of b-actin
```

-continued

```
      gene sequence

<400> SEQUENCE: 3
gccaacacag tgctgtctg                                                  19

<210> SEQ ID NO 4
<211> LENGTH: 19
<212> TYPE: DNA
<213> ORGANISM: Artificial
<220> FEATURE:
<223> OTHER INFORMATION: antisense primer corresponding to bases
      2937-2955

<400> SEQUENCE: 4
ctcctgcttg ctgatccac                                                  19

<210> SEQ ID NO 5
<211> LENGTH: 26
<212> TYPE: DNA
<213> ORGANISM: Artificial
<220> FEATURE:
<223> OTHER INFORMATION: sense primer used for PCR amplification

<400> SEQUENCE: 5
cggaagcttg agccgcgtcc gccgca                                          26

<210> SEQ ID NO 6
<211> LENGTH: 26
<212> TYPE: DNA
<213> ORGANISM: Artificial
<220> FEATURE:
<223> OTHER INFORMATION: antisense primer used for PCR amplification

<400> SEQUENCE: 6
gaaggtaccc taaacagcca tttcca                                          26
```

METHODS FOR TREATING THERAPY-RESISTANT TUMORS

CROSS-REFERENCE TO RELATED APPLICATIONS

This application is the National Stage of International Application No. PCT/US00/20007, filed Jul. 21, 2000, which in turn claims the benefit under 35U.S.C. § 119(e) to the following U.S. provisional applications, Ser. Nos.: 60/153,855, filed Sep. 14, 1999 and 60/145,364, filed Jul. 22, 1999, the contents of which are hereby incorporated by reference into the present disclosure.

TECHNICAL FIELD

This invention relates to the field of cancer therapy, and in particular, compositions and methods for the treatment of therapy-resistant tumors.

BACKGROUND

Throughout and within this disclosure, various publications are referenced by first author and date, patent number or publication number. The full bibliographic citation for each reference can be found within the specification. The disclosures of these publications are hereby incorporated by reference into this disclosure to more fully describe the state of the art to which this invention pertains.

Resistance to chemotherapeutic treatments for cancer is a major health care problem. Resistance mechanisms can be classified as two types: endogenous and acquired. In cancer most drug resistance is enzyme mediated. Either the target enzyme is expressed at too high a level for the chemotherapeutic to block its activity without unacceptable toxicity to the host; or, alternatively, an enzyme is expressed by the diseased cell which rapidly modifies the chemotherapeutic, thereby abolishing its therapeutic activity. Endogenous resistance to chemotherapy can occur in cancer when the diseased cell loses tumor suppressor gene function (p53, RB, p16). When this occurs, enzymes such as thymidylate synthase (TS) and dihydrofolate reductase (DHFR) are expressed constitutively throughout the cell cycle (Yeager and Reznikoff (1998) J. Urol. 159 (2): 581-5; el-Deiry (1997) Curr. Opin. Oncol. 9 (1): 79-87; Goker, Waltham, et al. (1995) Blood 86(2):677-84; Banerjee, Ercikan-Abali, et al. (1995) Acta Biochem Pol. 42 (4): 457-64); Fan and Bertino (1997) Oncogene 14(10): 1191-1200; Slansky and Farnham (1996) Bioessays 18(1):55-62; Lenz, Danenberg, et al. (1998) Clin. Cancer Res. 4(5):1227-34; and Lee, et al. (1997) Exp. Cell Res. 234 (2): 270-6.) This results in increased endogenous resistance to the fluoropyrimidines (via elevated expression of TS) or to methotrexate (via elevated expression of DHFR). Approaches to new therapeutics have been largely limited to development of better enzyme inhibitors, or the search for new enzymes to inhibit (Hu, et al. (1998) J. Pharm. Sci. 87(7):886-90; Drake, et al. (1996) Biochem. Pharmacol. 51(10):1349-55; Schultz, et al. (1999) Anticancer Res. 19 (1A): 437-43; Touroutoglou and Pazdur (1996) Clin. Cancer. Res 2(2):227-43; and Handfield and Levesque (1999) FEMS Microbiol. Rev. 23(1):69-91). Applicants have developed a novel approach to development of therapeutics targeting well characterized enzymes. This technology is distinct from prior and historical approaches to cancer therapy and is referred to as "ECTA," for Enzyme Catalyzed Therapeutic Activation.

DISCLOSURE OF THE INVENTION

This invention provides a method for selectively inhibiting a pathological, neoplastic cell that is characterized by expression of an endogenous, intracellular activating enzyme. The method requires contacting the cell with an effective amount of a substrate compound thereby selectively inhibiting the proliferation of the cell. The enzyme is not inactivated by the substrate prodrug compound.

This invention also provides a method for screening for prodrugs selectively converted to a toxin in a cell by an endogenous, intracellular enzyme by contacting at least two test cells that express an endogenous, intracellular enzyme with the candidate prodrug and assaying for activation of the prodrug into toxic agents by the endogenous, intracellular enzyme.

BRIEF DESCRIPTION OF THE FIGURES

FIG. 5 is the structures of the products of the in vitro reaction. Structures of products of in vitro reaction of BVdUMP catalyzed by rHuTS. Structures I and II are consistent with mass ions identified in cell free reaction mixtures.

FIG. 12A shows that NB1011 inhibits growth of 5-FU resistant colon cancer. Treatment of nude mice bearing H630R10 (5FU Resistant) human colon carcinoma. Tumor measurements began on the first day of treatment (Day 1).

MODE(S) FOR CARRYING OUT THE INVENTION

Figure 1:
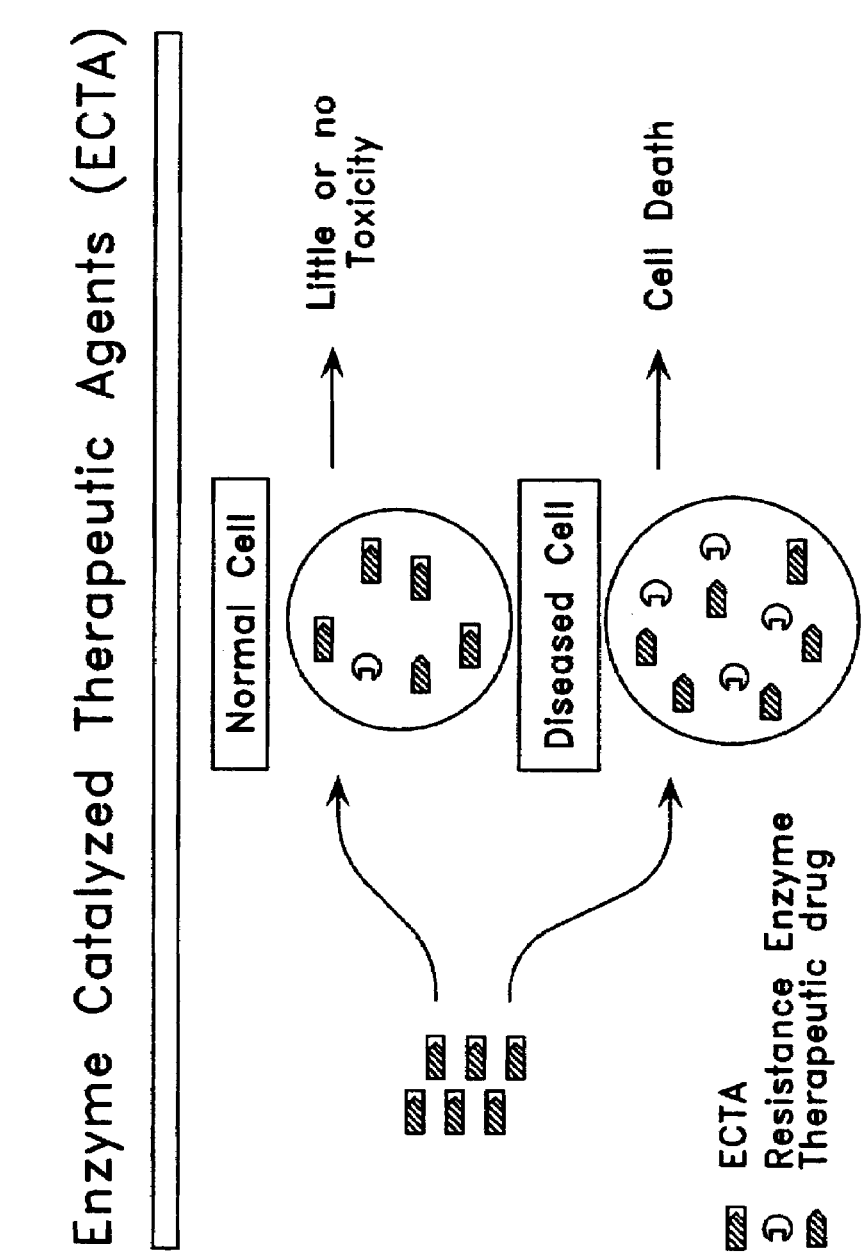
FIG. 1 schematically shows the mechanism of action of the ECTA prodrugs of this invention.

The practice of the present invention will employ, unless otherwise indicated, conventional techniques of molecular biology, medicinal chemistry, organic chemistry, microbiology, cell biology and recombinant DNA, which are within the skill of the art. See, e.g., Sambrook, et al. MOLECULAR CLONING: A LABORATORY MANUAL, 2$^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)) and ANIMAL CELL CULTURE (R. I. Freshney, ed. (1987)).

As used in the specification and claims, the singular form "a", "an" and "the" include plural references unless the context clearly dictates otherwise. For example, the term "a cell" includes a plurality of cells, including mixtures thereof.

The term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "composition" is intended to mean a combination of active agent and another compound or composition, inert (for example, a detectable agent or label or a pharmaceutically acceptable carrier) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'S PHARM. SCI., 15th Ed. (Mack Publ. Co., Easton (1975)).

An "effective amount" is an amount sufficient to effect beneficial or desired results. An effective amount can be administered in one or more administrations, applications or dosages.

A "subject," "individual" or "patient" is used interchangeably herein, which refers to a vertebrate, preferably a mammal, more preferably a human. Mammals include, but are not limited to, murines, simians, humans, farm animals, sport animals, and pets.

As used herein, the term "contacting" includes in vitro, ex vivo and in vivo administration of prodrug. When done in vivo, the prodrug is administered to a subject in an effective amount. As used herein, the term "subject" is intended to include any appropriate animal model, e.g., mouse, rat, rabbit, simian. It also includes administration to humans patients.

A "control" is an alternative subject or sample used in an experiment for comparison purpose. A control can be "positive" or "negative". For example, where the purpose of the experiment is to determine a correlation of an altered expression level of a gene with a particular type of cancer, it is generally preferable to use a positive control (a subject or a sample from a subject, carrying such alteration and exhibiting syndromes characteristic of that disease), and a negative control (a subject or a sample from a subject lacking the altered expression and clinical syndrome of that disease).

As used herein, the terms "pathological cells, "target cells", "test cells" and "hyperproliferative cells" encompass cells characterized by the activation by genetic mutation or the endogenous overexpression of an intracellular enzyme. In some embodiments, the overexpression of the enzyme is related to loss of tumor suppressor gene product function drug resistance or the genetic instability associated with a pathological phenotype. A number of cellular mechanisms are involved in drug resistance, e.g., altered metabolism of the drug, impermeability of the cell with regard to the active compound or accelerated drug elimination from the cell, altered specificity of an inhibited enzyme, increased production of a target molecule, increased repair of cytotoxic lesions, or the bypassing of an inhibited reaction by alternative biochemical pathways. Enzymes activated or overexpressed and related to drug resistance include, but are not limited to thymidylate synthase, dihydrofolate reductase, tyrosine kinases and multidrug resistant enzyme; and ATP-dependent multidrug resistance associated proteins and, in some diseases including colon and prostate cancer, topoisomerase I. Alternatively, resistance to one drug may confer resistance to other, biochemically distinct drugs.

Amplification of certain genes is involved in resistance to chemotherapy. Amplification of dihydrofolate reductase (DHFR) is related to resistance to methotrexate while amplification of the gene encoding thymidylate synthase is related to resistance to tumor treatment with 5-fluoropyrimidine. Amplification of genes associated with drug resistance can be detected and monitored by a modified polymerase chain reaction (PCR) as described in (Kashini-Sabet, et al. (1988) Cancer Res 48: 5775-5778) U.S. Pat. No. 5,085,983. Acquired drug resistance can be monitored by the detection of cytogenetic abnormalities, such as homogeneous chromosome staining regions and double minute chromosomes both of which are associated with gene amplification. Alternative assays include direct or indirect enzyme activity assays and both of which are associated with gene amplification and other methodologies (e.g. polymerase chain reaction or immunohistochemistry).

Alternatively, the pathological cell is characterized as having inactivated tumor suppressor function, e.g. loss or inactivation of retinoblastoma (RB) or p53, known to enhance expression of an activating enzyme such as TS.

Therapeutic Methods

In one aspect, this invention is directed to methods for inhibiting the proliferation of a pathological cell by contacting the cell with a substrate prodrug that is selectively converted to a toxin in the cell by an endogenous, intracellular activating enzyme. The methods and compositions of this invention are preferentially useful to inhibit the growth or proliferation of cells that endogenously express the intracellular enzyme, which occurs in some hyperproliferative or neoplastic cells, e.g., a gastric cancer cell, a colon cancer cell and a breast cancer cell. Examples of endogenous, intracellular enzymes that are selective targets and activating enzymes for the prodrugs of this invention include, but are not limited to, Thymidylate Synthase (TS) and Dihydrofolate Reductase ("DHFR"). The concepts of this invention are illustrated using the activating enzyme thymidylate synthase (TS). However, the use of TS is merely illustrative and the claims are not to be construed as limited to systems which target TS. Thymidylate Synthase is a well-characterized target for treatment of cancer, and has also been utilized as an infectious disease target. Thymidylate Synthase is an illustrative target, activating enzyme because of the high degree of characterization of its structure and function (Carreras and Santi (1995) Annu. Rev. Biochem. 64: 721-726), the fact that it is encoded by a single gene, not a gene family, for example, GST and finally, because over expression of this enzyme predicts resistance to chemotherapy and a more aggressive course of disease (Johnston and Allegra (1995) Cancer Res. 55(7):1407-12).

In one embodiment, the prodrug is a compound having a structure as defined in more detail herein. The term prodrug refers to precursors of active therapeutics. The perfect prodrug is one that is pharmacologically inert until activated by the intended mechanism. Prodrug strategies are meant to target potentially toxic therapies to the site of disease, thereby avoiding systemic toxicity. A number of approaches have been made to this goal. First attempts at a prodrug for cancer therapy were reported by Mead, et al. (1966) Cancer Res. 26: 2374-2379 and Nichol and Hakala (1966) Biochem. Pharmacol. 15: 1621-1623. The guiding principle of this effort was to target overexpressed dihydrofolate reductase in methotrexate-resistant leukemia. Self-poisoning of tumor cells was hoped for as the elevated dihydrofolate reductase in methotrexate-resistant tumor cells was supposed to convert homofolate into metabolic poison directed to thymidylate synthase. It was later discovered that the modest antitumor effects of homofolate are not due to metabolic activation, but more likely to inhibition of folate transport into cells (Livingston, et al. (1968) Biochem 7(8): 2814-2818). This, and subsequent, prodrug-like attempts to leverage tumor selective targets for therapeutics development are summarized in Table 1, below.

TABLE 1

Comparison of Prodrug Strategies

| Technology | Acronym | Description | Key References |
| --- | --- | --- | --- |
| Metabolic activation | None | Conversion of folate analogs to toxins via 'lethal synthesis.' | Mead, et al. (1966) supra. |
| Antibody directed prodrug therapy | ADEPT | Antibody-enzyme complex binds to tumor selective antigen. Prodrug is administered and activated when it encounters the antibody bound enzyme. | Syrigos and Epenetos (1999) Anticancer Res. 19(1A):605-13 |
| Gene directed prodrug therapy | GDEPT | Gene encoding activating enzyme is transduced into large T cells | Connors and Knox (1995) Stem Cells 13:501-511 |
| Enzyme directed prodrug therapy | EDEPT | Prodrugs are administered which are activated by extracellular enzymes present a high levels only at tumor site. | Breistol, et al. (1998) Eur. J. Cancer 34(19): 1602-1606 and Bosslet, et al. (1998) Cancer Res. 58:1195-1201. |
| Tumor Activated | "TAC" | Prodrugs activated by | Morgan, et al. |

TABLE 1-continued

Comparison of Prodrug Strategies

| Technology | Acronym | Description | Key References |
| --- | --- | --- | --- |
| Cytotoxin | | glutathione-s-transferase | (1998) supra |
| Enzyme catalyzed therapeutic activation | ECTA | Prodrugs are activated by enzymes overexpressed as a result of tumor suppressor gene loss and in vivo selection by chemotherapy | As disclosed herein |

One or more of the following issues has confounded these approaches: a) locating the activating enzyme appropriately and/or lack of tumor selectivity of the targeted enzyme; b) systemic distribution and resulting toxicity of the activated prodrug; and c) achieving the needed substrate enzyme specificity to prevent activation by enzymes other than the ones targeted. For instance, the glutathione-s-transferase (GST) prodrug that have been described by Morgan, et al. (1998) Cancer Res. 58: 2568-2575, while specific for GST, is not specific for only the tumor overexpressed GST-P1-1, but can also be activated by GST-A1-1. This leads to inappropriate drug activation and potential toxicity. Many of these issues are discussed in more detail in the cited publications provided in Table 1, supra. The method and compositions of this invention avoids prior prodrug failures by providing prodrugs that target enzymes that are selectively overexpressed in tumor cells by virtue of transcriptional activation and/or gene amplification occurring subsequent to tumor suppressor gene loss.

In an additional aspect of the invention, the activating enzyme is characterized as being overexpressed in the majority of cancers (those that have lost any of the p53, RB or p16 tumor suppressor functions), and especially in cancers that have been exposed to fluoropyrimidine therapeutics (5-FU, 5-FUdR, Xeloda) or other TS inhibitors (e.g., Tomudex). The prodrugs of this invention are further characterized as being essentially non-toxic to normal cells. This aspect further enhances the selectivity of the prodrugs because only abnormal or diseased cells provide an effective amount of the toxic metabolite of the prodrug to inhibit cellular proliferation or more preferentially, selectively kill the cell. Indeed, Applicants are the first to note that cells expressing more than normal amounts of activating enzymes are selectively killed by the methods and prodrugs of this invention, without regard to the activity of the enzyme, e.g., TS activity as measure by the method of Roberts (1966) Biochem. 5(11):3546-3548. Thus, it is the term "overexpressed" refers to the total amount of TS protein, not TS enzyme activity as measured by tritium release (Roberts (1966) supra). This is demonstrated in the Experimental Section, below.

Pharmaceutical development has focused on inhibitors. The rationale for the inhibitors has been that most tumor cells divide more frequently in vivo than most normal cells. As a result, the average amount of TS in tumor cells is higher than in their normal counterparts. Limited efficacy has been observed with these compounds, accompanied by significant dose-limiting toxicity. The most used of these compounds, the fluoropyrimidines, were developed in the middle of the twentieth century, and found utility in the treatment of advanced gastrointestinal cancers (Heidelberger, et al. (1983) Adv. Enzymol. Relat. Areas Mol. Biol. 54: 58-119). The initial development of 5-fluorouracil had additional support and rationale with Heidelberger's observation that, in cell culture, uracil is more rapidly metabolized by tumor cells than by normal cells (Heidelberger, et al. (1957) Fluorinated pyrimidines and their nucleosides in "Handbook of Experimental Pharmacology" pp. 193-231). Treatment response rates have hovered consistently around 25-30%. Patients with no treatment usually survive about 6 months, and with fluoropyrimidine-treatment, for up to one year (Midgley and Kerr (1999) Lancet 353 (9150): 391-9 and van Laar, Rustum, et al. (1998) Eur. J. Cancer 34 (3): 296-306).

Little or no increase in survival has occurred with the continuing development of alternative dosing strategies or new approaches to inhibition of TS activity. For instance, the development of more perfect TS inhibitors, like Tomudex, has not resulted in significant improvement in survival, although the toxicity profile of Tomudex is distinct from the fluoropyrimidines (Blackledge (1998) Br. J. Cancer 77 (Suppl. 2): 29-37). Finally, because fluoropyrimidine treatment and Tomudex treatment both result in increased levels of TS, a significant cross-resistance is observed. Fluoropyrimidine failures are refractory to Tomudex as well (Farrugia (1998) Eur. J. Cancer 34(7): 987-91). This current situation can be addressed by developing chemotherapeutics that attack 5FU/Tomudex resistant tumor cells by a novel mechanism.

Another aspect of this invention is a method for treating a pathological cell in a subject by administering to the subject a therapeutic amount of a prodrug that is converted to a toxin in a cell by an endogenous intracellular enzyme as defined herein. The enzyme is "overexpressed" and the cell being treated is a neoplastic or cancer cell.

When the prodrug is administered to a subject such as a mouse, a rat or a human patient, the prodrug can be added to a pharmaceutically acceptable carrier and systemically or topically administered.

To determine patients that can be beneficially treated, a tumor sample is removed from the patient and the cells are assayed for the level of expression of the target enzyme. If the expression is above that expressed in normal cells so that a toxic amount of the prodrug would cause administered without undesirable side effects, then the tumor or cells are determined to be beneficially treated and thus, the patient is suitable for the therapy of this invention. For example, if the target enzyme is expressed at least about 2 times and preferably about 3 times higher and more preferentially more than 4 times than normal cells, the patient is a suitable subject for the therapy method of this invention. Therapeutic amounts can be empirically determined and will vary with the pathology being treated, the subject being treated and the toxicity of the converted prodrug or cellular toxin.

When delivered to an animal, the method is useful to further confirm efficacy of the prodrug. As an example of an animal model, groups of nude mice (Balb/c NCR nu/nu female, Simonsen, Gilroy, Calif.) are each subcutaneously inoculated with about $10^5$ to about $10^9$ hyperproliferative, cancer or target cells as defined herein. When the tumor is established, the prodrug is administered, for example, by subcutaneous injection around the tumor. Tumor measurements to determine reduction of tumor size are made in two dimensions using venier calipers twice a week. Other animal models may also be employed as appropriate. This method is exemplified in the Materials and Methods section, infra.

Administration in vivo can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the prodrugs can be found below.

The prodrugs and compositions of the present invention can be used in the manufacture of medicaments and for the treatment of humans and other animals by administration in accordance with conventional procedures, such as an active ingredient in pharmaceutical compositions.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to a compound of the present invention, the pharmaceutical compositions can contain other pharmaceutically active compounds or a plurality of compounds of the invention.

More particularly, a compound of the formula of the present invention also referred to herein as the active ingredient, may be administered for therapy by any suitable route including oral, rectal, nasal, topical (including transdermal, aerosol, buccal and sublingual), vaginal, parental (including subcutaneous, intramuscular, intravenous and intradermal) and pulmonary. It will also be appreciated that the preferred route will vary with the condition and age of the recipient, and the disease being treated.

In general, a suitable dose for each of the above-named compounds, is in the range of about 1 to about 100 mg per kilogram body weight of the recipient per day, preferably in the range of about 1 to about 50 mg per kilogram body weight per day and most preferably in the range of about 1 to about 25 mg per kilogram body weight per day. Unless otherwise indicated, all weights of active ingredient are calculated as the parent compound of the formula of the present invention for salts or esters thereof, the weights would be increased proportionately. The desired dose is preferably presented as two, three, four, five, six or more sub-doses administered at appropriate intervals throughout the day. These sub-doses may be administered in unit dosage forms, for example, containing about 1 to about 100 mg, preferably about 1 to above about 25 mg, and most preferably about 5 to above about 25 mg of active ingredient per unit dosage form. It will be appreciated that appropriate dosages of the compounds and compositions of the invention may depend on the type and severity and stage of the disease and can vary from patient to patient. Determining the optimal dosage will generally involve the balancing of the level of therapeutic benefit against any risk or deleterious side effects of the treatments of the present invention.

Ideally, the prodrug should be administered to achieve peak concentrations of the active compound at sites of disease. This may be achieved, for example, by the intravenous injection of the prodrug, optionally in saline, or orally administered, for example, as a tablet, capsule or syrup containing the active ingredient. Desirable blood levels of the prodrug may be maintained by a continuous infusion to provide a therapeutic amount of the active ingredient within disease tissue. The use of operative combinations is contemplated to provide therapeutic combinations requiring a lower total dosage of the prodrug that may be required when each individual therapeutic compound or method is used alone, thereby reducing adverse effects.

Figure 6:
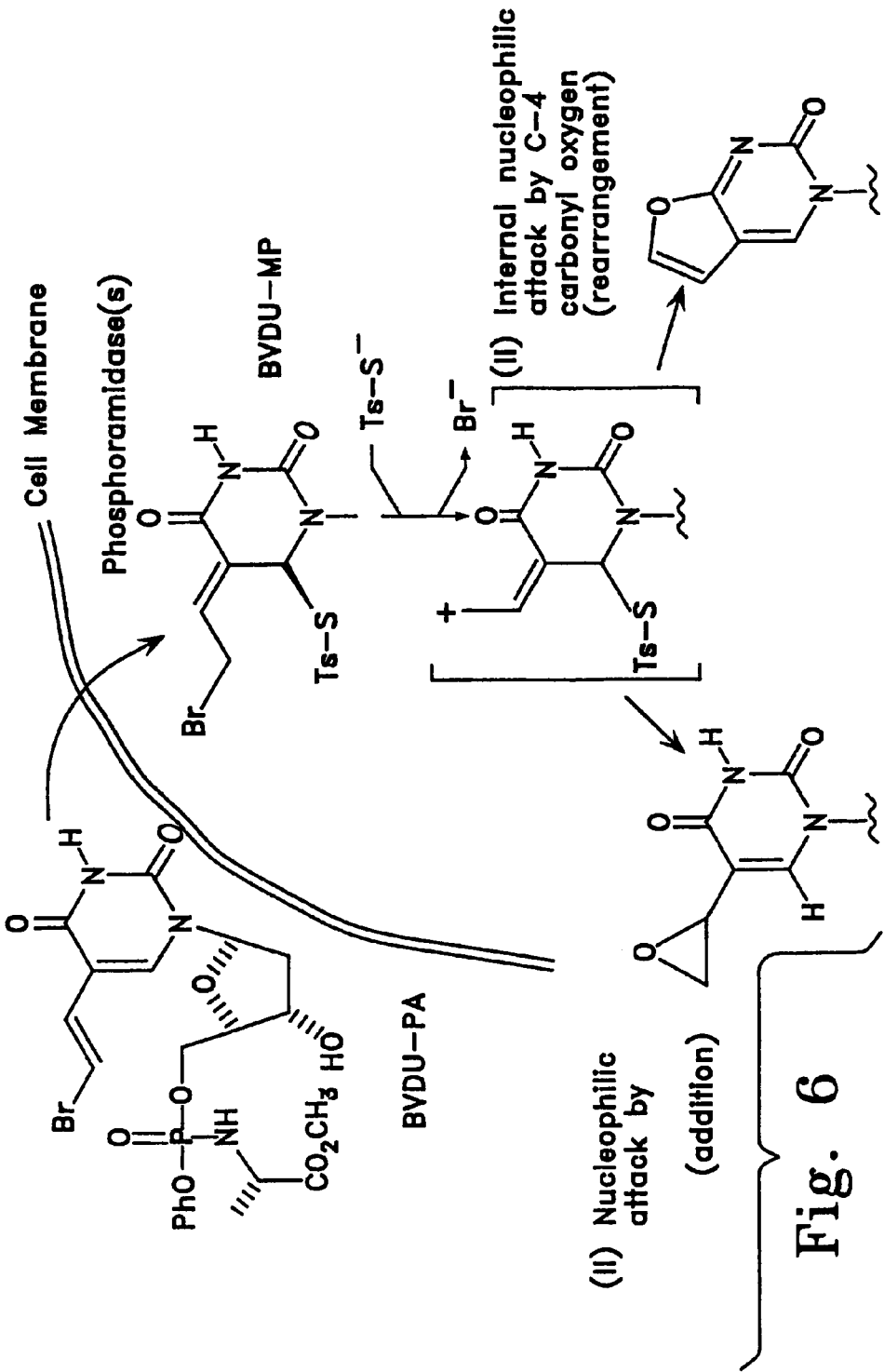
FIG. 6 is a proposed mechanism of NB1011 activation. NB1011 must be able to enter cells and convert to BVdUMP before interacting with TS. Structures generated following transformation by TS are proposed to be exocyclic pyrimidine nucleotide monophosphates. These compounds may be cytotoxic to cells by a variety of mechanisms including interference with nucleotide and nucleic acid metabolism.

The nature of and basic approaches to cancer treatment are constantly changing. Much of this change is occurring as a result of a better understanding of the molecular basis of disease. Research in each of these new areas has led to experimental or, in some cases, routine applications for nonmalignant disease. The same drugs used for cytotoxic antitumor therapy have become important components of treatment regimens for rheumatoid arthritis (methotrexate and cyclophosphamide), organ transplantation (methotrexate and azathioprine), sickle cell anemia (hydroxyurea), anti-infective chemotherapy (trimetrexate and leucovorin), and psoriasis (methotrexate). Thus, a broad spectrum of medical, surgical, and pediatric specialists employ these drugs for both neoplastic and normeoplastic disease. Understanding of disease mechanisms has also led to a better means of deciding on drug combinations for treating disease, including cancer. For instance, it is now known that different chemotherapeutics work by distinct mechanisms, and that proper combinations can leads to synergistic effects. NB1011 appears to work via activation by thymidylate synthase, and the resulting aberrant nucleotides are proposed to interfere with multiple steps in nucleotide metabolism (FIG. 6). Combination with chemotherapeutics or biologics which work by distinct mechanisms should give enhanced or synergistic activity. Examples of such compounds include: 1) doxorubicin, which acts by multiple mechanisms including DNA intercalation and free radical formation; 2) the topoisomerase inhibitors, like topotecan, which induce single strand breaks in DNA during replication; 3) antihormones, including antiestrogens (e.g., Tamoxifen) or antiandrogens (eg., flutamide), or biologics, like inteferon (e.g., Intron A). In these latter cases the antihormones prevent growth stimulation by the cognate hormones; interferon, which induces a multitude of pathways including induction of intracellular nucleases and suppression of oncogene expression Synergy with NB1011 is also seen via use of alkylating agents, like nitrogen mustard, which modify and inactivate many cellular components, but most importantly modify DNA repair and apoptosis.

It is a further aspect of this invention to combine the prodrugs described herein with additional therapies as described above. For example, the prodrugs described herein are preferentially combined with drugs that exert their toxic effect by a means other that that of the invention prodrugs. Such additional therapeutic compounds include, but are not limited to; angiostatin, antiestrogens, and topoisomerase inhibitors. In addition, the prodrugs and methods of this invention can be combined with surgical or radiation therapy for total eradication of the tumor.

Various methods are available to determine if the object of the therapeutic method has been met. This include, but are not limited to RT-PCR analysis, growth inhibition study (alamar blue assay) and plaque assays. These methods are well known in the art and described herein.

Figure 14:
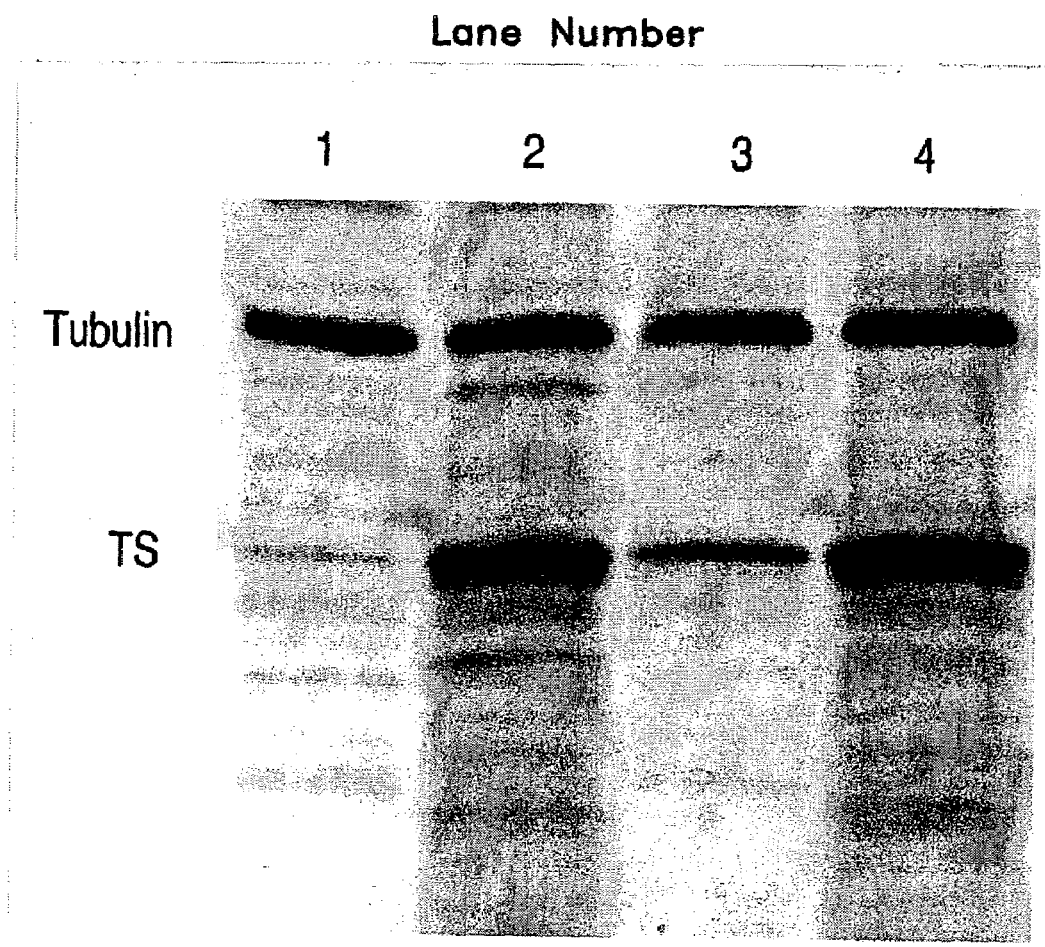
FIG. 14 shows TS expression level in cells selected with Tomudex or NB1011, as estimated by SDS PAGE Western blot developed with antibody against thymidylate synthase and tubilin. Lane 1 shows MCF7 cells, no selection with drug; lane 2 shows MCF7 cells selected with 2 µM tomudex; lane 3 shows MCF7 cells as in lane 2, but after a subsequent selection using NB1011 as the selective agent; lane 4 shows MCF7 cells as in lane 2, after a subsequent passaging without Tomudex.

Applicants also have discovered that cells which have been treated with the substrate prodrugs may revert to a prior phenotype which is suitably treated by conventional therapies. Using TS as an example, Applicants have shown that tumor cells treated with 5-FU became resistant to the drug. At that time, the cells were treated with NB1011. A subpopulation survived and became resistant to NB1011 but regained sensitivity to 5-FU (see Table 9 and FIG. 14). Thus, this invention provides the methods described above wherein an effective amount of another agent is co-administered with the substrate prodrug of this invention. In one aspect, the second or third agent is the drug to which the cell had previously developed resistance. The additional agent can be administered concurrently or subsequent to administration of the substrate prodrug.

This invention further provides prodrugs that are selectively converted by an activating enzyme overproduced or overexpressed by a pathological cell as compared to the counterpart normal cell, e.g., an animal cell, a mammalian cell, or a human cell. Applicants have discovered several preferential prodrugs for the practice of this invention. The structures and synthetic methods for these compounds are provided in Materials and Methods, below.

Another aspect of this invention is a method for treating a subject by administering to the subject a therapeutically effective amount of a prodrug that is selectively converted to a toxin in a cell by an activating enzyme as defined herein. In a further aspect, an effective amount of at least one additional therapeutic agent is co-administered concurrently or subsequently to administration of the substrate prodrug.

Screening Assays

This invention further provides a method for screening for prodrugs that are selectively converted to a toxin in a pathological cell by providing at least two test cells that express an activating enzyme and contacting the cells with a candidate prodrug. One then assays for activation of the prodrug into toxic agents by the enzyme. In one embodiment, the first test cell is a pathological cell, as defined above and the other test cell is the counterpart normal cell that expresses normal levels of the enzyme. In a further aspect, the candidate prodrugs are detectably labeled. In one embodiment, the detectable label is a fluorescent marker. In an additional embodiment, the detectable label is at least two or more variable isotopes of the same atom, e.g., bromine. In this embodiment, one can assay for the modification of the prodrug into toxic byproducts by mass spectrometry of the reaction products. The therapeutic potential of the candidate agents that have produced toxic metabolites are confirmed by purifying the toxic product and then separately assaying for its ability to selectively inhibit proliferation of a pathological cell and not producing discernible toxicity to normal cells. Further confirmation can be achieved by administration of the prodrug and toxic metabolite to an appropriate animal model as described above.

As used herein, the test cells can be procaryotic or eucaryotic cells that express the enzyme or alternatively, transformed to express the intracellular enzyme. For example, a procaryotic E. coli which does not endogenously express the intracellular enzyme TS is a suitable host cell or target cell. Transfection of the E. coli is carried out similar to that described for an eucaryotic cell, infra. Alternatively, the test cell can be pathological cell isolated from the subject, or a cultured cell that expresses the enzyme. The cell can have a control counterpart (lacking the target enzyme), or in a separate embodiment, a counterpart genetically modified to differentially express the target enzyme, or enzymes (expressing varying levels of target enzyme). More than one species of enzyme can be on a target enzyme can be simultaneously compared to its effect on another enzyme or a corresponding enzyme from another species.

In another embodiment, a third target cell is used as a positive control because it receives an effective amount of a compound, such as, for example, the compounds shown below, which have been shown to be potent prodrugs.

Ras-transformed NIH 3T3 cells (ATCC, 10801 University Blvd., Manassas, Va. 20110-2209, U.S.A.) are suitable eucaryotic cells. The cells are engineered to express variable and increasing quantities of the target enzyme of interest from cloned cDNA coding for the enzyme. Transfection is either transient or permanent using procedures well known in the art and described in Sambrook, et al., supra. Suitable vectors for insertion of the cDNA are commercially available from Stratagene, La Jolla, Calif. and other vendors. The level of expression of enzyme in each transfected cell line can be monitored by immunoblot and enzyme assay in cell lysates, using monoclonal or polyclonal antibody previously raised against the enzyme for immuno-detection. The amount of expression can be regulated by the number of copies of the expression cassette introduced into the cell or by varying promoter usage. Enzymatic assays to detect the amount of expressed enzyme also can be performed as reviewed by Carreras and Santi (1995), supra, or the methods described below.

The test cells can be grown in small multi-well plates and is used to detect the biologic activity of test prodrugs. For the purposes of this invention, the successful candidate drug will inhibit the growth of the pathological cell or kill it but leave the control cell type unharmed.

The candidate prodrug can be directly added to the cell culture media or previously conjugated to a ligand specific to a cell surface receptor and then added to the media Methods of conjugation for cell specific delivery are well known in the art, see e.g., U.S. Pat. Nos. 5,459,127; 5,264,618; and published patent specification WO 91/17424 (published Nov. 14, 1991). The leaving group of the candidate prodrug can be detectably labeled, e.g., with tritium. The target cell or the culture media is then assayed for the amount of label released from the candidate prodrug. Alternatively, cellular uptake may be enhanced by packaging the prodrug into liposomes using the methods well known in the art or combined with cytofectins, also as well known in the art.

It should be understood, although not always explicitly stated, each embodiment can be further modified by providing a separate target cell to act as a control by receiving an effective amount of a compound, such as, for example, the compounds shown below, which have been shown to be potent prodrugs.

Agents identified by this method are further provided herein.

Using the above screen, one also can pre-screening several prodrugs against samples taken from a subject such as a human patient. One can use the screen to determine the most effective substrate prodrug and therapy for each target enzyme and subject. This method is described in more detail, supra.

Prodrugs of This Invention

I. Materials and Methods

A. Synthetic Methodology.

(E)-(2-Bromovinyl)-2'-deoxyuridine (BVdU), was prepared by the method of Dyer, et al. (Dyer, et al. (1991) Nucleic Acid Chemistry: Improved and New Synthetic Procedures, Methods and Techniques, Townsend, et al. (eds) John Wiley & Sons, Inc., New York, pp. 79-83). This and commercial (Fisher/Acros) 5-fluoro-2'-deoxyuridine (5FdU) were each dried in vacuo at 75° C. adjacent to P2O5 immediately prior to use. Radial chromatography was performed on a Chromatotron instrument (Harrison Research, Palo Alto, Calif.), using Merck silica gel-60 with fluorescent indicator as adsorbent. (E)$_5$-(2-Bromovinyl)-2'-deoxyuridine 5'-monophosphate ("BVdUMP") was prepared by standard chemical phosphorylation of BVdU.

NMR 1H NMR spectra were recorded on a Varian Associates Gemini spectrometer at 300 MHz, using hexadeuteriodimethyl sulfoxide ($C^2H_3)_2$SO solutions. Chemical shifts are reported relative to internal tetramethylsilane reference at d=0.0 ppm. $^{13}$C NMR spectra were recorded at 75 MHz, with chemical shifts reported relative to internal pentadeuteriodimethyl sulfoxide at d=39.5 ppm. 31p NMR spectra were recorded at 202 MHz on a Bruker spectrometer, with chemical shifts reported relative to external 85% $H_2O$/15% $H_3PO_4$, vol/vol, at d=0.0 ppm.

NB1011 ((E)-5-(2-Bromovinyl)-2'-deoxy-5'-uridyl phenyl L-alaninylphosphoramidate (BVdU-PA, "NB1011")) was prepared as follows. A solution of BVdU (420 mg, 1.26 mmol) and imidazole (103 mg, 1.51 mmol) in 2 mL of anhydrous DMF under argon was treated dropwise with phenyl L-methoxyalaninyl phosphorochloridate (McGuigan, et al. (1996) J. Med. Chem. 39: 1748-1753 (15 drops, 350 mg, 1.26 mmol) and the reaction mixture was stirred at 23° C. under argon for 24 hours. By TLC on silica gel using 10% MeOH/ 90% $CH_2Cl_2$, vol/vol, as eluent, the generation of conversion product (R=0.70) from starting product ($R_f$=0.53) had occurred but only to a partial extent (ca. 15%), so additional imidazole (52 mg, 0.75 mmol) and phosphorochloridate reagent (8 drops, 175 mg, 0.63 mmol) was added and the mixture stirred at 23° C. under argon another 24 hours. By TLC, the conversion had increased to ca. a 30% extent. Subsequent treatment with additional phosphorochloridate and imidazole did little to promote the progress of the reaction. The solution was reduced in volume to 0.75 mL by rotary evaporation in vacuo at ≠40° C., and then an equal volume of $CH_2Cl_2$ was added and the solution was applied directly to a dry 4 mm silica gel Chromatotron plate. At this point, the subsequent separation was facilitated if the bulk of the remaining DMF was removed by placing the plate in a vacuum desiccator for 30 min. Radial chromatography using 250 mL of $CH_2Cl_2$ (to elute residual reagents and DMF) followed by 10% MeOH/90% $CH_2Cl_2$, vol/vol, (to elute the product and then the starting material) gave 144 mg (20%) of the intermediate (3) and 294 mg of starting material, for a 67% yield of conversion product based on unrecovered starting material. If the presence of contaminating imidazole (d=7.65 and 7.01) or DMF (d=7.95, 2.89, and 2.73) was detected by $^1$H NM, an additional radial chromatographic purification was performed. In this way, conversion product with a purity of =98% by TLC and 1H NMR was obtained as a nearly equimolar mixture of phosphorus center-based diastereomers, in oil/gum or foam-powder form: $^1$H NMR ($(C^2H_3)_2$SO) d=11.4 (bs, exchanges with $^2H_2O$, 1, N3H), 8.28 (pseudo-t, 1, H6), 7.35 (pseudo-t, 2, o-Ph), 7.31 (d, 1, vinyl $^1$H), 7.20 (pseudo-t, 3, m- and p-Ph), 6.89 (d, 1, vinyl 2H), 6.19 (t, 1, H1'), 6.08 (t, exchanges with 2$H_2O$, 1, alaninyl NH), 5.45 (bs, exchanges with 2$H_2O$, 1, O3'H), 4.32 (m, 1, H3'), 4.22 (m, 2, 5'CH2), 3.97 (m, 1, H4'), 3.86 (t, 1, alaninyl CH), 3.58 (two s, 3, $CO_2$Me), 2.15 (m, 2, 2'CH2), 1.23 (pseudo-t, 3, alaninyl CH3). Jvinyl CH-vinyl CH=13.5, JH1'-H2'~6.8, JH2'~H3'~5, JH3'~H4'~0, Jalaninyl CH-alaninyl NH ~6 Hz. Spectral assignments were confirmed by 1H/1H COSY 2D NMR analysis. $^{13}$C NMR($(C_2H_3)_2$SO)) d=173.7 and 173.6 (alaninyl $CO_2$), 162.1 and 161.6 (C2), 150.6, 150.5 (ipso-Ph), 149.2 (C4), 139.4 and 139.2 (C6), 129.8 and 129.6 (m-Ph), 124.7 (p-Ph), 120.3, 120.2 (o-Ph), 107.1 (vinyl C1), 87.5 (vinyl C2), 84.8 (C4'), 83.8 (C1'), 70.1 (C3'), 66.1 (C5'), 51.9 (alaninyl OMe), 49.7 (alaninyl α-H), 29.5 (C2'), 19.6 (alaninyl α-Me). 3JP-C4'=7.8, 2JP-C5=4.4, 2JP-ipso-Ph=6.5 Hz. 31P NMR d=3.99, 3.69. Low-resolution DCI ($NH_3$) mass: 593/591 ($MNH_4^+$), 576/574 ($MH^+$).

For convenience only, the structures of the prodrugs useful in the methods of this invention have been classified as Class I and Class II.

General Synthesis of Compounds of Class I

The L and D isomers of the compounds of Class I have the structure:

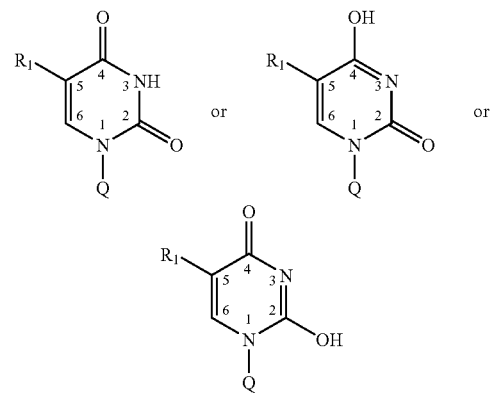

In the above formulae, $R_1$ (at the 5-position) is or contains a leaving group which is a chemical entity that has a molecular dimension and electrophilicity compatible with extraction from the pyrimidine ring and which upon release from the pyrimidine ring has the ability to inhibit the proliferation of the cell or kill the cell.

In the above formulae, Q is a sugar, carbocylic or acyclic compound, or a masked phosphate or phosphoramidate derivative thereof. A chemical entity selected from the group consisting of a sugar group, a thio-sugar group, Q is or contains a carbocyclic group, and derivatives thereof. Examples of sugar groups include, but are not limited to, monosaccharide cyclic sugar groups such as those derived from oxetanes (4-membered ring sugars), furanoses (5-membered ring sugars), and pyranoses (6-membered ring sugars). Examples of furanoses include threo-furanosyl (from threose, a four-carbon sugar); erythro-furanosyl (from erythrose, a four-carbon sugar); ribo-furanosyl (from ribose, a five-carbon sugar); arafuranosyl (also often referred to as arabino-furanosyl; from arabinose, a five-carbon sugar); xylo-furanosyl (from xylose, a five-carbon sugar); and lyxo-furanosyl (from lyxose, a five-carbon sugar). Examples of sugar group derivatives include "deoxy", "keto", and "dehydro" derivatives as well as substituted derivatives. Examples of thio sugar groups include the sulfur analogs of the above sugar groups, in which the ring oxygen has been replaced with a sulfur atom. Examples of carbocyclic groups include $C_4$ carbocyclic groups, $C_5$ carbocyclic groups, and $C_6$ carbocyclic groups which may further have one or more substituents, such as —OH groups.

In one embodiment, Q is a β-D-ribofuranosyl group of the formula:

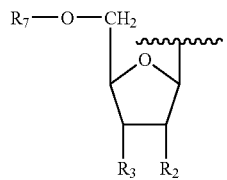

wherein $R_7$ is selected from the group consisting of H, a masked phosphate or a phosphoramidate and derivatives thereof, and wherein $R_2$ and $R_3$ are the same or different and are independently —H or —OH.

In some embodiments of the above formula, $R_1$ is an alkenyl group, i.e., (—CH═CH)$_n$—$R_4$, wherein n is 0 or an integer from 1 to 10, and $R_4$ is a halogen such as is I, Br, Cl, or CN or mercury. $R_2$ is H and $R_3$ is —OH or $R_2$ is OH and $R_3$ is H or $R_2$ and $R_3$ are H or wherein $R_2$ and $R_3$ are OH.

In another aspect, $R_4$ is or contains a group selected from the group consisting of H, alkyl, alkenyl, alkyl, hydroxy 1, —O-alkyl, —O-aryl, O-heteroaryl, —S-alkyl, —S-aryl, a cyanide, cyanate and thiocyanate halovinyl group, a halomercuric group, —S-heteroaryl, —NH$_2$, —NH-alkyl, —N(alkyl)$_2$, —NHCHO, —NHOH, —NHO-alkyl, NH$_2$CONHO—, and NHNH$_2$. In these embodiments, further aspects mclude: wherein $R_2$ and $R_3$ are H; wherein $R_2$ is OH and $R_3$ is H; herein $R_2$ is H and $R_3$ is OH; or wherein $R_2$ and $R_3$ are OH.

A preferred embodiment for the substituent in the $R_1$ position is one that could undergo an allylic interchange.

In a still further aspect, the candidate therapeutic agent is a compound of the formula:

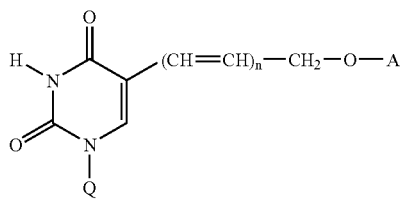

wherein n is an integer from 0 to 10; wherein A is a phosphorous derivative, or a compound of the formula:

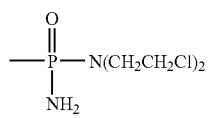

and wherein Q is selected from the group consisting of H, an unsubstituted or substituted sugar as defined above and a substituted or unsubstituted carbocyclic as defined above.

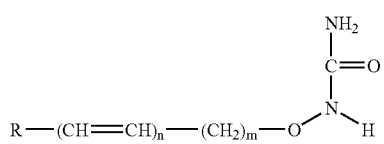

where R=2'-deoxy-5-uridyl, m is 0 or 1, and n is an integer from 0 to 10.

Where appropriate, the compounds can be in any of their enantiomeric, diastereomeric, or stereoisomeric forms, including, for example, D- or L-forms, and can be in any stereochemical configuration, including, for example, α- or β-anomeric form.

Synthesis of the above noted 5-substituted pyrimidine nucleosides and 5-substituted pyrimidine nucleoside monophosphates can be accomplished by methods that are well-known in the art. For example, treatment of 5-chloromercuri-2'-deoxyuridine with haloalkyl compounds, haloacetates or haloalkenes in the presence of Li$_2$PdCl$_4$ results in the formation, through an organopalladium intermediate, of the 5-alkyl, 5-acetyl or 5-alkene derivative, respectively. Another example of C5-modification of pyrimidine nucleosides and nucleotides is the formation of C5-trans-styryl derivatives by treatment of unprotected nucleotide with mercuric acetate followed by addition of styrene or ring-substituted styrenes in the presence of Li$_2$PdCl$_4$. Bigge, et al. (1980) J. Am. Chem. Soc. 102(6): 2033-2038. Pyrimidine deoxyribonucleoside triphosphates were derivatized with mercury at the 5 position of the pyrimidine ring by treatment with mercuric acetate in acetate buffer at 50° for 3 hours. Dale, et al. (1973) PNAS 70(8): 238-2242. Such treatment would also be expected to be effective for modification of monophosphates; alternatively, a modified triphosphate could be converted enzymatically to a modified monophosphate, for example, by controlled treatment with alkaline phosphatase followed by purification of monophosphate. Other moieties, organic or nonorganic, with molecular properties similar to mercury but with preferred pharmacological properties could be substituted. For general methods for synthesis of substituted pyrimidines, for example, U.S. Pat. Nos. 4,247,544; 4,267,171; and 4,948,882; and Bergstrom, et al. (1981) J. Org. Chem. 46(7):1432-1441. The above methods would also be applicable to the synthesis of derivatives of 5-substituted pyrimidine nucleosides and nucleotides containing sugars other than ribose or 2'-deoxyribose, for example 2'-3'-dideoxyribose, arabinose, furanose, lyxose, pentose, hexose, heptose, and pyranose. An example of a 5-position substituent is the halovinyl group, e.g. E-5-(2-bromovinyl)-2'-deoxyuridylate. Barr, et al. (1983) supra. For the purposes of this application, synthesis of two embodiments of the above formula were synthesized as described below.

Alternatively, 5-bromodeoxyuridine, 5-iododeoxyuridine, and their monophosphate derivatives are available commercially from Glen Research, Sterling, Va. (USA), Sigma-Aldrich Corporation, St. Louis, Mo. (USA), Moravek Biochemicals, Inc., Brea, Calif. (USA), ICN, Costa Mesa, Calif. (USA) and New England Nuclear, Boston, Mass. (USA). Commercially-available 5-bromodeoxyuridine and 5-iododeoxyuridine can be converted to their monophosphates either chemically or enzymatically, though the action of a kinase enzyme using commercial available reagents from Glen Research, Sterling, Va. (USA) and ICN, Costa Mesa, Calif. (USA). These halogen derivatives could be combined with other substituents to create novel and more potent antimetabolites.

General Synthesis of Compounds of Class II

The Compounds of Class II involves four classes of compounds. Each class is defined by the structure of the uricil base, or a modified uricil base. These classes are ECTA compounds where: I) the base is a furano-pyrimidinone derivative of uracil; II) the base is 6-fluoro uracil; and III) the base is 4-hydrazone substituted uracil derivative and IV) the base is uracil. The uracil or modified uracil derived base is used to synthesize compounds substituted with toxic leaving groups at the 5 position, attached by an electron conduit tether at this 5-position, and including an appropriate spacer moiety between the electron conduit and the toxic leaving group. The ECTA compounds contain a "Q" that can be unphosphorylated, 5' monophosphate, 5' phosphodiester, or 5' protected ("masked") deoxyuridines or comparable derivatives of alternative carbohydrate moieties at the $R^7$ position and as described below. Protected 5-substituted deoxyuridine monophosphate derivatives are those in which the phosphate moiety has been blocked through the attachment of suitable chemical protecting groups. Protection of 5-substituted deoxyuridine monophosphate derivatives can improve solubility, facilitate cellular penetration, facilitate passage across the blood-brain barrier, and prevent action of cellular or extracellular phosphatases, which might otherwise result in loss of the phosphate group. In another embodiment, 5-substituted uracil or uridine derivatives are administered to cells containing nucleoside kinase activity, wherein the 5-substituted uracil/uridine derivative is converted to a 5-substituted uridine monophosphate derivative. Uridine derivatives may also be modified to increase their solubility, cell penetration, and/or ability to cross the blood-brain barrier.

Action of thymidylate synthase upon 5-substituted uridine monophosphate derivatives can release the substituent attached to the 5-position ("leaving group") of the pyrimidine ring. The released substituent is then capable, either inherently or following reaction with another cellular component, of acting as a toxin or an inhibitor of cellular proliferation.

The L and D isomers of the compounds of this invention are selected from the group consisting of the compounds having the structures shown below:

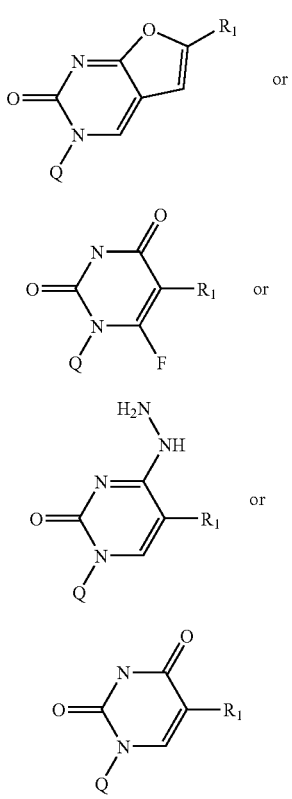

In the above formulae, $R^1$ is a moiety of the formula:

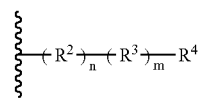

In the above formulae, $R^2$ is or contains a divalent electron conduit moiety. In one embodiment, $R^2$ is or contains a mono- or polyunsaturated electron conduit acting to conduct electrons away from the pyrimidine ring and toward the leaving group $R^1$ with the proviso that in compounds of class I, n can be zero. In one embodiment, $R^2$ is selected from the group consisting of: an unsaturated hydrocarbyl group; an aromatic hydrocarbyl group comprising one or more unsaturated hydrocarbyl groups; and, a heteroaromatic group comprising one or more unsaturated hydrocarbyl groups.

In one embodiment, MISO and $R^2$ is an unsaturated hydrocarbyl group having a structure selected from the group consisting of:

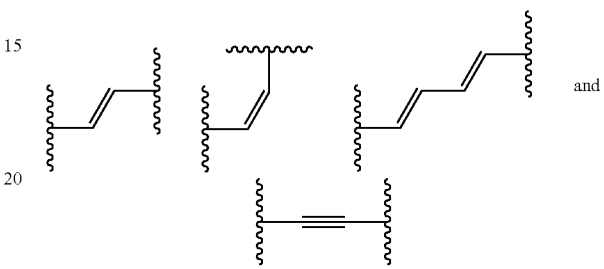

In one embodiment, $R^2$ and $R^3$, taken together form a structure selected from the group consisting of:

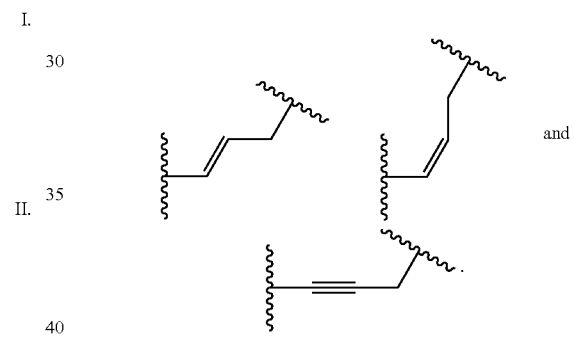

In one embodiment, $R^2$ is an aromatic hydrocarbyl group having a structure selected from the group consisting of:

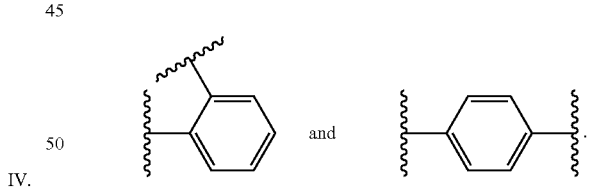

In one embodiment, $R^2$ is a heteroaromatic group having a structure selected from the group consisting of:

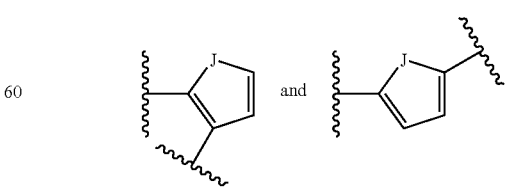

wherein J is a heteroatom, such as —O—, —S—, or —Se—, or a heteroatom group, such as —NH— or —NR$^{ALK}$-, where R$^{ALK}$ is a linear or branched alkyl having 1 to 10 carbon atoms or a cycloalkyl group having 3 to 10 carbon atoms.

In the above formulae, R$^3$ is a divalent spacer moiety, also referred to as a spacer unit. In one embodiment, R$^3$ is a divalent spacer moiety having a structure selected from the group consisting of:

R$^3$

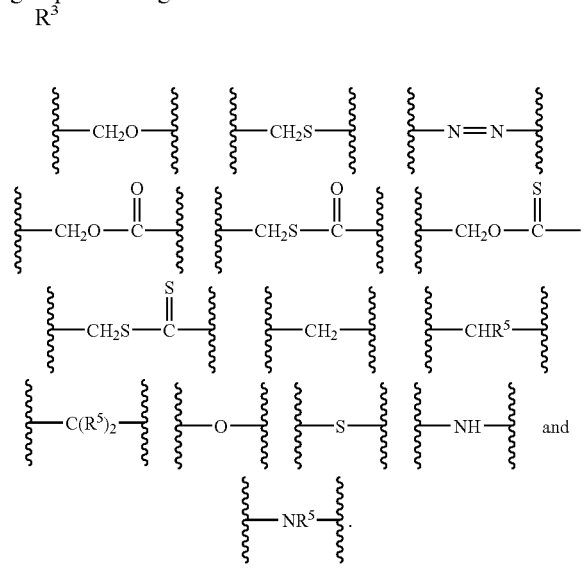

wherein R$^5$ is the same or different and is independently a linear or branched alkyl group having from 1 to 10 carbon atoms, or a cycloalkyl group having from 3 to 10 carbon atoms or R$^5$ is a halogen (F, Cl, Br, I).

In one embodiment, R$^3$ is a divalent spacer moiety having a structure selected from the group consisting of:

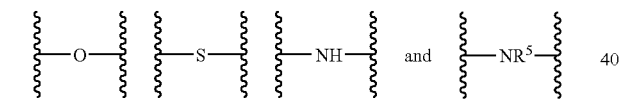

In one embodiment, R$^3$ is a divalent spacer moiety having a structure selected from the group consisting of:

R$^3$

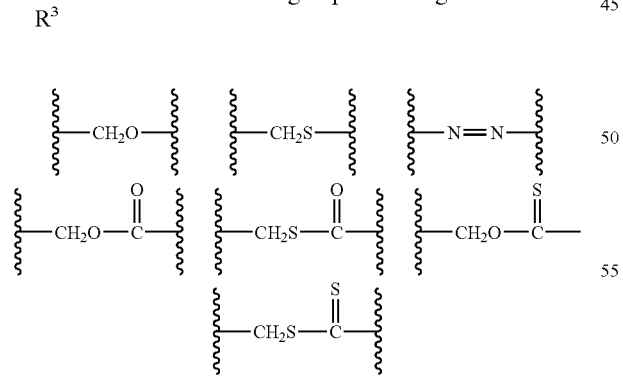

In the above formula, n is 0 or an integer from 1 to 10 and, m is 0 or 1. In one embodiment, n is 0 or an integer from 1 to 10 and, m is 1. In one embodiment, n is 0 and m is 0. In one embodiment, when R$^7$ is —H, then n is not zero. In one embodiment, when R$^7$ is —H, then m is not zero. In one embodiment, when R$^7$ is —H, then n is not zero and m is not zero. In one embodiment, when R$^7$ is —H, then R$^4$ is not a halogen (i.e., —F, —Cl, —Br, —I). In one embodiment, when R$^7$ is —H, and m is zero, then R$^4$ is not a halogen (i.e., —F, —Cl, —Br, —I). In one embodiment, when R$^7$ is —H, and m is zero and n is zero, then R$^4$ is not a halogen (i.e., —F, —Cl, —Br, —I).

In the above formula, R$^4$ is a toxophore moiety. As used herein, the term "toxophore" shall mean a moiety which is or contains a leaving group which is a chemical entity that has a molecular dimension and electrophilicity compatible with extraction from the pyrimidine ring by the activating enzyme, and which upon release from the pyrimidine ring by the enzyme, has the ability to inhibit the proliferation of the cell or kill the cell.

In one embodiment, the toxophore is or contains a leaving group that is activated or released by an intracellular enzyme overexpressed in the cell. In one embodiment, R$^4$ is or contains a group having a structure selected from the group consisting of:

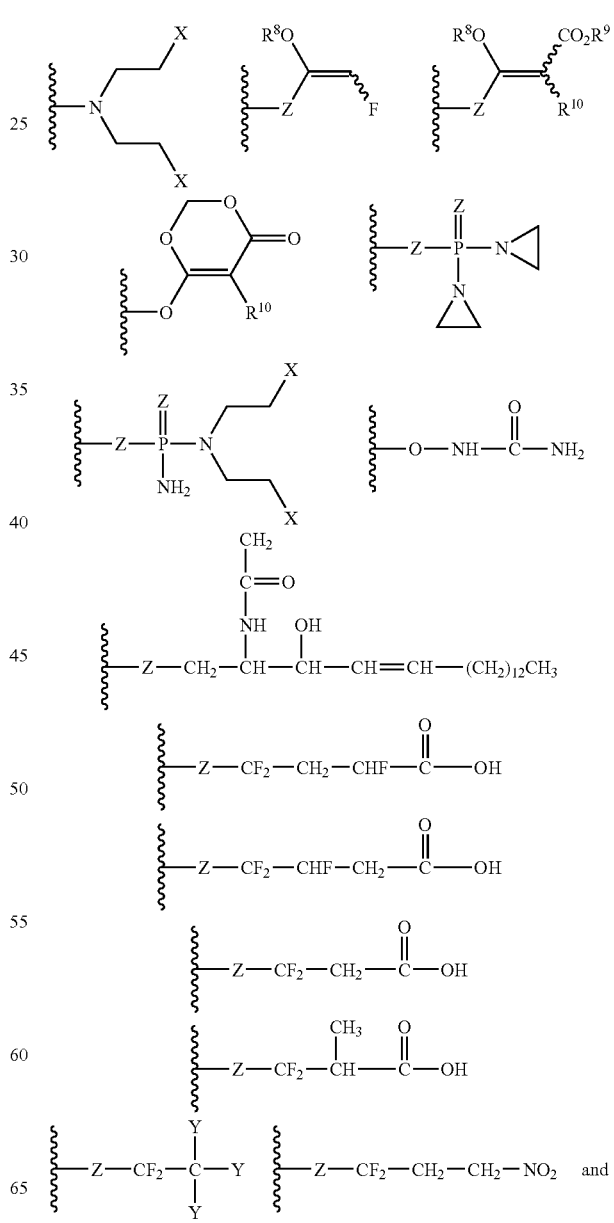

-continued

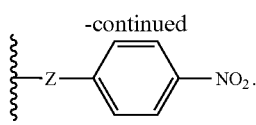

wherein X is the same or different at each position and —Cl, —Br, —I, or other potent leaving group (including, but not limited to, —CN, —OCN, and —SCN); Y is the same or different at each position, and is independently —H or —F; and Z is the same or different and is independently —O— or —S—, $R^8$ and $R^9$ are lower alkyls, and $R^{10}$ is H or $CH_3$.

In one embodiment, $R^4$ is or contains a chemical entity selected from the group consisting of: —Br, —I, —O-alkyl, —O-aryl, O-heteroaryl, —S-alkyl, —S-aryl, —S-heteroaryl, —CN, —OCN, —SCN, —$NH_2$, —NH-alkyl, —N(alkyl)$_2$, —NHCHO, —NHOH, —NHO-alkyl, $NH_2CONHO$—, $NHNH_2$, —$N_3$, and a derivative of cis-platin, such as:

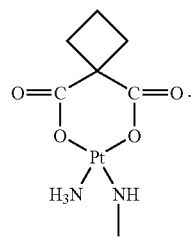

In the above formulae, Q is as described for the compounds of Class I and therefore is or contains a moiety which supports functional binding of the prodrug to the enzyme, e.g., TS or TK. In one embodiment, Q is selected from the group consisting of:

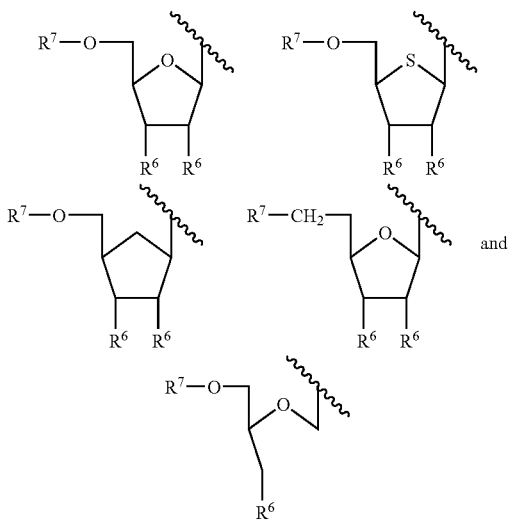

wherein $R^6$ is the same or different at each position and is independently —H, F, —OH, —OC(=O)$CH_3$, or other protected hydroxyl group (including, but not limited to, benzoyl, —$COC6H_5$, and toluoyl, —$COC_6H_4CH_3$); and, $R^7$ is attached to Q at the 5' position and is hydrogen, a phosphate group, a phosphodiester group, a phosphoramidate group, or other phosphorus containing group.

In one embodiment, Q is:

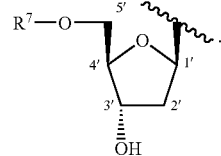

In one embodiment, $R^7$ is hydrogen. In an alternate embodiment, $R^7$ is a phosphate group, a masked phosphate group, a phosphodiester group, or a phosphoramidate group. In a preferred embodiment, $R^7$ is a phosphoramidate group.

In one embodiment, $R^7$ is a phosphoramidate group derived from an amino acid, including, for example, the twenty naturally occurring amino acids. In one embodiment, $R^7$ is a phosphoramidate group derived from alanine. In one embodiment, $R^7$ is or contains a group having the structure:

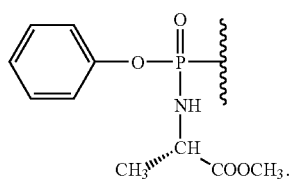

The above group, and methods for its preparation, are described in (McGuigan, et al. (1993) J. Med. Chem. 36: 1048-1052), and (McGuigan, et al. (1996) J. Med. Chem. 39: 1748-1753).

In one embodiment, $R^7$ is a phosphoramidate group derived from tryptophan. In one embodiment, $R^7$ is or contains a group having the structure:

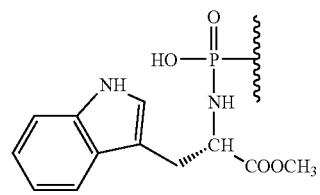

The above group, and methods for its preparation, are described in Abraham, et al. (1996) J. Med. Chem. 39: 4569-4575.

In one embodiment, $R^7$ is a phosphate group. In one embodiment, $R^7$ is or contains a group having a structure selected from the group consisting of:

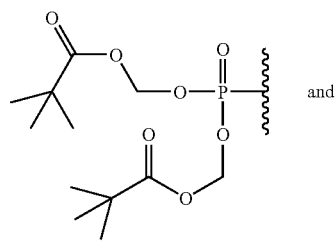

-continued

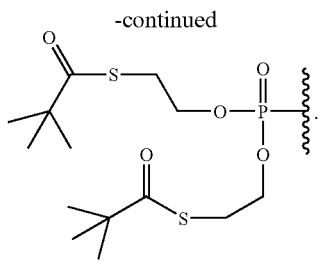

The first of the two above groups, and methods for its preparation, are described in Freed, et al. (1989) Biochem. Pharmacol. 38: 3193-3198; Sastry, et al. (1992) Mol. Pharmacol. 41: 441-445; Arquhar, et al. (1994) J. Med. Chem. 37: 3902-3909 and Farquhar, et al. (1995) J. Med. Chem. 38: 448-495. The second of the two above groups, and methods for its preparation, are described in Valette, et al. (1996) J. Med. Chem. 39: 1981 and Benzaria, et al. (1996) J. Med. Chem. 39, p. 4958.

In one embodiment, $R^7$ is or contains a group having a structure selected from the group consisting of (where R is an aromatic substituent):

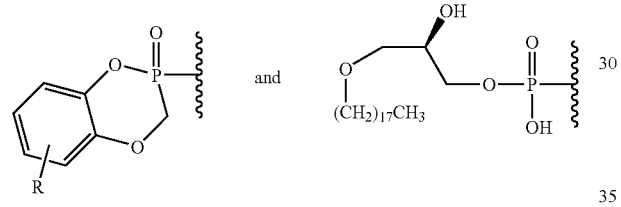

The first of the two above groups, and methods for its preparation, are described in Meier, et al. (1997) Bioorg. Med. Chem. Lett. 7: 1577; Meier, et al. (1997) Bioorg. Med. Chem. Lett 7: 99; and Meier, et al., (1997) International Antiviral News. 5: 183. The second of the two above groups, and methods for its preparation, are described in Hostetler, et al. (1997) Biochem. Pharmacol. 53: 1815; and Hostetler, et al., published International Patent Application No. WO 96/40088 (1996).

In one embodiment, the $R^7$ forms a cyclic group within Q. One such embodiment, and a method for its preparation, is shown below (where DMTr is 4,4'-dimethoxytrityl, Boc is t-butyloxycarbonyl, DCC is 1,3-dicyclohexylcarbodiimide, and 4-DMAP is 4-dimethylaminopyridine):

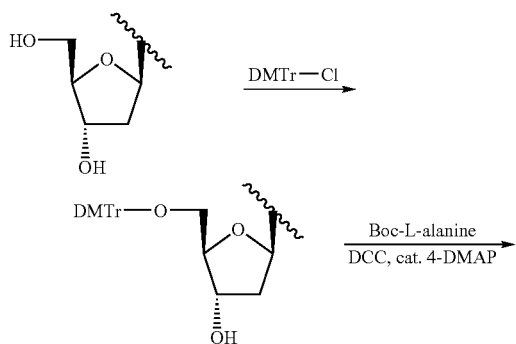

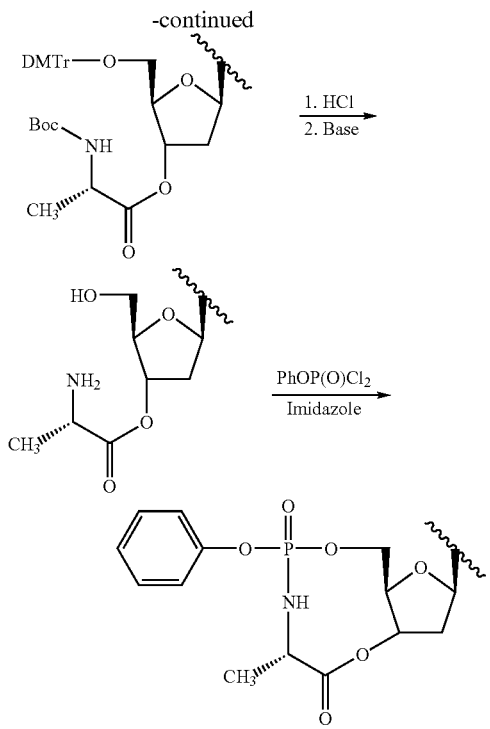

In one embodiment, the compound may be in any enantiomeric, diasteriomeric, or stereoisomeric form, including, D-form, L-form, α-anomeric form, and β-anomeric form.

In one embodiment, the compound may be in a salt form, or in a protected or prodrug form, or a combination thereof, for example, as a salt, an ether, or an ester.

In a separate embodiment, the above structures are further modified to possess thiophosphodiaziridine instead of phosphodiaziridine groups, using the methods described below.

The structures at the 5-position of uracil are referred to as the tethers because they connect the proposed leaving group (toxophore) to the heterocycle. Upon activation of the heterocycle by reaction with a Cys residue in for example, the active site of human TS, a negative charge is conducted from the 6-position of uracil into the tether. This mechanism has been described for the 5'-monophosphorylated versions of (BVDU) by (Barr, et al. (1983) Biochemistry 22: 1696-1703) and of (E)-5-(3,3,3-trifluoro-1-propenyl)-2'-deoxyuridine (TFPe-dUrd) by Wataya, et al. (1979) J. Med. Chem. 22: 339-340; Santi, (1980) J. Med. Chem. 23: 103-111; and Bergstrom, et al. (1984) J. Med. Chem. 27: 279-284.

The tether "spacer" between the toxin and dNMP must be unsaturated so that it can conduct the toxin-labilizing negative charge supplied by the TS-Cys-sulfhydryl attack. Of the many unsaturated organic functionalities available for this purpose, the vinyl, allyl, and propargyl units are simple, small, and readily accessible synthetically. The vinyl and allyl units have the advantage that they can be prepared in either of two non-interconvertible geometric isomeric forms. Thus, they can be used as "probes" of prodrug accommodation by the TS active site. On the other hand, the propargyl unit has the advantage of being cylindrically symmetrical, so that TS-catalyzed toxin release from this type of tether does not depend upon its orientation with respect to dUMP's uracil ring, as is the case with the vinyl and allyl molecules.

Two distinct approaches have been taken to design the nucleotide-based prodrugs of this invention. One is based on the structure of BVDU monophosphate and features a leaving group/toxin directly attached to the terminus of a (poly)vinyl substituent at CS of dUMP. This is the vinyl tether approach. The other is based on the structure of TFPe-dUMP and is similar to the first but has a methylene unit separating the leaving group/toxin and the unsaturated unit and thus contains an allyl or propargyl unit. This is the allyl tether approach.

The mechanism of activation of a propargyl version of the allyl tether approach has a precedent in the interaction of both 5-ethynyl-2'-deoxyuridine 5'-monophosphate (EdUMP) and 5-(3-hydroxy-1-propynyl)-2'deoxyuridine 5'-monophosphate (HOPdUMP) with TS (Barr, et al. (1981) J. Med. Chem. 24: 1385-1388 and Barr, et al. (1983) supra. EdUMP is a potent inhibitor of TS (Ki=0.1 TM), and likely forms an allene-based species at the active site. HOPdUMP (Ki=3.0 TM) shows unusual inhibition kinetics, which might be due to formation of a cumulene-based species at the active site.

5-Alkylidenated 5,6-dihydrouracils similar in structure to the intermediate common to both the vinyl and allyl tether approach mechanisms have been synthesized recently (Anglada, et al. (1996) J. Heterocyclic Chem. 33(4): 1259). These were shown to be highly electrophilic. Their ready reaction with ethanol to generate 5-(ethoxymethyl)uracils is a precedent for the water addition that regenerates catalytically competent TS. Even more recently, the existence of the long-elusive C5 methylene intermediate produced by TS was demonstrated by trapping studies (Barrett, et al. (1998) J. Am. Chem. Soc. 120: 449-450).

Synthesis of ECTA compounds with propargyl tethers. The synthesis of propargylic and allylic alcohol-equipped 2'-deoxyuridines is straightforward. Many of these and their close derivatives are reported in the literature, and some have even been studied in connection with TS. For example, 5-alkynyl-dUMPs including the 5-(3-methoxy-1-propynyl) and 5-(3-hydroxy-1-propynyl) ones have been examined as TS inhibitors (Barr, et al. (1981) J. Med. Chem. 24: 1385-1388) and some of these have been shown to become incorporated into the DNA of TS-deficient cancer cells (Balzai, et al. (1985) FEBS Lett 373(1): 41-4).

Both 5-mercuri—(Ruth, et al. (1978) J. Org. Chem. 43: 2870-2876) and 5-iodouridines (Robins, et al. (1981) Tetrahedron Lett 22:421-424) readily condense with alkenes and alkynes in the presence of a palladium catalyst to afford C5 tether-equipped uridines. The latter route is the more often employed (Robins, et al. (1982) Can. J. Chem. 60: 554-557; Asakura (1988) Tetrahedron Lett. 29: 2855-2858; and Asakura (1990) J. Org. Chem. 55: 4928-4933). High-yielding condensations of protected 5-iodo-2'-deoxyuridines with t-butyldimethylsilyl propargyl ether (Graham, et al. (1998) J. Med. Soc. Perk. Trans. 1: 1131-1138 and De Clercq, et al. (1983) J. Med. Chem. 26: 661-666), methyl propargyl ether (Tolstikov, et al. (1997) Nucleosides Nucleotides 16: 215-225) and even propargyl alcohol itself (Chaudhuri, et al. (1995) J. Am. Chem. Soc. 117: 10434-10442 and Goodwin, et al. (1993) Tetrahedron Lett. 34: 5549-5552) have been achieved. The 3-hydroxy-1-propynyl substituent introduced by the latter reaction can also be accessed by DIBAL-H reduction of a methacrylate group (Cho, et al. (1994) Tetrahedron Lett. 25: 1149-1152), itself arising from the same Heck reaction used in the synthesis of BVDU. These palladium-catalyzed reactions are so versatile that they can used to condense very long and elaborately-functionalized propargyl-based tethers to 5-iodo-2'-deoxyuridines (Livak, et al. (1992) Nucleic Acids Res. 20: 4831-4837 and Hobbs (1989) J. Org. Chem. 54: 3420-3422). (Z)-Allyl-based tethers are generated by the partial hydrogenation of a propargylic precursor over Undiar catalyst (Robins (1983) J. Org. Chem. 5(11): 3546-3548) and (Barr (1983) J. Biol. Chem. 258(22): 13627-13631 and Biochem. 22: 1696-1703) whereas the (E)-allyl-based ones are best prepared by Heck coupling of an (E)-tributylstannylated ethylene (Crisp (1989) Synth. Commun. 19: 2117-2123).

Closely following the literature procedures, a t-butyldimethylsilyl propargyl ether-equipped 3',5'-di-O-protected 2'-deoxyuridine (Graham, et al. (1998) supra; (De Clercq, et al. (1983) J. Med. Chem. 26: 661-666) is prepared and a portion of it, converted to the corresponding (Z)-allyl ether, (Barr, et al. (1983) supra) is reduced. Because the TBAF-mediated removal of a TBDMS group generates an oxyanion that can be functionalized in situ, these TBDMS-protected propargyl- and (Z)allytic-tethered nucleosides will serve as convenient precursors to some of the toxophore-equipped targets. For the (E)-allyl alcohol equipped nucleoside, the known O-tetrahydropyranyl ether derivative is prepared by the literature Heck coupling of an (E)-tributylstannylated ethylene (Crisp (1989) supra).

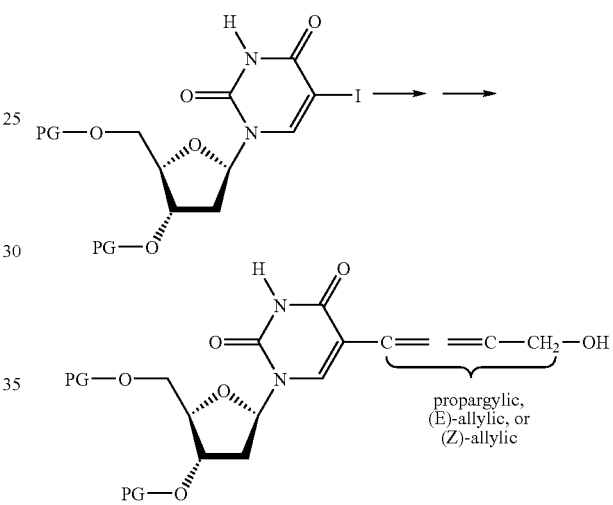

Using a two step literature protocol (Phelps, et al. (1980) J. Med. Chem. 23: 1229-1232 and Hsiao and Bardos (1981) J. Med. Chem. 24: 887-889), the propargylic and (E) and (Z)-allylic alcohols are converted to their corresponding bis-aziridinyl phosphoramidates or thiophosphoramidates so that TS processing of the 5'-mononucleotide versions will release an active metabolite of the cytostatic drugs TEPA or ThioTEPA (Dirven, et al. (1995) Cancer Res. 55: 1701-1706), respectively

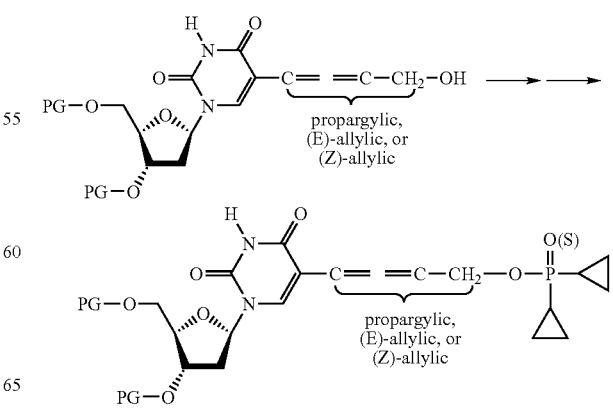

Bis-aziridin-1-yl-phosphinic acid 3-[2-deoxyuridin-5-yl]-prop-2-ynyl ester ("TEPA") was synthesized and analyzed by $^1$H NMR to yield the following result: $^1$H NMR((CD3)$_2$SO) complicated due to noise. Salient features: δ 8.28 (d, 1, H6), 6.10 (pseudo-t, 1, H1'), 5.26 (m, exchanges with D$_2$O, 1, 3'-OH), 5.13 (m, exchanges with D$_2$O, 1,5'-OH), 4.81 (q or dd, 2, propargyl-CH$_2$), 4.24 (m, 1, H3'), 3.57 (m, 2,5'-CH$_2$), 2.15-2.0 (m, 8, aziridine-CH$_2$).

Bis-aziridin-1-yl-phosphinothioic acid 3-[2-deoxyuridin-5-yl]-prop-2-ynyl ester ("ThioTEPA") was also synthesized and analyzed by $^1$H NMR to yield the following result:

$^1$H NMR((CD$_3$)$_2$SO) complicated due to noise. Salient features: δ 8.29 (d, 1, H6), 6.10 (pseudo-t, 1, H1'), 5.22 (m, exchanges with D$_2$O, 1,3'-OH), 5.10 (m, exchanges with D$_2$O, 1,5'-OH), 4.88 (q or dd, 2, propargyl-CH$_2$), 4.31 (m, 1, H3'), 3.52 (m, 2,5'-CH$_2$), 2.15-2.0 (m, 8, aziridine-CH$_2$).

Synthesis of furano-pyrimidinones. Synthesis of furano-pyrimidinones begins with synthesis of a C5 propargylic-alcohol-equipped 2'-deoxyuridine. Furano-pyrmidinone compounds are then be formed from the O-tetrahydropyranyl ether derivative described above. Synthesis proceeds by reaction of the second carbon of the propargyl bond with the oxygen attached to the C4 position of the pyrimidine ring to yield a fluorescent furano-pyrimidinone which can be readily separated from the reaction mix. Such compounds provide an additional basis for synthesis of ECTA compounds through various combinations of specific electron conduits, spacers and toxic leaving groups.

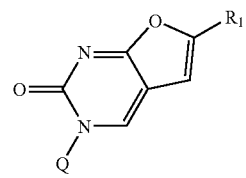

The furo [2,3-d]pyrimidinone nucleosides were prepared by condensing 2',3'-di-O-toluoyl or 2',3'-di-O-acetyl-5-iodo-2'-deoxyuridine with 1-(tetrahydropyranyloxy)-2-propyne (Jones and Mann (1953) J. Am. Chem. Soc. 75: 4048-4052) under conditions known to promote the formation of these fluorescent compounds (Barr, et al. (1983) supra). Base-catalyzed removal of the carbohydrate protecting groups gave the 6-(tetrahydropyran-2-yloxymethyl)-substituted bicyclic nucleoside which was either subjected to standard acidic THP group hydrolysis (TFA in CH$_2$Cl$_2$) or was regioselectively 5'-phosphoramidated by the same procedure used to prepare BvdU-PA and 5FUdR-PA. After the phosphoramidation, the THP group could be removed by acidic hydrolysis.

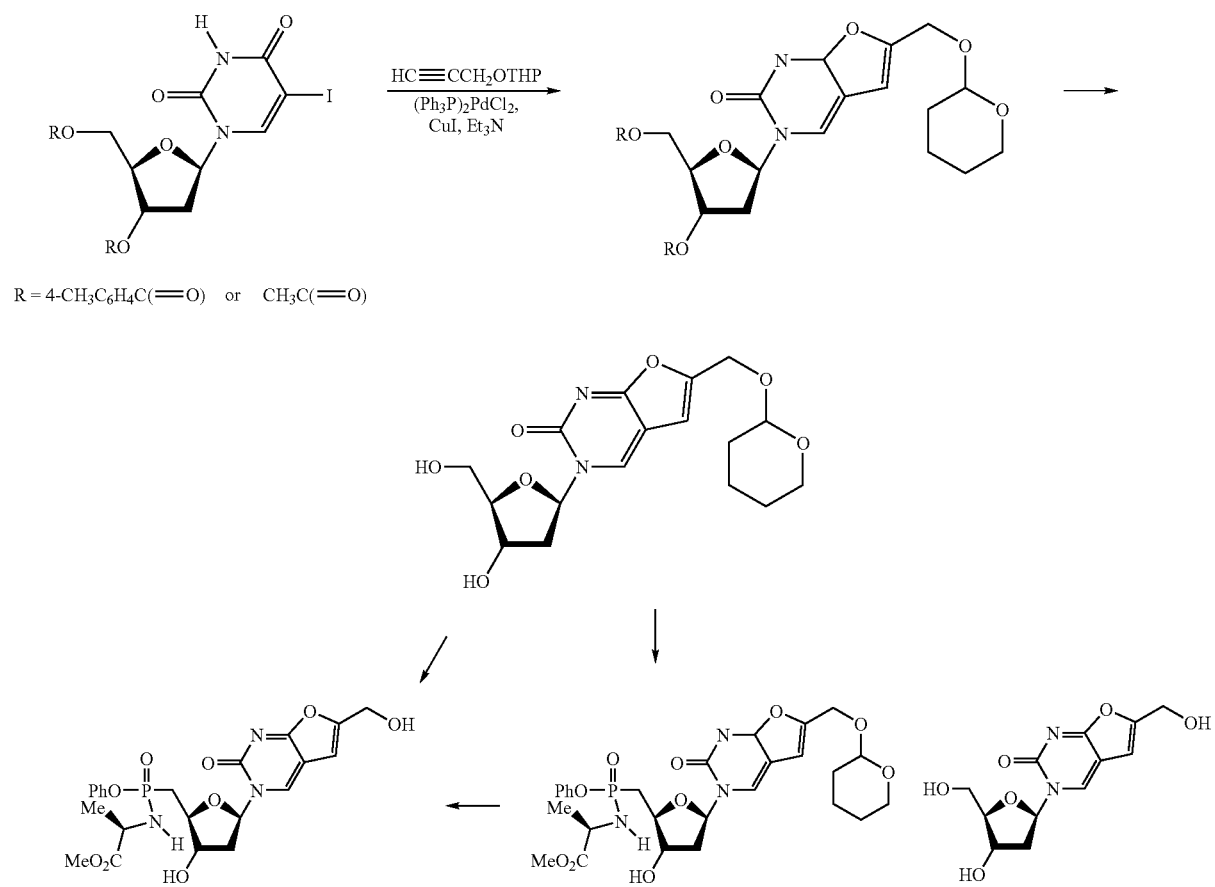

3-(2-Deoxy-β-D-ribofuranosyl)-6-(tetrahydropyran-2-yloxymethyl)furo[2,3-d]pyrimidin-2(3H)-one. $^1$H NMR ((CD$_3$)$_2$SO) δ8.80 (s, 1, H4), 6.74 (s, 1, H5), 6.16 (pseudo-t, 1, H1'), 5.27 (d, exchanges with D$_2$O, 1,3'-OH), 5.12 (t, exchanges with D$_2$O, 1,5'-OH), 4.72 (m, 1, THP-H2), 4.56 (q, 2, CH$_2$OTHP), 3.92 (m, 1, H4'), 3.64 (m, 2,5'-CH$_2$), 2.40 (m, 1, H2'a), 2.03 (m, 1, H2'b), 1.68 and 1.50 (m, 8, THP). Low-resolution mass spectrum (DCI-NH$_3$) on bis-TMS derivative, m/z 323 (B+TMS+H$^+$), 511 (MH$^+$), 583 (M+TMS$^+$).

3-(2-Deoxy-β-D-ribofuranosyl)-6-(hydroxymethyl)furo[2,3-d]pyrimidin-2(3H)-one. $^1$H NMR((CD$_3$)$_2$SO) δ 12.0 (bs, 1, OH), 8.24 (s, 1, H4), 6.53 (s, 1, H5), 5.51 (pseudo-t, 1, H1'), 4.42 (m, 2, CH$_2$OH). Low-resolution mass spectrum (DCI-NH$_3$), m/z 167 (B+2H$^+$), 184 (B+NH$_4^+$).

1-[6-(Tetrahydropyran-2-yloxymethyl)furo[2,3-d]pyrimidin-2(3H)-on-3-yl]-2-deoxy-β-D-ribofuranos-5-yl phenyl methoxy-L-alaninylphosphoramidate. 1H NMR ((CD3)$_2$SO) complicated due to presence of diastereomers. Salient features: δ 8.62 and 8.59 (each s, each 1, H4), 7.4-7.1 (m, 5, PhO), 6.61 and 6.60 (each s, each 1, H5), 6.25 (m, 1, H1'), 4.56 (q, 2, propargyl-CH$_2$), 3.56 and 3.54 (each s, each 3, CO$_2$Me), 2.0 (m, 1, H2'b), 1.22 (m, 3, alaninyl-α-Me). Low-resolution mass spectrum (DCI-NH$_3$), m/z 167 (B+2H$^+$), 184 (B+H$^+$+NH$_4^+$-THP).

1-[6(Hydroxymethyl)furo[2,3-d]pyrimidin-2(3H)-on-3-yl]-2-deoxy-β-D-ribofuranos-5-yl phenyl methoxy-L-alaninylphosphoramidate. $^1$H NMR (CDCl$_3$) complicated due to presence of diastereomers. Salient features: δ 8.5 (s, 1, H4), 7.4-7.1 (m, 5, PhO), 6.36 and 6.30 (each s, each 1, H5), 6.23 (m, 1, H1'), 3.67 and 3.65 (each s, each 3, CO$_2$Me), 2.69 (m, 1, H2'a), 2.10 (m, 1, H2'b), 1.35 (m, 3, alaninyl-a-Me). Low-resolution mass spectrum (DC$_1$—NH$_3$), m/z 525 (MH$^+$), 595 (MNH$_4^+$).

The 4-nitrophenyl ether derivative of 5-(3-hydroxy-1-propynyl)-2'-deoxyuridine was prepared according to a standard ether synthesis as shown below.

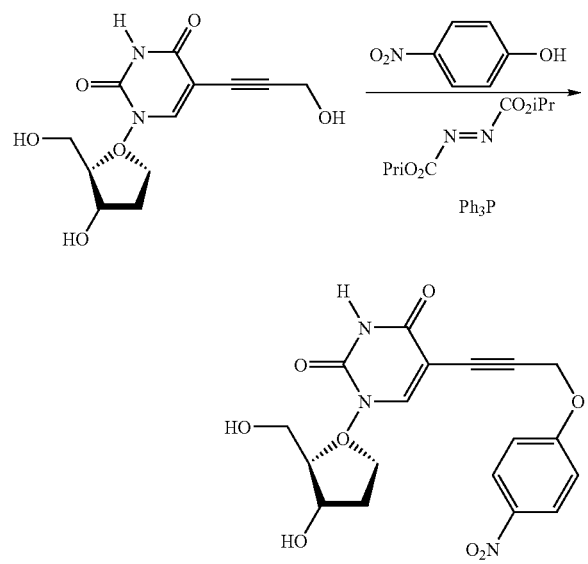

5-[3-(4-Nitrophenoxy)-1-propynyl]-2'-deoxyuridine. A solution of pre-dried 5-(3-hydroxy-1-propynyl)-2'-deoxyuridine ("Nucleic Acid Compounds. 39. Efficient Conversion of 5-Iodo to 5-Alkynyl and Derived 5-Substituted Uracil Bases and Nucleosides" Robins and Barr, (1983) supra) (565 mg, 2 mmol) in 40 mL of anhydrous THF under argon was treated with 4-nitrophenol (696 mg, 5 mmol), triphenylphosphine (787 mg, 3 mmol), and diisopropyl azodicarboxylate (590 L, 3 mmol), and the reaction mixture heated at 60° C. until the solution was clear, and then 1 h longer. The mixture was allowed to cool to 23° C. and then it was evaporated onto SiO$_2$ and purified by chromatography using MeOH/CH$_2$Cl$_2$ as eluent to afford 107 mg (13%) of the desired ether product: mp 112-118° C. $^1$H NMR((CD$_3$)$_2$SO) δ 11.65 (s, exchanges with D$_{2O}$, 1, NH), 8.29 (s, 1, H6), 8.24 (d, J=9.3 Hz, 2, m-ArH), 7.23 (d, J=9.3 Hz, 2, o-ArH), 6.09 (pseudo-t, 1, H1'), 5.17 (s, 2, propargyl-CH$_2$), 4.22 (m, 1, H3), 3.80 (m, 1, H4'), 3.59 (m, 2,5'-CH$_2$), 2.13 (pseudo-t, 2,2'-CH$_2$). Low-resolution mass spectrum (DCI-NH$_3$) on per-trimethylsilyated material, m/z 547 [M(TMS)$_2$H$^+$], 565 [M(TMS)$_2$NH$_4^+$], 620 [M(TMS)$_3$H$^+$].

TS ECTA compounds based on furano-pyrimidinones. Toxic R$^4$ leaving groups can be attached to the furan-2 methyl alcohol using methods similar to those employed to attach toxic leaving groups to the hydroxyl on the C5 propargyl uridine compound, as explained with the synthesis of the TEPA and ThioTEPA derivatives described above. A variety of alternative toxic leaving groups, apparent to one skilled in the art, are the subject of this invention. In addition, modifications to the length and composition of the R$^2$ electron conduit component and of the composition of the R$^3$ spacer element are also claimed.

TS ECTA compounds based on furano-pyrimidinones can also consist of variously modified "Q" moeities. Many 5-substituted 2'-deoxyuridines are not substrates for human TK, but interestingly 5-(4-hydroxy-1-butynyl)-2'-deoxyuridine was found to be an exception (Barr, et al. (1981) supra). Thus, it is expected that some of the toxophore equipped nucleosides will also possess propitious TK substrate activity. Thus, the ECTA compounds can have a free 5' hydroxyl, a 5' monophosphate, or a 5' phosphoramidate group attached to alternative carbohydrate groups. A novel method for synthesis of such phosphoramidate compounds is accomplished by reacting a 2-deoxy 3'-hydroxy, 5'-hydroxy unprotected nucleotide with a phosphochloridate in the presence of an HCl scavenger. In a preferred embodiment, the phosphochloridate comprises a phosphorus substituent which is derived from an amino acid such as alanine. For example, the phosphochloridate can be phenyl-L-methoxyalanine phosphorochloridate.

C6 Fluoro uridine and C4 hydrazone based compounds. The neutral thiol addition to the pyrimidine C5-C6 double bond proceeds as an exothermic reaction (3-9 kcal per mol; see review by Les, et al (1998) Biomolecular Structure and Dynamics 15(4): 703-715, in the normal TS reaction with dUMP. Alternative substituents to the TS reactive hydrogen at the 6 position that can facilitate the formation of the sulfdryl bond with the enzyme, via the active human TS cysteine (homologous with cys-198 of L. casei), include fluorine. Such substituents at other positions in the pyrimidine ring can also facilitate the reaction between the substrate and TS. For instance, a 4-hydrazone substitution on the uracil (as described by Les and Rhode. (1998) Biomolecular Structure and Dynamics 15(4): 703-715) facilitates formation of the thiol with TS. It is important that the resulting nucleotide-thiol (TS) intermediate rearranges in such a way as to release the altered nucleotide which can be accomplished passively via hydrolysis.

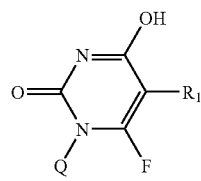

The introduction of fluorine at the C6 position has not been previously reported, but it can be synthesized by following the synthetic descriptions of Krajewskas and Shugar (1982) Biochem. Pharmacol. 31(6): 1097-102, who describe the synthesis of a number of 6 substituted uracil and uridine analogues.

Chemistry facilitating substitutions at the C4 position of the pyrimidine base are well known by those skilled in the art. Examples of literature descriptions include Wallis, et al. (1999) Farmaco 54(1-2): 83-89; Negishi, et al. (1996) Nucleic Acids Symp. Ser. 35 (Twentythird Symposium on Nucleic Acids Chemistry) 137-138; Barbato, et al. (1991) Nucleosides Nucleotides 10(4): 853-66; Barbato, et al. (1989) Nucleosides Nucleotides 8(4): 515-528; and Holy, et al. (1999) J. Med. Chem. 42(12): 2064-2086. These synthetic techniques also enable combinations of substitutions, for instance at the C4 and C5 positions of the pyrimidine ring (Pluta, et al. (1999) Boll. Chim. Farm. 138(1): 30-33) or the C2 and C4 positions of the pyrimidine ring (Zeid, et al. (1999) Nucleosides Nucleotides 18(1): 95-111).

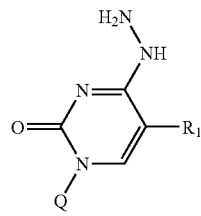

In another embodiment of the invention, ECTA compounds are synthesized by addition of alternative electron conduits, spacer moieties and toxic leaving groups to either the C6 fluoro-uridine base or the C4 hydrazone modified pyrimidine. Methods described above for synthesis of 2, deoxyuridine based ECTA compounds can again be employed for synthesis of such molecules.

B. Derivatives of the Compounds of Class I and II

Salts, esters, and ethers of the above compounds disclosed herein are also within the scope of this invention. Salts of the prodrugs of the present invention may be derived from inorganic or organic acids and bases. Examples of acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, can be employed in the preparation of salts useful as intermediates in obtaining the compounds of the invention and their pharmaceutically acceptable acid addition salts. Examples of bases include alkali metal (e.g., sodium) hydroxides, alkaline earth metal (e.g., magnesium) hydroxides, ammonia, and compounds of formula $NW_4^+$, wherein W is $C_{1-4}$ alkyl.

Examples of salts include: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylproprionate, picrate, pivalate, propionate, succinate, tartrate, thiocyanate, tosylate and undecanoate. Other examples of salts include anions of the compounds of the present invention compounded with a suitable cation such as $Na^+$, $NH_4^+$, and $NW_4^+$ (wherein W is a $C_{1-4}$ alkyl group).

For therapeutic use, salts of the compounds of the present invention will be pharmaceutically acceptable. However, salts of acids and bases which are non-pharmaceutically acceptable may also find use, for example, in the preparation or purification of a pharmaceutically acceptable compound.

Esters of the prodrugs or compounds identified by the method of this invention include carboxylic acid esters (i.e., —O—C(=O)R) obtained by esterification of the 2'-, 3'- and/or 5'-hydroxy groups, in which R is selected from (1) straight or branched chain alkyl (for example, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkylsulfonyl (for example, methanesulfonyl) or aralkylsulfonyl; (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di-($C_{6-24}$)acyl glycerol. In such esters, unless otherwise specified, any alkyl moiety present advantageously-contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group. Examples of lyxo-furanosyl prodrug derivatives of the present invention include, for example, those with chemically protected hydroxyl groups (e.g., with O-acetyl groups), such as 2'-O-acetyl-lyxo-furanosyl; 3'-O-acetyl-lyxo-furanosyl; 5'-O-acetyl-lyxo-furanosyl; 2',3'-di-O-acetyl-lyxo-furanosyl and 2',3',5'-tri-O-acetyl-lyxo-furanosyl.

Ethers of the compounds of the present invention include methyl, ethyl, propyl, butyl, isobutyl, and sec-butyl ethers.

In a further embodiment, the substrate may not be chemically related to pyrimidines or folates, but rather synthesized based upon known parameters of rational drug design. (See Dunn, et al. (1996) J. Med. Chem. 39: 4825).

Chemical assays for products, for example, where a reaction product is an anti-metabolite of the bromovinyl-derivatives of dUMP, are described in the Examples provided below or by (Barr, et al. (1983) supra).

C. Formulations

Formulations include those suitable for oral, recta, nasal, topical (including transdermal, buccal and sublingual), vaginal, parenteral (including subcutaneous, intramuscular, intravenous and intradermal) and pulmonary administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, past, gel, spray, aerosol or oil. Alternatively, a formulation may comprise a patch or a dressing such as a bandage or adhesive plaster impregnated with active ingredients and optionally one or more excipients or diluents.

For diseases of the eye or other external tissues, e.g., mouth and skin, the formulations are preferably applied as a topical ointment or cream containing the active ingredient in an amount of, for example, about 0.075 to about 20% w/w, preferably about 0.2 to about 25% w/w and most preferably about 0.5 to about 10% w/w. When formulated in an ointment, the prodrug may be employed with either a paraffinic or a water-miscible ointment base. Alternatively, the prodrug ingredients may be formulated in a cream with an oil-in-water cream base.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the prodrug ingredient through the skin or other affected areas. Examples of such dermal penetration enhancers include dimethylsulfoxide and related analogues.

The oily phase of the emulsions of this invention may be constituted from known ingredients in an known manner. While this phase may comprise merely an emulsifier (otherwise known as an emulgent), it desirably comprises a mixture of at lease one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the prodrug ingredient. The prodrug ingredient is preferably present in such formulation in a concentration of about 0.5 to about 20%, advantageously about 0.5 to about 10% particularly about 1.5% w/w.

Formulations for rectal administration may be presented as a suppository with a suitable base comprising, for example, cocoa butter or a salicylate.

Formulations suitable for vaginal administration may be presented as suppositories, tampons, creams, gels, pastes, foams or spray formulations containing in addition to the prodrug ingredient, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the prodrug ingredient.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of a prodrug ingredient.

It should be understood that in addition to the ingredients particularly mentioned above, the formulations of this invention may include other agents conventional in the art having regard to the type of formulation in question, for example, those suitable of oral administration may include such further agents as sweeteners, thickeners and flavoring agents.

Prodrugs and compositions of the formula of the present invention may also be presented for the use in the form of veterinary formulations, which may be prepared, for example, by methods that are conventional in the art."

Figure 13:
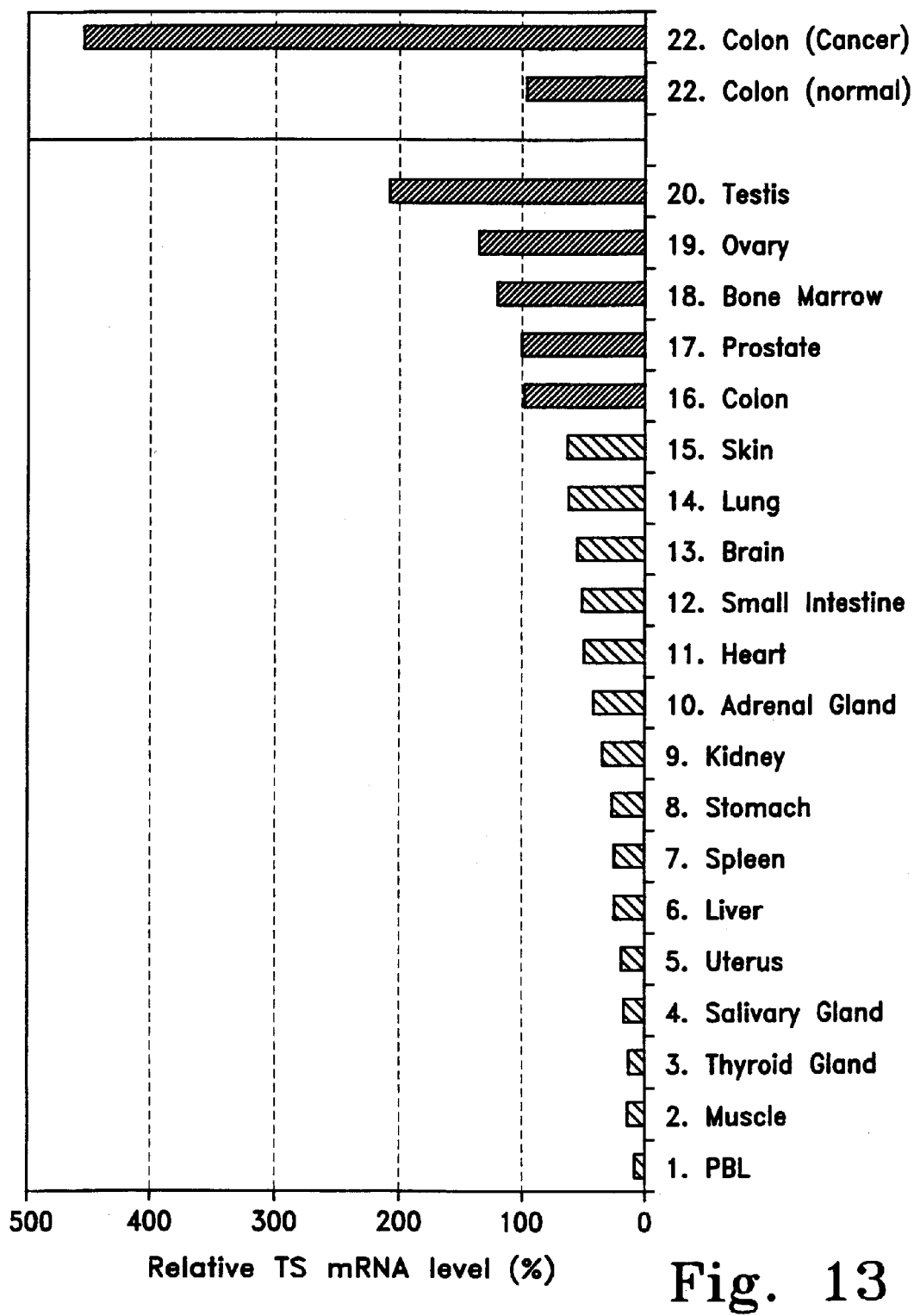
FIG. 13 is a graph showing mRNA levels of TS in multiple human tissues. TS mRNA levels were determined by using RT-PCR. The DNA bands corresponding to thymidylate synthase were quantified and normalized to that of β-actin by Molecular Dynamics Storm. Column 1 to 20 indicate the TS mRNA level in human normal tissues. The expression levels are expressed as values relative to that of colon (column 16). Columns 21 and 22 show the average TS transcript levels in 7 matched colon normal and cancer tissues. The expression values were relative to that of normal colon tissues (column 21).

D. Expression of thymidylate synthase in human normal tissues. The TS expression level in normal human tissues was examined in order to estimate the systemic toxicity of the prodrug which is activated by thymidylate synthase. The relative TS mRNA levels in brain, heart, kidney, spleen, liver, colon lung, small intestine, stomach muscle, testis, ovary, uterus, prostate, thyroid gland, salivary gland, adrenal gland, skin, PBL and bone marrow tissues were determined by using RT-PCR. It has been shown that TS mRNA levels in most of these tissues were equal to or less than that in colon tissue, except that in bone marrow (1.25 fold), ovary (1.38 fold) and testis tissues (2.13 fold) (FIG. 13). However, the average TS mRNA level in colon cancer samples was 4.6 fold more than that in their matched normal colon tissue samples. (FIG. 13). This result suggests that compounds which are activated by overexpressed TS in colon cancer would have no or little toxicity to normal human tissues.

Transcript levels of human thymidylate synthase in multiple normal tissues were investigated by PCR amplification. Panel of cDNAs of human tissues were obtained from Ori-Gene Technologics, Inc. (Rockville, Md.). PCR reactions were perfromed in a volume of 25 µl, containing cDNA (100×), 3 mM $MgCl_2$, 50 mM KCl 20 mM Tris-Cl, pH 8.4, 0.2 mM of each dNTP, 0.2 µM of thymidylate synthase sense and antisense primers and 1.25 units of Taq DNA polymerase (obtained from Promega, Madison, Wis.). The reaction mixtures were incubated at 94° C. for 2 min, followed by 12 cycles of 40 sec incubations at 94° C., 1 min incubation at 58° C., and then 1 min incubation at 72° C.25 ll reaction buffer contained 0.2 µM β-actin primers, 0.2 µM of thymidylate synthase primers, 3 mM $MgCl_2$, 50 mM KCl, 20 mM Tris-cl, pH 8.4, 0.2 mM of each dNTP and 1.25 units of Taq DNA polymerase were added to achieve a final concentration of 0.2 µM of thymidylate synthase primers and 0.1 µM β-actin primers, bringing the reaction volume to 50 µl. PCR reaction was continued to a total of 36 cycles, followed by a 7 min incubation at 72° C.

10 µL of PCR products were resolved by electrophoresis in a 2% agarose gel, followed by staining with SYBR Gold nucleic acid gel stain (obtained from Molecular probes, Eugene, Oreg.). The DNA bands corresponding to thymidylate synthase were quantified and normalized to that of β-actin by Molecular Dynamics Storm. The quantified expression levels were expressed as values relative to that of colon.

E. RT-PCR analysis of matched normal and human tissues. Transcript levels of human thymidylate synthase transcripts in colon cancer tissues and matched normal normal colong tissues were quantified by using RT-PCR. Oligonucleotide primers for amplification of the human thymidylate synthase and B-actin were designed as follows: thymidylate synthase sense primer (SEQ ID NO:1) 5'-GGGCAGATCCAACA-CATCC-3' (corresponding to bases 208-226 of thymidylate synthase cDNA sequence, Genbank Accession No. X02308), antisense primer (SEQ ID NO:2) 5'-GGTCAACTCCCT-GTCCTGAA-3' (corresponding to bases 564-583), β-actin sense primer (SEQ ID NO:3) 5'-GCCAACACAGTGCT-GTCTG-3' (corresponding to bases 2643-2661 of β-actin gene sequence, Genbank Accession No. M10277) and antisense primer (SEQ ID NO:4) 5'-CTCCTGCTTGCTGATC-CAC-3' (corresponding to bases 2937-2955).

Human colon tumor tissues and matched normal tissues were obtained from Cooperative Human Tissue Network (CHTN, Western Division, Cleveland, Ohio). Total RNAs were isolated using Tri pure isolation reagent (obtained from Boehringer Mannheim Corp., Indianapolis, Ind.), followed manufactureis protocol. To monitor for possible DNA contamination, the primers for amplification of β-actin were designed to span the exon4/intron5/exon5 junction. Genomic DNA template leads to a 313 bp P-actin fragment, and cDNA template generates a 210 bp product.

Reverse transcriptions were performed, using SuperScript preamplification system (Gibco/BRL, Gaithersburg, Md.). 3 µg total RNA was applied in a volume of 20 µl buffer to conduct reverse transcription reaction, followed manufacture's protocol.

PCR reactions were performed in a volume of 96 µl, containing 5 µl of cDNA mixture from reverse transcription reaction, 3 mM $MgCl_2$, 50 mM KCl, 20 mM Tris-Cl, pH 8.4, 0.2 mM of each dNTP, 0.3 µM of thymidylate synthase sense and antisense primers and 5 units of Tag DNA polymerase (obtained from Promega, Madison, Wis.). The reaction mixtures were incubated at 94° C. for 3 min, followed by 9 cycles of 1 min incubation at 94° C., 1 min incubation at 58° C., and then 1 min incubation at 72° C. After 9 cycles, human β-actin primers in 4 µl were added to achieve a final concentration of 0.2 µM, bringing the final reaction volume to 100 µl. PCR reaction was continued to a total of 30,32 or 34 cycles, followed by a 7 min incubation at 72° C.

10 µL of PCR products were resolved by electrophoresis in 2% agarose gel, followed by staining with SYBR Gold nucleic acid gel stain (obtained from Molecular probes, Eugene, Oreg.). Result of quantification indicated that amplification of thymidylate synthase and β-actin was linear between cycles 30 and 34. The DNA bands corresponding to thymidylate synthase were quantified and normalized to that of β-actin by Molecular Dynamics Storm. The quantified expression levels were expressed as values of ratio between TS and β-actin.

F. Cell lines and transfection. HT1080 cells were grown in PRMI1640 medium supplemented with 10% fetal calf serum, and transfected with GFP-TS expression vector. 48 hours after, transfection cells were tripsinized and replated in culture medium containing 750 µg/ml G418. After selection with G418 for two weeks, surviving cells were sorted based upon fluorescence expression. One clone with higher fluorescence expression (named as TSH/HT1080) and one clone with lower fluorescence expression (named as TSL/HT1080) were selected and expanded into cells lines. The stable HT1080 cells transfected with pEGFP-C3 were used as control.

G. Construction of GFP-TS expression vector. A cDNA fragment encoding conserved region of human thymidylate synthase (amino acids 23 to 313) was obtained by PCR amplification using following primers: Sense primer, (SEQ ID NO: 5) 5'-CGGAAGCTTGAGCCGCGTCCGCCGCA-3' and antisense primer, (SEQ ID NO: 6) 5'-GAAGGTAC-CCTAAACAGCCATTTCCA-3'. The cDNA was cloned into HindIII and KpnI sites of mammalian expression vector pEGFP-C3 (Clontech Laboratories, Inc., Palo Alto, Calif.), in-frame with GFP sequence. The cDNA insert was confirmed by DNA sequencing.

H. Western blot analysis. Human normal and cancer cells were grown in RPMI 1640 medium supplemented with 10% fetal bovine serum. Cells were grown till confluent in 100 mm culture dish and lysed in 0.5 ml of RIPA buffer (50 mM Tris-HCl, pH 7.5, 150 mM NaCl, 0.5% Triton X-100, 0.1% SDS, 0.5% Deoxycholic acid, sodium salt and protease inhibitors). Protein concentrations were determined by using BCA-200 protein assay kit (obtained from Pierce, Rockford, Ill.). 15 μg of total protein from each cell strain/line was resolved by 12% SDS-PAGE. The separated proteins were transferred onto PVDF membrane, followed by immunoblot with human thymidylate synthase monoclonal primary antibody (manufactured by NeoMarkers, Fremont, Calif.) and horseradish peroxidase linked sheep anti-mouse Ig secondary antibody (obtained from Amersham, England). The ECL plus kit (Amersham) was used for detection of immunoreactivity. The bands corresponding to thymidylate synthase were quantified and normalized to that of tubulin by Molecular Dynamics Storm. The quantified expression levels were expressed as values relative to that of cell strain CCD18co.

I. TS Activity Assay by Tritium Release from dUMP-3H. Cells were plated in 24 well plates to a density of 30,000 cells/plate and incubated for 16 hours to allow adhesion to the plastic surface of the plate.

Immediately prior to the thymidylate synthase assay, the media was replaced with RPMI+10% dialyzed fetal calf serum. 0.5 μCi of 5-[$^3$H]deoxyuridine was added to each well, and plates were incubated for 60 minutes at 37° C. without additional $CO_2$. [$^3$H] release was measured by adsorbing 5-[$^3$H]deoxyuridine to activated charcoal (10% in 1×PBS) for 5 minutes at room temperature. After centrifugation for 5 minutes at 13,000 RPM, the amount of [$^3$H] in the supernatant was determined by liquid scintillation counting.

J. Growth Inhibition Studies. Cells growing exponentially were transferred to 384-well flat bottom tissue culture plates. All cell types were plated at a density of 500 cells per well in 25 μL of complete medium (RPMI 1640+10% fetal bovine serum+antibiotics/antimycotics). After 24 hours (day 0), 25 μL of complete medium containing the experimental compounds over the dose range of $10^{ñ3}$ to $10^{ñ10}$ M were added in triplicate. Drug exposure time was 120 hours (day 5), after which growth inhibition was assayed. 5 μL of the redox indicator, alamarBlue, was added to each well (10% v/v). After 4 hours incubation at 37° C., fluorescence was monitored at 535 nm excitation and 595 nm emission.

Concentration vs. relative fluorescence units (RFU) were plotted, and sigmoid curves were fit using the Hill equation. $IC_{50}$, indicated by the inflection point of the curve, is the concentration at which growth is inhibited by 50%.

K. Tomudex Inhibition of NB1011 Cytotoxicity. MCF7-TDX were transferred to a 384 well assay plate at 500 cells in 25 μL complete medium per well. After 24 hours (day 0), 25 μL complete medium containing a combination of NB1011 in doubling serial dilutions from 1mM and tomudex at discrete concentrations (0,1,10,100,1000 nM) were added in duplicate. Drug exposure time was 120 hours (day 5) after which growth inhibition was measured with alamarBlue as described above in Growth Inhibition Studies.

L. Enzyme Preparation. Cloned human thymidylate synthase plasmid pBCHTS was subcloned into *E. coli.* plasmid BL21 (DE3)/pET-28a(+) (Novagen) using the NdeI ñSacI insertion site, in order to add an amino terminal His tag. Enzyme was expressed in *E. coli.* by induction with IPTG, and purified by affinity chromatography on a $Ni^{2+}$ His Bind metal chelation resin (Novagen). The column $Ni^{2+}$ His Bind metal chelation column was washed with 20 mM Tris pH 7.9, 5 mM imidazole, 0.5 M NaCl; thymidylate synthase activity was eluted with 20 mM Tris pH 7.9, 60 mM imidazole, 0.5 M NaCl.

M. Enzyme Assays and Kinetic Measurements. Thymidylate synthase assays were done in 96 well Costar UV transparent plates in a reaction volume of 200 μl, consisting of 40 mM Tris pH 7.5, 25 mM $MgCl_2$, 1 mM EDTA, 25 mM-mercaptoethanol, 125 M dUMP, and 65 μM N5, N10-methylene tetrahydrofolate indicated. Tetrahydrofolate stock solutions were prepared by dissolving tetrahydrofolic acid (Sigma) directly into 0.2 M Tris pH 7.5, 0.5 M-mercaptoethanol; stock solutions were stored at −80° C. N5, N10-methylene tetrahydrofolate was prepared by adding 12 μl of 3.8% formaldehyde to 1 ml of a 0.65 mM solution of tetrahydrofolate and incubating for 5 minutes at 37° C. N5, N10-methylene tetrahydrofolate was kept on ice and used within 2 hours of preparation.

Conversion of BVdUMP to fluorescent product(s) by thymidylate synthase was measured in 200 mul thymidylate synthase reactions containing 125 M BVdUMP in 96 well Dynex Microfluor Black "U" bottom microtiter plates using an excitation wavelength of 340 nm and emission wavelength of 595 nm. Fluorescence was measured with a Tecan Spectrafluor Plus fluorimeter.

Enzyme kinetic constants ($K_m$ and $V_{max}$) were determined for the human thymidylate synthase substrates dUMP and BVdUMP using the enzyme assay conditions described above. The initial rates of the enzyme reactions was determined by measuring the increase in $A_{340}$, for the reaction with dUMP, and decrease in $A_{294}$ for the reaction with BVdUMP. The catalytic efficiency of the enzyme ($K_{cat}/K_m$) was calculated from the kinetic constants $K_m$ and $V_{max}$.

N. Liquid Chromatography/Mass Spectroscopy. Cells were washed three times with PBS at room temperature, then subjected to freeze/thaw lysis in 5 ml PBS. Cell extracts were centrifuged for 10 minutes at 10 KRPM, then adsorbed to Sep-Pak $C_{18}$ and washed with 10 ml PBS. BVdUMP was eluted with 1 ml distilled water. LC/MS samples were analyzed by reverse phase chromatography on a $C_{18}$ column using a linear gradient of 0.1% formic acid-0.1% formic acid/95% acetonitrile. Mass spectroscopy was done with a Micromass Quattro II triple quadropole spectrometer.

O. Reversal of Resistance. The origin and characteristics of the human breast cancer MCF7 TDX cell line have been previously described (Drake, et al. (1996) Biochem. Pharmcol. 51(10): 1349-1355). Briefly, MCF-7 breast cancer cells were selected in vitro for resistance to Tomudex by continuous exposure to stepwise increases in TDX concentrations up to 2.0 μM. A resistant subline was selected for resistance to NB1011 by continuous exposure of the parental MCF7 TDX cell line to medium supplemented without TDX but with 50 μM NB1011, a concentration approximately 16 times higher than the $IC_{50}$ for NB1011 in the parental MCF7 TDX cell line. After a dramatic initial cell killing effect, resistant colonies emerged, and vigorously growing monolayers were formed. TS protein level and $IC_{50}$ for 5-FU, TDX, and NB1011 were determined for the resultant MCF7 TDX/1011 cell line as described in "Materials and Methods" by western blot and the alamarBlue cytotoxicity assay, respectively.

II. Experimental

A. Analysis of NB1011 in TS-expressing, 5FU resistant, H630-10 colon carcinoma xenografts in vivo. H630-10 colon cancer cells, selected for resistance to 5-FU in vitro, express high levels of thymidylate synthase, and form xenografts in athymic mice. Following cell expansion ex-vivo H630-10 were injected subcutaneously (S.Q.) at $1.5 \times 10^7$ cells/tumor in the mid-back region of 4-6 week old, female, CD-1 (nu/nu), athymic mice (Charles River Laboratories, Wilmington, Mass.). Tumor volumes, calculated as the product of length, width, and depth, were monitored twice weekly by serial micrometer measurements by a single observer. Six animals were randomly assigned to each treatment group and statistical tests were performed (single-factor ANOVA) to assure uniformity in starting tumor volumes between treatment and control groups at the beginning of the experiment. NB1011 was administered by intraperitoneal (I.P.) or intratumoral (IT) injection. The dosage of experimental agents tested were as follows: Group 1: DMSO vehicle control solution (IP), Group 2: 5-FU (15 mg/kg×5 days IP=the MTD for 5-FU in this model), Group 3: NB1011=1.25 mg×5 days (IP), Group 4: NB1011=2.5 mg×5 days (IP), Group 5: NB1011=3.5 mg×5 days (IP), Group 6: DMSO control (IT), Group 7: NB1011=1.25 mg×5 days (IT), and Group 8: NB1011=2.5 mg×5 days (IT). These doses were based on independent dose-finding experiments conducted in our laboratory and were near the maximum-tolerated dose of NB1011 for this specific age and strain of female athymic mice. To assure accurate dosing, drug doses were individualized based upon animal weights determined immediately prior to each injection. Treatment with control solution or NB1011 was initiated 10 days status post xenograft inoculation at which time xenograft volumes measured 45-68 $mm^3$. Differences in day 25 xenograft volumes between groups were analyzed by single-factor ANOVA of the log transformed tumor volume data. Experimental athymic mice were maintained under aseptic conditions in a dedicated room in the UCLA Animal Care Facility. The University of California, Los Angeles has an Animal Welfare Assurance document on file with the Office of Protection from Research Risks, Laboratory Animal Safety Assurance Number A-319-01. All experiments were closely supervised by the UCLA veterinarian. Euthanasia techniques employed by UCLA are supported by the Panel of the American Veterinary Medical Association. The University of California, Los Angeles experimental animal program and facilities are accredited by the American Association for the Accreditation of Laboratory Animal Care. The personnel performing the animal procedures/manipulations described in this protocol are technically competent in those procedures and have received their training on the use of animals in research, as required by the Animal Welfare Act of 1985.

B. In vitro Reaction of BVdUMP with Human Thymidylate Synthase

1. The Cell-Free Processing of BVdUMP by rHuTS Generates Fluorescent Product(s).

The cell-free processing of BVdUMP by *L. casei* TS has been shown to create potentially reactive intermediates (Barr, et al. (1983) supra). For this reason it has been thought that processing of BVdUMP by TS leads to irreversible inactivation of human TS (Balzarini (1987) Mol. Pharmacol. 32(3): 410-6). The cell-based experiments by DeClercq, Balzarini and colleagues (Balzarini (1987) supra; Balzarini (1993) J. Biol. Chem. 268(a): 6332-7; Balzarini (1995) FEBS Lett 373(1):41-4) support the concept that, once BVDU is converted to the monophosphate in cells (via herpes virus thymidine kinase), then it binds to and inactivates the Hu TS enzyme during processing. However, the actual reaction of human TS with BVdUMP has never been adequately characterized. Santi and colleagues (Barr (1983) supra) utilized a bacterial TS for their work to show generation of product from the BVdUMP+TS reaction, and DeClercq and colleagues utilized cells and cell lysates, not purified human TS (Balzarini (1987) supra); Balzarini, (1993) supra; Balzarini (1995) supra).

Figure 2:
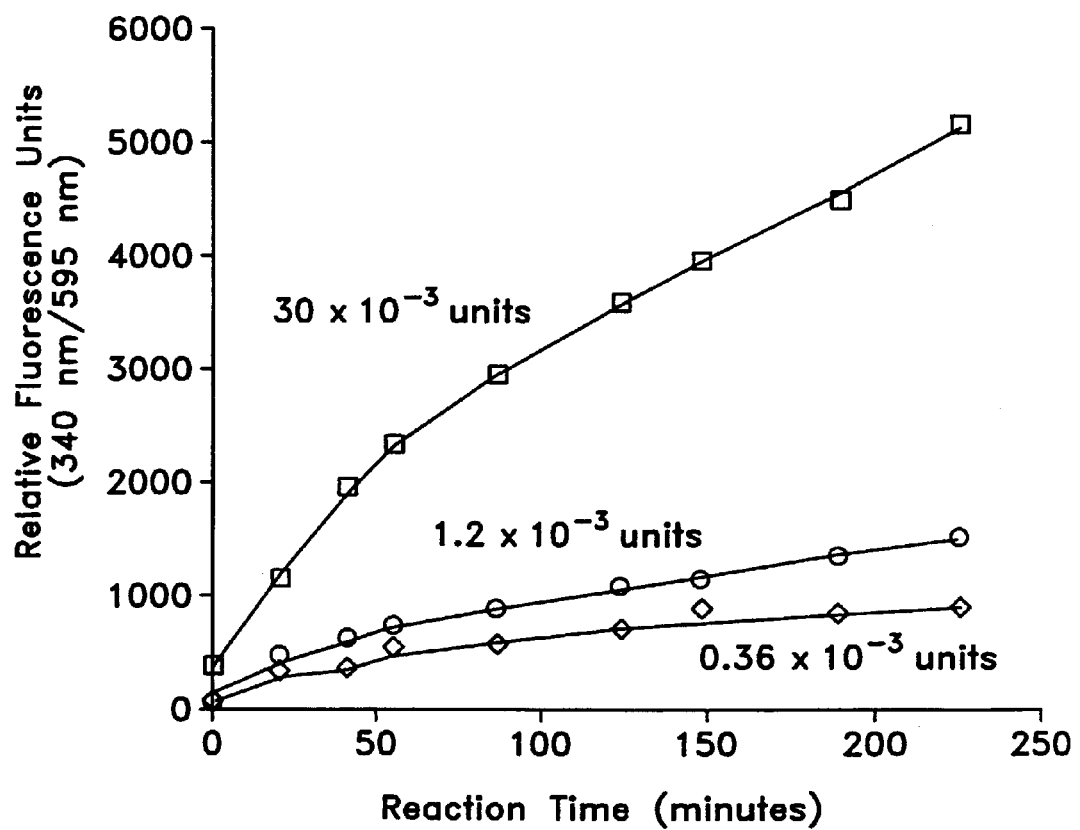
FIG. 2 is a graph showing fluorescent products from incubation of Bromovinyl$^{2'}$-Deoxyuridine Monophosphate ("BVdUMP") with Recombinant Human Thymidylate Synthase ("rHuTS"). Incubation of BVdUMP with thymidylate synthase ("TS") results in a time and enzyme dependent generation of fluorescent product(s). BVdUMP was incubated with the indicated amounts of rHuTS in the standard reaction mixture at 30° C. (Materials and Methods), except that N5, N10-methylenetetrahydrofolate was omitted from the reaction. The numbers adjacent to each data curve refer to TS enzyme units.
Figure 3:
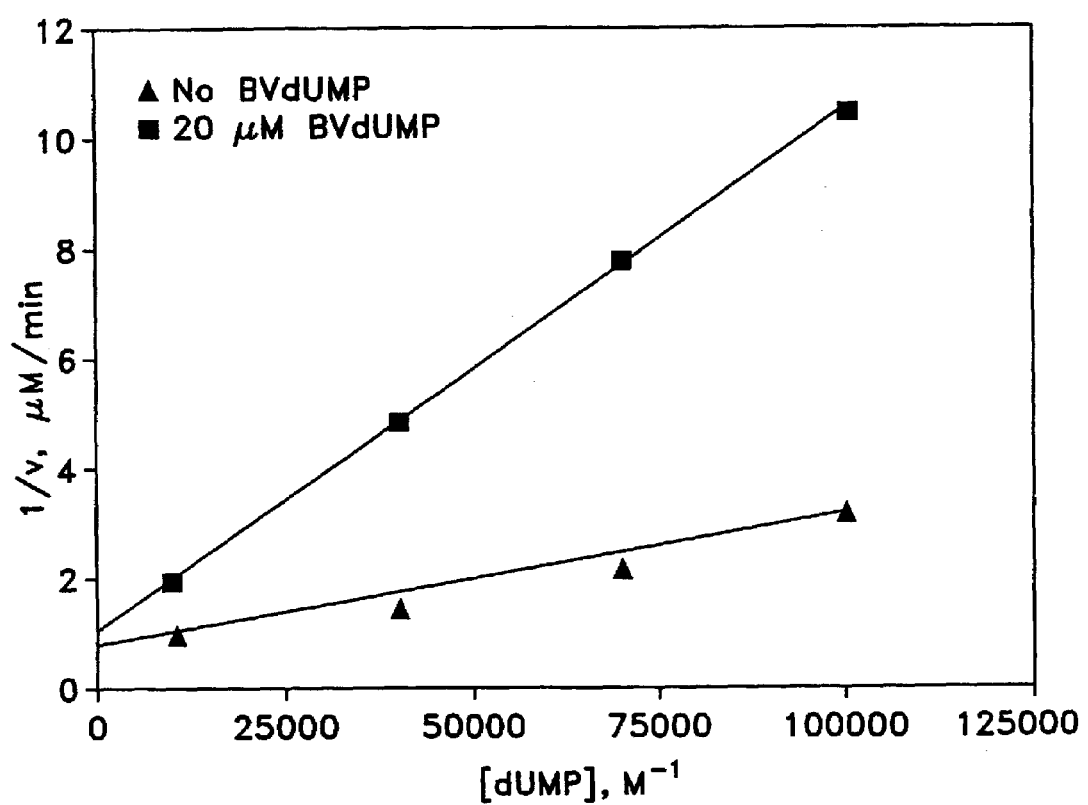
FIG. 3 shows that BVdUMP is competitive with Deoxguridine Monophosphate ("dUMP") in rHuTS. Thymidylate synthase catalyzed reaction of converting dUMP into dTMP was run in vitro in the absence (triangles) and in the presence of 20 µM BVdUMP (squares). dUMP concentration was varied from 10 to 100 µM, N5, N10-methylene tetrahydrofolate concentration was 140 µM and the enzyme concentration was 0.1 µM. Enzyme activity was determined by measuring the increase in $A_{340}$.

Because of Applicants' interest in generating therapeutic substrates that can be specifically activated by TS, the interaction of BVdUMP with purified recombinant human TS (rHuTS) was revisited. When BVdUMP was incubated with rHuTS in the standard reaction mixture, the reaction results in the formation of fluorescent product(s) (FIG. 2). The time dependent increase in fluorescence is accompanied by a decrease in the initial BVdUMP concentration. The product(s) produced have been partially characterized, and appear to be exocyclic pyrimidine nucleotide derivatives (see below).

This result is surprising because previous results supported the idea that TS reaction with BVdUMP should inactivate the human TS enzyme (Balzni, et al. (1987), (1993), (1995), supra). Because the reactions described above were done in a cell-free system with purified components, it remained possible that the intracellular milieu could provide components that would result in TS inactivation following conversion of NB1011 to the free nucleotide monophosphate inside the cell. This issue is addressed in more detail below.

2. Comparative Reaction Kinetics of dUMP and BVdUMP with rHuTS.

Previously reported work by Barr, et al.(1983), utilizing the *L. casei* TS (Balzarini (1995) supra and Balzarini (1987) supra; Balzarini (1993) supra; Balzarini, (1995) supra) using cells and cell lysates, leaves unclear whether the reaction of BVdUMP with human TS will result in irreversible inactivation of the enzyme. To address this question, the kinetics of interaction of BVdUMP with rHuTS, in the presence or absence of dUMP, were determined.

Figure 4:
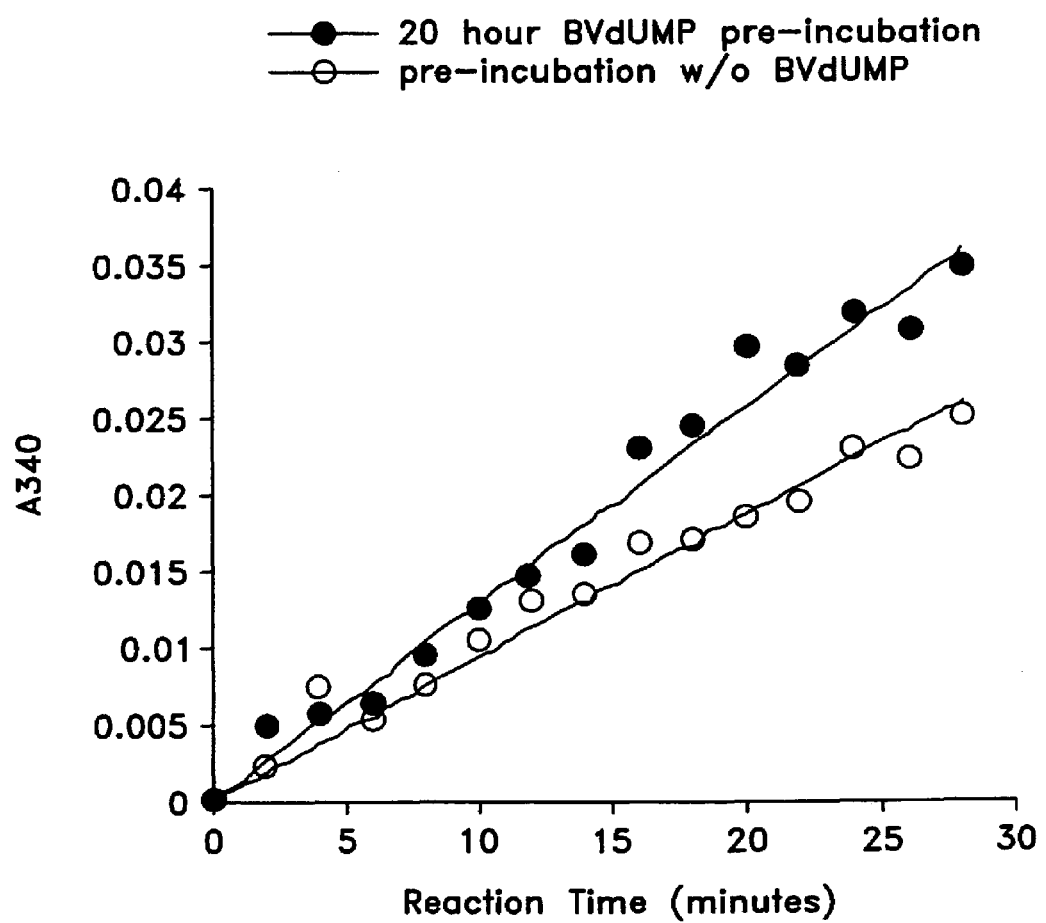
FIG. 4 shows the results of an experiment that demonstrates that preincubation with BVdUMP does not inactivate rHuTS. Human thymidylate synthase was pre-incubated in reaction mixtures with and without 125 µM BVdUMP. After 20 hours, BVdUMP was added to a concentration of 125 µM, dUMP to a final concentration of 125 µM, and N5, N10-methylene tetrahydrofolate was added to 70 µM. Thymidylate synthase activity was determined by measuring the increase in $A_{340}$, Solid circles (preincubated reaction), Open circles (no preincubation).

Competitive inhibition is most consistent with a reaction in which BVdUMP does not inactivate the TS enzyme. To help further clarify this situation, an extended incubation of rHuTS with BVdUMP was done in order to measure any inactivation that may occur over a period of time longer than that in which the kinetics were performed (FIG. 4).

These data show that even after a 20 hour incubation of rHuTS with BVdUMP, little or no enzymatic inactivation is apparent as measured by rate of conversion of THF DHP dUMP as substrate. This result is consistent with the hope for ability of overexpressed TS to convert BVdUMP into cytotoxic metabolites in cells, preferentially in cells which overexpress TS, and finally, without inactivating the enzyme.

3. Characterization of BVdUMP Reaction with TS: Cofactors and Inhibitors

The best characterized reaction of TS is the conversion of dUMP to dTMP. This reaction involves the transfer of a methylene group from N5,N10-methylene tetrahydrofolate (THF) to the C-5 position of dUMP (Carreras CW (1995) supra). This reaction is dependent upon the cofactor (THF), and is inhibited by the uridylate mimic, 5F-dUMP, which, upon reaction with the enzyme, results in the formation of a stable complex and loss of enzymatic activity. A second well characterized inhibitor of TS activity is Tomudex, which occupies the folate binding site of the TS homodimer, prevents the binding of THF, and blocks TS activity in the cell (Drake (1996) Biochem. Pharmacol. 51(10): 1349-1355 and Touroutoglou and Pazdur (1996) Clin. Cancer Res. 2(2):227-243). As part of a preliminary effort to characterize the reaction of rHuTS with BVdUMP, the effects of 5F-dUMP, Tomudex and cofactor were compared on the reaction of the enzyme with dUMP and BVdUMP. These experiments (Table 4) have shown that, similarly to the case of dUMP, 5F-dUMP can prevent conversion of BVdUMP to fluorescent product(s). In addition, Tomudex can also prevent product formation from both dUMP and BVdUMP. However, consistent with earlier reported results with *L. casei* TS (Barr, et al. (1983) supra), THF is not required for the conversion of BVdUMP to fluorescent product(s). In addition, the data shown in Table 4 also demonstrate that THF stimulates the production of fluorescent product(s) in the BVdUMP reaction with rHuTS. This result is not expected from the earlier data reporting that THF has no effect on this reaction (Barr, et al. (1983) supra), and illustrates a potentially important possibility that cofactors, or cofactor agonists, like leucovorin, could modulate the reaction of BVdUMP with human TS.

Analysis of the Michaelis-Menton kinetics of this reaction showed that inhibition of BVdUMP by dUMP fits the expected form for competitive inhibition, consistent with both nucleotides behaving as substrates for rHuTS.

Previously reported data with the *L. casei* TS indicated that BVdUMP is 385 times less efficient a substrate as dlMP (Barr, et al. (1983) supra; Santi D. V. (1980) supra). The experiments reported herein have shown that this situation is quite different with the human enzyme. For rHuTS the relative catalytic efficiency of dUMP compared with BVdUMP is 60x. This represents a >6.4 fold increase in catalytic efficiency as compared to endogenous substrate. The previous result with *L. casei* TS leads to the prediction that the efficiency of enzymatic reaction within the cell would be too low for NB1011 to be an effective therapeutic substrate, since it would have to compete with large amounts of endogenous dUMP. The discovery reported herein, ie. that the human enzyme has a >6.4-fold improved efficiency of conversion of BVdUMP, is an important factor enabling utility of NB1011. The increased efficiency of BVdUMP utilization by the human enzyme as compared to the *L. casei* enzyme also establishes that species specific substrates are possible and can be designed. The ability to specifically inhibit heterologous enzymes via binding to species specific regions on the surface of *L. casei* vs. human TS has recently been reported (Stout (1999) Biochemistry 38(5): 1607-17 and Costi, et al. (1999) J. Med. Chem. 42(12):2112-2124). Differences in specificity relating to the active site of TS, which is composed of the most highly conserved regions of the protein (Carreras (1995) supra) is surprising and has not been reported previously.

Products of the cell-free enzymatic reaction of rHuTS with BVdUMP were analyzed by mass spectroscopy. The molecular structures I and II shown in FIG. 5 have masses that are consistent with the mass of molecular ions detected in TS reaction mixtures following incubation of BVdUMP with purified rHuTS. Knowledge of the products of this reaction may be used to understand the final mechanism of action of NB1011. In addition, this information could be used to design novel chemotherapeutics, since the products of the TS-BVdUMP reaction could, themselves, be potentially used as chemotherapeutics.

4. NB1011 is Converted to the Monophosphate in Tumor Cells.

NB1011 is converted from the phosphoramidate to the monophosphate form in cells, as a prerequisite for binding to TS. The proposed pathway for unmasking the phosphate of NB1011, its binding to TS and conversion to toxic metabolites is shown in FIG. 6.

To determine whether this crucial step in conversion was taking place advantage was taken of an unusual property of the bromine atom, i.e. that it exists in nature in two equally abundant isotopic forms. This situation allows detection of the bromine containing monophosphate by focusing the mass spectrometry analysis on the predicted mass ions of BVdUMP (411 and 413 daltons). H630 R10 tumor cells (which express high levels of TS) were incubated with 100 uM NB1011. Extracts of treated cell lysates were prepared as described in Methods. Detection using mass spectroscopy, following an initial purification with liquid chromatography relied upon formation of the unprotected nucleotide mass ions of BVdUMP which have identical retention times on reverse phase chromatography.

Figure 7A:
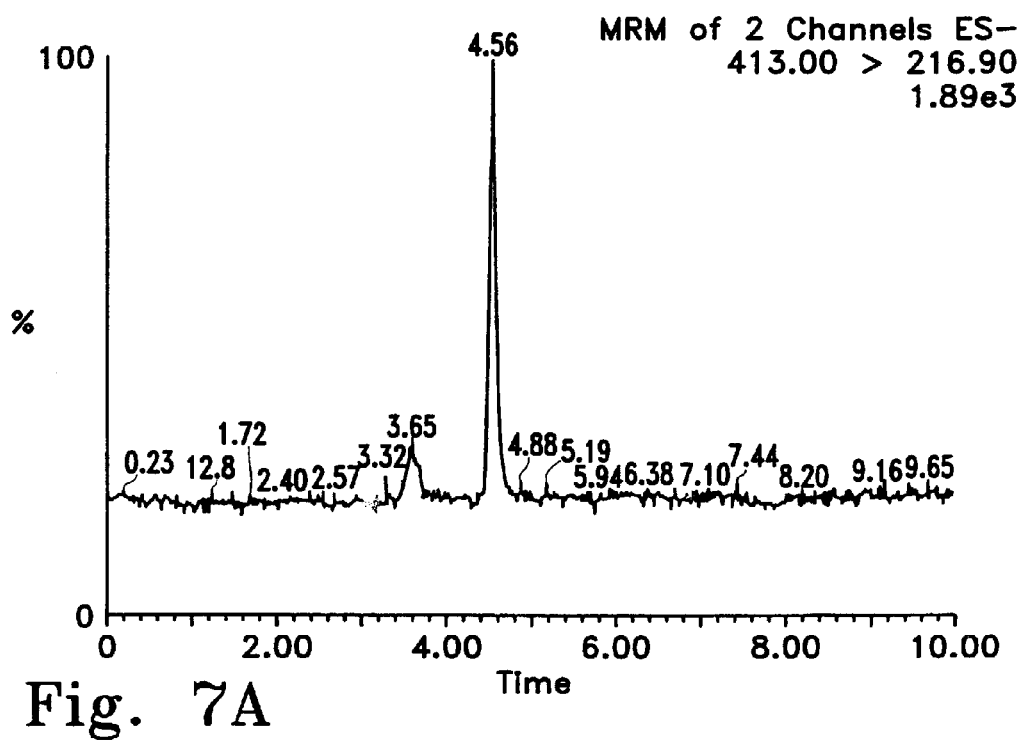
FIG. 7 shows detection of BVdUMP in H630R10 cells treated with NB1011. H630 R10 cells were treated with 100 µM NB1011 for 5 days, then analyzed by LC/MS as described in Materials and Methods.
Figure 7B:
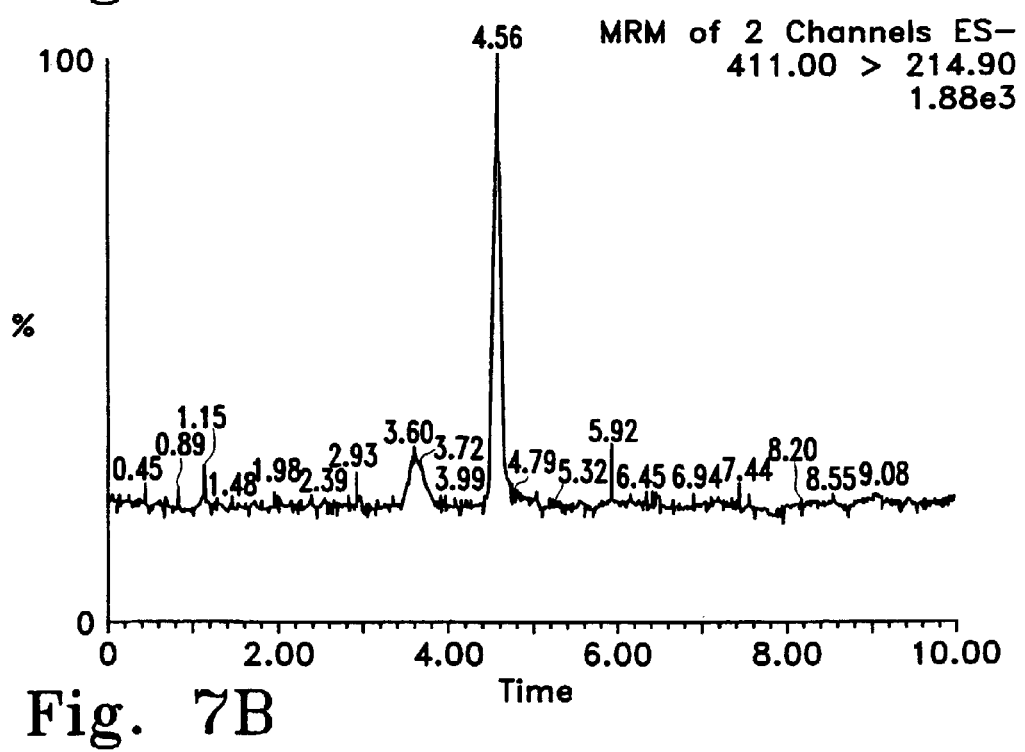

These results (FIG. 7) are consistent with NB1011 following the first step in the activation pathway).

C. Characterization of the Cytotoxic Activity of NB1011.

1. The Tumor/Normal Cell Screen.

As an initial step in characterizing the biological activity of NBl111, a large series of normal and tumor cell types were tested in the alamar blue assay for sensitivity to both NB1011 and 5-fluorouracil.

Assays were carried out as described in Methods, above. Therapeutic index is calculated as the ratio of the average $IC_{50}$ for normal cells to the average $IC_{50}$ for tumor cells. All assays were done at least three times.

These data show that NB1011 has met the primary design goal for TS ECTA compounds, i.e. increased potency on tumor cells vs. normal cell types. Overall, NB1011 is about 2-fold more cytotoxic to tumor cells vs. normal cells, while 5FU is 3-fold more toxic to normal cells than it is to tumor cells. The total benefit of NB1011 is therefore (2)×(3)=6-fold improvement in therapeutic index for NB1011 as compared with 5FU. A critical tactic that allows for selection of chemotheraputics with a positive therapeutic index is screening of activity on both normal and tumor cell types. This approach has not been consistently employed in the field of new cancer drug discovery. For instance, screening of new candidate compounds on normal cell types is part of the National Cancer Institute's screening procedure (Curt (1996) Oncologist 1 (3): I-III).

2. NB1011 Does not Inactivate TS In Vivo.

Figure 8:
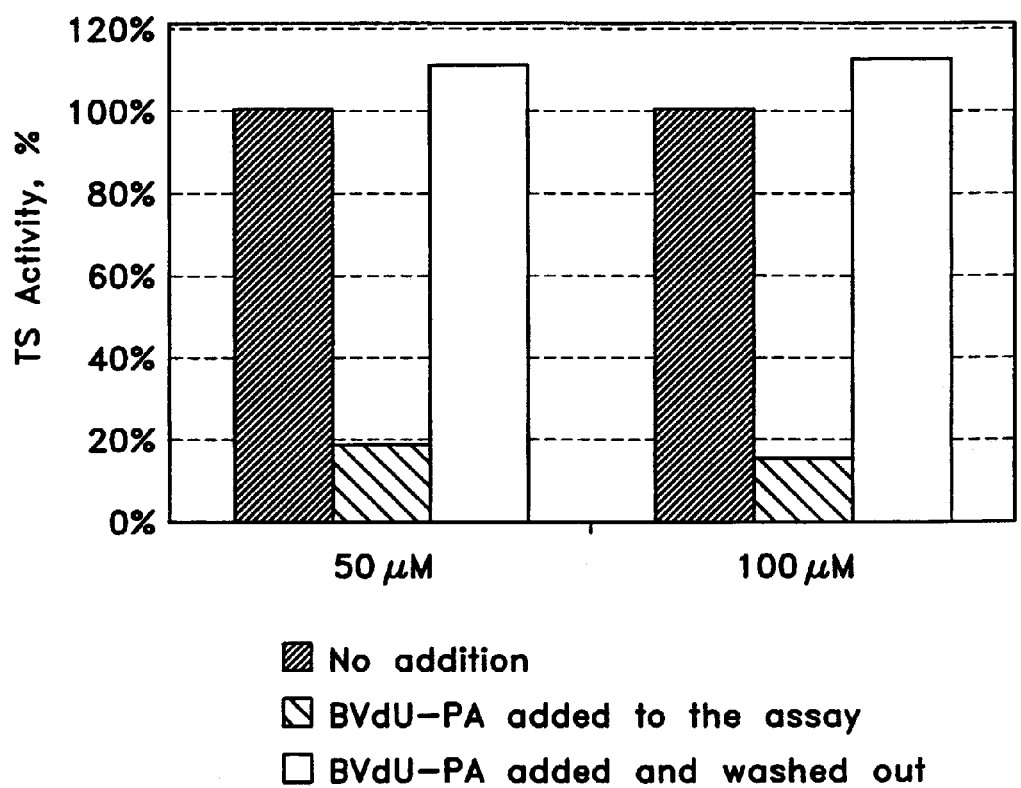
FIG. 8 demonstrates that NB1011 does not irreversibly inactivate TS in vivo. The effect of NB1011 on TS activity in intact cells is completely reversible. TS activity was measured in intact RKO cells by release of [$^3$H]$_2$O from 5-[$^3$H] deoxyuridine as described in Materials and Methods. NB1011 was washed out of cells by replacing with fresh media, incubating for 60 minutes at 37° C., then repeating this procedure. Control and untreated cells were subjected to the same washing procedure.

The results described above indicate that BVdUMP, generated intracellularly from NB1011, is unlikely to inactivate TS during its transformation to product(s). However, the cell free system is different from the intracellular milieu. In order to further explore this question, cell-based assays for TS activity were performed. In these experiments exogenous 5-($^3$H) deoxyuridine is added to cell culture medium and the release of tritiated water is monitored (Carreras and Santi (1995) supra; Roberts (1966) Biochem. 5(11) 3546-3548). FIG. 8 shows that the presence of NB111 in cell culture media reduces the rate at which [$^3$H]$_2$O is released from 5-[$^3$H] dUMP. In order to determine whether this is the result of irreversible inhibition of TS, NB1011-treated cells were allowed to briefly recover in fresh culture media, then assayed for TS activity. Cells that have been allowed to recover in culture media lacking NB1011 have the same level of TS activity as untreated cells. This result supports the proposal that NB1011 does not irreversibly inactivate the TS enzyme following intracellular processing.

An additional approach was taken to understanding whether NB1011 might interfere with cell growth primarily by inactivating TS. This approach is based upon thymidine rescue of TS-blocked cells. Cells which are blocked by Tomudex or by 5FdUMP (following treatment by 5FdUrd) do not make dTMP by de novo synthesis. For this reason, they survive only by scavenger mechanisms. One of the important scavenger mechanisms is utilization of extracellular thymidine. Thymidine incorporated by target cells can be converted to dTMP, usually by thymidine kinase, and thus continue DNA synthesis. Other pathways for use of exogenous thymidine have also been described If an important mechanism for NB1011 activity is via inhibition of endogenous TS, then the cytotoxicity should be relieved when thymidine is added to the cell culture media. For this experiment, a number of tumor cell lines were screened for their sensitivity to Tomudex and 5FdUrd, and ability to be rescued from these agents via thymidine supplementation. The normal colon epthelial cell, CCD18co, was used because of its measurable sensitivity to NB1011, 5FUdR and Tomudex. Experiments were carried out as described by (Patterson, et al. (1998) Cancer Res. 58: 2737-2740) with or without 10 uM thymidine, except that the alamar blue assay (see Materials and Methods) was employed to determine cytotoxicity. The results showed a 15-fold rescue from Tomudex ($IC_{50}$ change from 6.5 nM to 95 nM), a greater than 590-fold rescue from 5FudR (from an $IC_{50}$ of less than 0.01 µM to greater than 5.9 µM), and a slight decrease in the absence of thymidine to 223 µM in the presence of 10 µM thymidine.

3. Relationship Between TS Level and NB1011-Mediated Cytotoxicity on Tumor Cell Lines.

Confirmation that TS participates in NB1011-mediated cytotoxicity was established using several approaches: 1). The activity of NB1011 was examined on normal colon cells vs. high TS expressing, 5FU-resistant, tumor cells; 2). transfection of TS into a tumor cell background, and generating clonal derivatives which differ primarily by TS expression level, but are otherwise very similar, and 3). Use of a specific inhibitor of TS, Tomudex, to decrease intracellular TS activity.

In the initial analysis, of NB1011 and 5FUdR-mediated cytotoxicity were compared on the CCD18co normal colon epithelial cell type and H630R10, 5FU-resistant colon tumor cell line (Copur, et al. (1995) Biochem. Pharm. 49(10): 1419-1426). This allows a determination of cytotoxicity vs. normal cells (CCD18co) as well as a measure of cytotoxicity vs. drug-resistant tumor cells (H630R10), which overexpress TS. This is important because a significant limitation to current chemotherapeutics is their toxicity to normal tissues. The results are presented in Table 4.

This experiment shows that 5FUdR is about 18-fold more toxic to normal colon cells (CCD18co) than to 5FU-resistant H630R10 tumor cells. This negative therapeutic index characterizes the major limitation of current chemotherapy, i.e. its toxicity to normal tissue. Such a negative therapeutic index has also been reported for doxorubicin (Smith, et al. (1985) J. Natl. Cancer Inst. 74(2): 341-7 and Smith, et al. (1990) Cancer Res. 50(10): 2943-2948). In contrast to 5FUdR, however, NB1011 has more than an 11-fold improved activity on drug-resistant H630R10 cells ($IC_{50}$=216.7 KM) vs. normal colon epithelial cells ($IC_{50}$ greater than 2500 µM). This result suggests that: 1). Activity of NB1011 is more pronounced on high TS expressing tumor cells; and 2). A total improvement in therapeutic index of (18)x(11)=198-fold is achievable using TS ECTA compounds vs. 5FUdR.

4. Overexpression of TS in HT1080 Tumor Cells Enhances Their Sensitivity to NB1011.

Activation of NB1011 requires several steps. These include cell penetration conversion to the nucleotide monophosphate, binding to TS, and subsequent toxic metabolism. The precise mechanisms of cell penetration and conversion are not fully defined. Cell entry may depend in part on nucleoside transport mechanisms (Cass, et al. (1998) Biochem. Cell Biol. 76(5): 761-70). Similarly, processing from the phosphoramidate to the monophosphate employs poorly defined mechanisms (Abraham, et al. (1996) J. Med. Chem. 8: 39(23): 4589-4575).

These results are particularly significant because they demonstrate, in a fairly uniform genetic background, that increasing TS levels predicts enhanced sensitivity to NB1011. In addition, the data also show that increasing TS levels predicts resistance to fluoropyrimidines, a result consistent with reports in the literature (Copur, et al. (1995) supra; Banerjee, et al. (1998) Cancer Res. 58: 4292-4296).

5. Inhibitors of NB1011-Mediated Cytotoxicity.

Tomudex is a chemotherapeutic that acts primarily via inhibition of TS. If NB1011 exerts cytotoxicity via the TS enzyme, then inhibition of TS with Tomudex should decrease NB1011-mediated cytotoxicity. To test this hypothesis directly, Tomudex-resistant MCF7 cells, which overexpress TS 11-fold compared to the parental MCF7 cell line, were exposed to NB1011 in the presence of increasing concentrations of TDX.

Cells were plated and exposed to indicated concentrations of compound(s) as described in the Materials and Methods Section, above.

The data show that blockade of TS using the specific inhibitor Tomudex, results in up to about 25-fold inhibition of NB1011-mediated cytotoxicity. These results support the concept that activity of NB1011 results from its metabolism by TS.

To further characterize the intracellular metabolism of NB1011, combination experiments with leucovorin (LV; 5-formyltetrahydrofolate) were performed. This experiment was initiated because we had observed that THF stimulates production of fluorescent product(s) in the cell-free reaction of BVdUMP and rHuTS. It was hypothesized that if the fluorescent products are related to the cytotoxic effects of NB1011, then enhancing intracellular levels of THF by providing LV in the culture media would also enhance NB1011-mediated cytotoxic effects. Surprisingly, in the presence of 31M LV, NB1011 activity on the H630R10 cell line was diminished by more than 90%, compared to NB1011 alone, as determined in the alamar blue assay. The fact that NB1011 activity is abolished by LV, which supplements intracellular reduced folate pools, suggests that NB1011 may work in part by diminishing these pools. Alternatively, LV (or a metabolite) could directly impact the metabolism of BVdUMP by interfering with its interaction with TS.

To explore whether LV could directly impact the reaction of BVdUMP with TS, reactions were carried out +/−THF with BVdUMP, or with ThF+dUMP, and +/− Methotrexate (MTX), LV or Tomudex (TDX).

The results (Table 6) are surprising in two respects: 1). Although an increase in fluorescent product was noted from BVdUMP in the presence of THF, a decreased rate of substrate consumption (BVdUMP) utilization occurs in the presence of the cofactor; and 2). In the presence of cofactor, all three compounds tested (MTX, TDX and LV) dramatically inhibited the BVdUMP+rHuTS reaction. In each case, the inhibition was more pronounced than that seen in the dUMP+ rHuTS reaction, or the reactions with BVdUMP in the absence of THF.

The results described above, demonstrating inhibition of the BVdUMP+TS reaction by LV, MTX and TDX, and further, that this effect is more pronounced in the presence of cofactor (THF), suggests that NB1011 activity may be modulated by other chemotherapeutics. Importantly, rescue of NB1011-treated cells is feasibleby providing LV, similar to the LV rescue from MTX. In the case of MLX, LV rescue occurs via supplementation of intracellular folate pools, which are diminished via MTX inhibition of dihydrofolate reductase and TS. If reduced folates are diminished within the cell during BVdUMP reaction with TS, then other compounds that diminish intracellular thymidine or purine nucleotide pools by distinct mechanisms may give additive or synergistic anti-cellular effects when used together with NB1011. Examples of such compounds (Dorr and Von Hoff (1994) supra), include 6-mercaptopurine, thioguanine and 21-deoxycoformycin, all of which interfere with purine metabolism. Azacytidine-mediated inhibition of orotidylate decarboxylase blocks pyrimidine biosynthesis, and so could lower intracellular thymidine levels in a cell by a mechanism distinct from that of NB1011.

C. Pharmacogenomics of TS ECTA

1. Comparison of TS and HER2.

Figure 9:
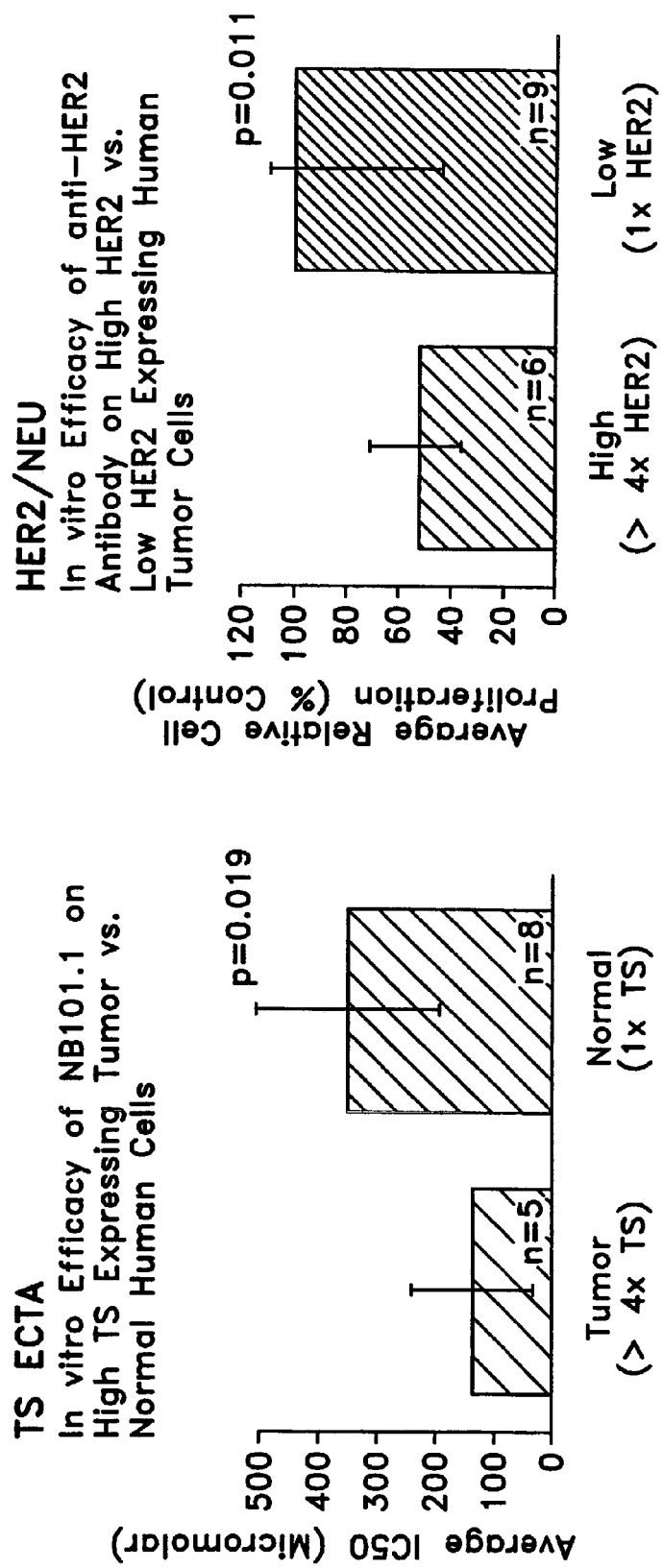
FIG. 9 shows that there are marked similarities between in vitro efficacy requirements for NB1011 and anti-HER2. A), Data are taken from Tables 3, 4, and 7. B). Data from Shepard, et al. (1991) J. Clin. Immun. 11(3): 117-27 Vertical bars show standard error of means calculated using the Mann-Whitney U test.

An important aspect of the current approach to discovery and development of novel therapeutics is the ability to identify patients who are most likely to respond to treatment (a positive pharmacogenomics selection). One of the pioneering drugs in this area is Herceptin, now used to treat breast cancers which overexpress the HER2 protooncogene. Early data with anti-HER2 antibodies showed that activity on randomly selected tumor cells and normal cells was minimal. However, if tumor cell lines were selected that had at least a 4-fold increased expression of HER2, then a significant activity and anti-HER2 antibody could be demonstrated, as compared to normal cells or tumor cells expressing lower amounts of the HER2 gene product (Shepard, et al. (1991) supra); (Lewis (1993) Cancer Immural Immunother 37(4): 255-63). The data shown in FIG. 9 demonstrate that, similarly to the case with Herceptin, The cell line results shown in FIG. 2 may suggest an additional similarity between the TS and HER2/NEU systems. The similarity is that each has a similar overexpression requirement (about 4-fold) which predicts more aggressive disease for both TS and HER2/NEU overexpressing patients (Johnston, et al. (1994) J. Clin. Oncol. 12: 2640-2647).

2. NB1011 is Active Against 5FU and Tomudex-Resistant Colon and Breast Tumor Cell Lines.

Because NB1011 has promising anticancer activity, it is important to compare it with other chemotherapeutics with respect to safety. The utility of NB1011 in the treatment of cancer is further strengthened when it is compared with Tomudex, a chemotherapeutic which, like 5FU, is often used to treat colon and breast cancer, among other malignancies.

Figure 10:
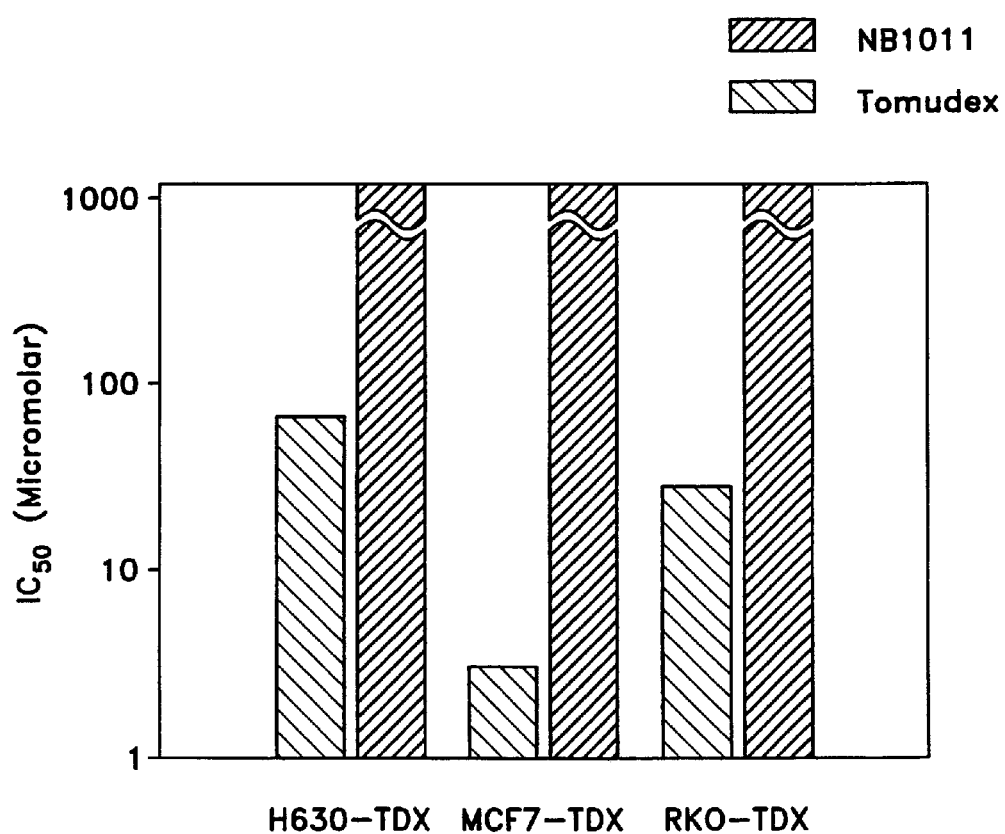
FIG. 10 shows that NB1011 is highly active against Tomudex resistant cancers. Cytotoxicity vs. TDX$^R$ cell lines was measured in the alamar blue assay, as described in Materials and Methods, below.

The results (FIG. 10) show that while NB1011 is more than 10-fold less toxic than TDX vs. normal cells (CCD18co), it is more than 30-fold more potent than TDX on MCF7-TDX resistant tumor cells. Similar results have been obtained for other TDX-resistant tumor cell lines. The low level of toxicity vs. normal cells and the high activity vs. $TDX^R$ tumor cells supports the application of NB1011 to drug resistant cancers that overexpress TS.

3. NB1011 is More Dependent Upon TS Protein Levels Than TS Activity as Measured by Tritium Release from dUMP-3H.

Four types of assays have been used to characterize TS levels in cells and tissues. Most commonly used is the antibody-based technique (Johnston (1994) supra; (Johnston (1995) supra) but RT-PCR, 5FdUMP-binding and tritium release (van Laar (1996) Clin. Cancer Res 2(8): 1327-33; van Triest (1999) Clin. Cancer. Res. 5(3): 643-54; Jacknan (1995) Ann. Oncol. 6(9): 871-81; Larsson (1996) Acta Oncol. 35(4): 469-72; Komaki (1995) Breast Cancer Res. Treat. 35(2): 157-62; Mulder (1994) Anticancer Res. 14(6B): 2677-80) have also been measured in various studies. For characterization of cell lines we have focused on western blotting and tritium release from $^3$H-DUMP. These assays were chosen because antibody-detection is commonly used for clinical samples and tritium release from labeled deoxyuridine is a direct measure of TS catalytic activity in cells.

Cells were grown and characterized as described in Methods. TS expression level is relative to CCD18co, a normal colon epithelial cell line. Tritium release is background substracted as described in Methods. ND=Not detectable above background.

Analysis of the data presented in Table 7 indicates that there is a closer relationship between TS protein level and sensitivity to NB1011 than between TS activity (tritium release from $^3$H-dUMP) and NB1011 sensitivity. In each set of matched parental and drug-resistant tumor cell types, the drug-resistant derivatives, each with more TS protein than the parent, also have an increased sensitivity to NB1011. However, when the same comparison is done with respect to TS activity, the parental cell lines often have comparable, or greater, TS activity and are less sensitive to NB1011-mediated cytotoxicity.

While these results could occur via a number of different mechanisms, or combinations of mechanisms, it is likely that $^3$H-dUMP conversion to dTMP (and accompanying tritium release) may be subject to limitation by some component, perhaps cofactor availability. However, since conversion of BVdUMP is not dependent upon cofactor, then its reaction with TS can continue even in a cellular milieu in which cofactor is limiting. This observation is important because TS substrates as therapeutics would not be attempted based upon the results of typical tritium release assays for TS activity in which the most aggressive, and drug-resistant, tumor cells are observed to have a lower TS activity than their precursors. These results lend additional support to the proposal of selecting patients for TS ECTA therapy based simply on the level of TS detected by antibody staining.

4. TS Levels in Tumor Samples Often Exceed a 4-Fold Increase Over Normal Tissue.

The results shown above suggest that TS ECTA therapy, at least with NB1011, will be most effective when used in patients whose cancers overexpress TS at least four-fold.

Figure 11:
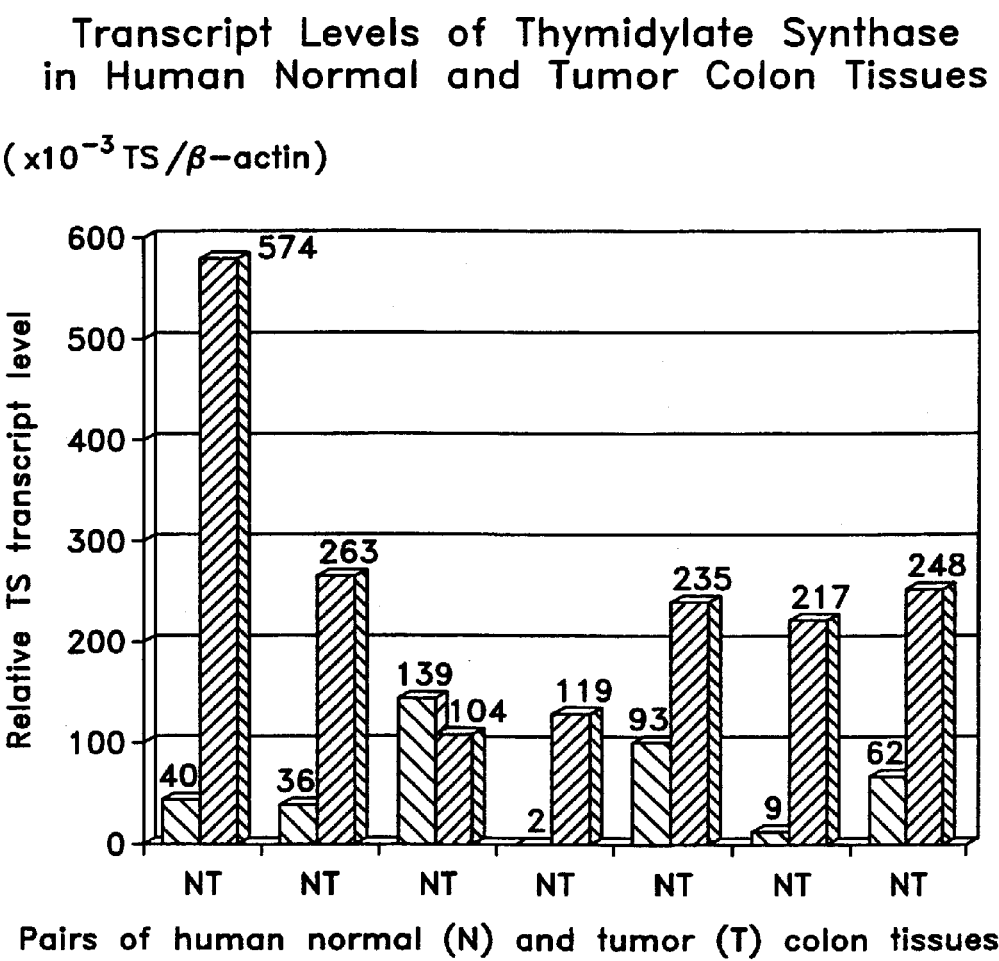
FIG. 11 shows transcript levels of thymidylate synthase in human normal and tumor colon tissues. RT-PCR analysis was performed as described in Materials and Methods, below. The ratio of TS mRNA in tumor vs. normal tissue samples, each normalized to beta-actin was (left to right) 14.35, 7.31, 0.75, 59.5, 2.53, 24.1, and 4.0.

The literature (Johnston (1994) supra; Bathe (1999) Cancer J. Sci. Am. 5(1): 34-40; Leichman (1998) Oncol. (Huntingt.) 12(8Suppl.6): 43-7; and Lenz (1995) PCR Methods Appl. 4: 305-308) suggests that overexpression in the range of 4-fold occurs in about 50% of cancers, and furthermore, that this level of overexpression predicts a more aggressive disease. To confirm the frequency of at least 4-fold overexpression of TS in human colon cancer, we obtained matched normal and tumor samples from the Cooperative Human Tissue Network. These samples were analyzed for TS mRNA level via RT-PCR, which gives results comparable to immunohistochemistry (Johnston, et al. (1995) supra). The results of the RT-PCR evaluation of the samples is shown in FIG. 11.

Five of the seven samples analyzed above have at least a 4-fold level of overexpressed TS as determined by the RT-PCR assay. None of these patients were previously treated with chemotherapy, which suggests that this frequency and level of overexpression is associated with invasive disease and not due to selection by chemotherapy. It is expected that cancer cells that have been exposed to TS inhibitors such as Tomudex or the anabolic derivative of 5FU or 5-FdUrd, 5FdUMP, may be selected for increased expression (Lonn, et al. (1996) Cancer 77(1): 107-12). The average degree of overexpression, as measured by RT-PCR for all 7 samples, is about 4.7-fold. These data suggest that greater than 4-fold overexpression of TS in tumor foci is a common event.

5. Experimental Therapy of 5FU-Resistant Human Colon Cancer.

The most important diseases for new compounds that target TS are the gastrointestinal cancers. To study the activity of NB1011 in an in vivo model, H630R10, 5FU-resistant human colon cancer cells, were grown subcutaneously to an average tumor size of 50 mm³ in nude mice. The mice were then treated, with excipient (DMSO, 5FU or NB1011).

Figure 12B:
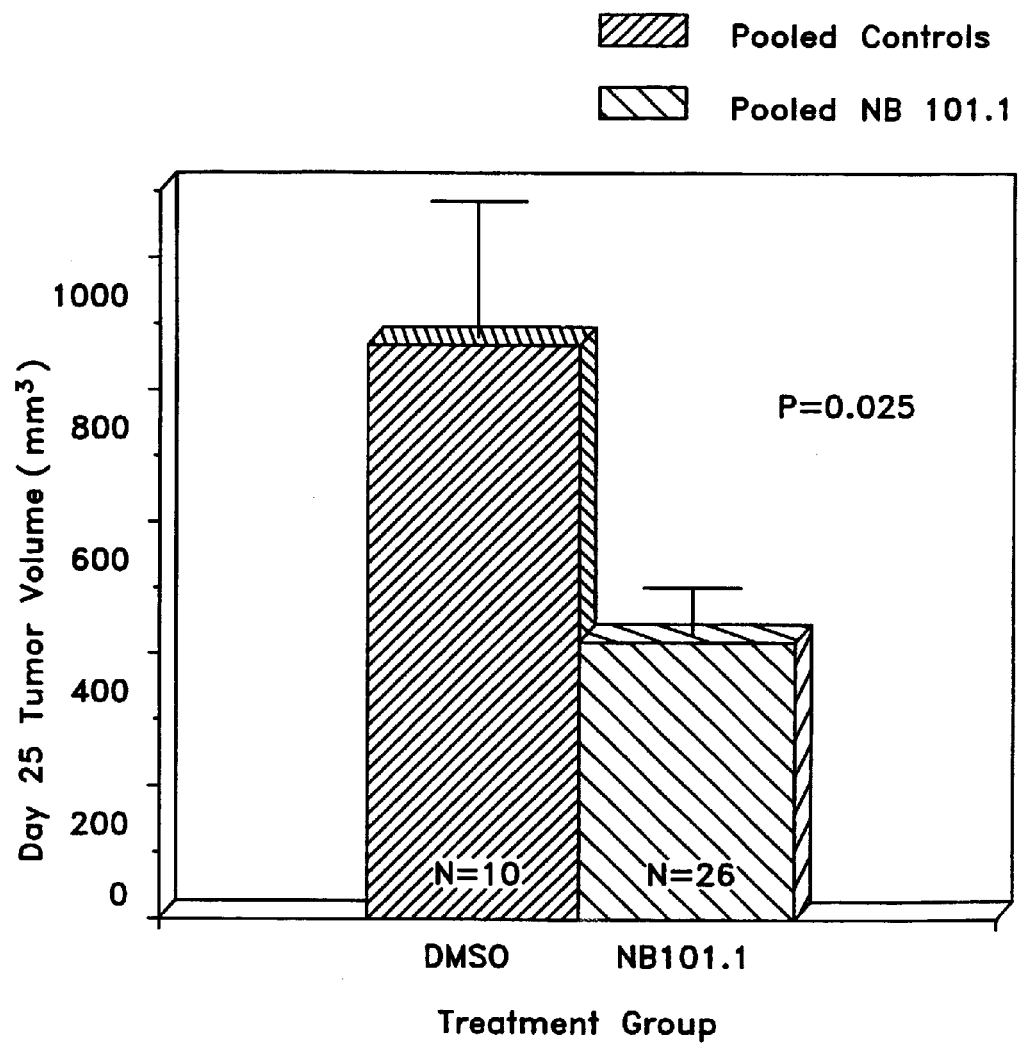
FIG. 12B is the long term response to NB1011. Analysis of pooled data at Day 25. Statistical analysis is described in the Materials and Methods section below.

Doses of 3.5 mg, 2.5 mg, and 1.25 mg of NB1011 were administered daily for 5 days, either peritumorally or intraperitoneally to tumor-bearing mice. FIG. 12A shows the initial block in tumor growth induced by treatment for 5 days with NB1011, as compared to excipient or 5FU treated animals. Although no statistically significant dose response relationship is evident among the NB1011 groups, there is a significant difference between the NB1011 groups vs. either the 5FU or excipient controls, starting with Day 6. This difference is maintained (FIG. 12B) until the control animals were sacrificed at Day 25, even though therapy was discontinued after Day 5.

While the invention has been described in detail and with reference to specific embodiments thereof, it will be apparent to one skilled in the art that various changes and modifications can be made therein without departing from the spirit and scope thereof

TABLE 2

Comparison of Kenetic Parameters of Bacterial and rHuTS

| | Kinetic Constants | *Lactobacillus casei* | rHuTS |
|---|---|---|---|
| dUMP | $K_m$ | 3.0 μM | 7.7 μM |
| | $K_{cat}$ | 6.4 s$^{-1}$ | 0.2 s$^{-1}$ |
| | $K_{cat}/K_m$ | 2.1 × 10$^6$ M$^{-1}$s$^{-1}$ | 2.6 × 10$^4$ M$^{-1}$s$^{-1}$ |
| | $K_i$ (of BVdUMP) | 0.6 μM | 4.5 μM |
| BVdUMP | $K_m$ | 3.3 μM | 16 μM |
| | $K_{cat}$ | 0.018 s$^{-1}$ | 0.0067 s$^{-1}$ |
| | $K_{cat}/K_m$ | 5.6 × 10$^3$ M$^{-1}$s$^{-1}$ | 4.2 × 10$^3$ M$^{-1}$s$^{-1}$ |
| | $K_i$ (of dUMP) | 2.0 μM | 17.5 μM |
| Relative catalytic efficiency (dUMP vs BVdUMP) | | 385-fold | 60-fold |

Enzyme kinetics were done as described in Methods. Data for *Lactobacillus casei* are derived from Barr, et al. (1983) supra. The rHuTS was prepared as described in Materials and Methods, above.

TABLE 3

Inhibition of rHuTS reactions by Tomudex and 5-FdUMP

| Substrate + Cofactor | No Inhibitor | Tomusdex (500 nM) | 5-FdUMP (500 nM) |
|---|---|---|---|
| BVdUMP + THF | 109 ± 16 RFU/min (100%) | 67 ± 3 (61%) | 44 ± 2 (40%) |
| BVdUMP − THF | 75 ± 11 (100%) | 34 ± 3 (45%) | 93 ± 13 (129%) |
| dUMP + THF | 1500 ± 20 nmoles/min (100%) | 690 ± 40 (46%) | 290 ± 70 (19%) |

Inhibition of rHuTS reactions by Tomudex and 5-FdUMP. Thymidylate synthase reactions containing enzyme inhibitors or cofactor were incubated at 30° C. as described in Materials and Methods, and the initial rates of the enzyme reaction were determined by measuring the increase in relative fluorescence units at 340 nm excitation, 595 nm emission for the BVdUMP reactions, or increase in $A_{340}$ for the dUMP reaction.

TABLE 4

Cytotoxicity of NB1011 vs. 5FU on Normal and Tumor Cell Strains

| | | IC$_{50}$ (μM) | |
|---|---|---|---|
| | | NB101.1 | 5FU |
| Normal Cells | | | |
| CCD1800 | (Colon) | 562 | 2.0 |
| DET551 | (Skin) | 262 | 0.8 |
| NHDF | (Skin) | 359 | 0.8 |
| H527 | (Skin) | 273 | 1.6 |
| W138 | (Lung) | 335 | 1.0 |
| MRC9 | (Lung) | 303 | 1.1 |
| NHLF | (Lung) | 139 | 0.9 |
| NHA | (Brain) | 839 | 0.9 |
| NHOST | (Bone) | 642 | 4.7 |
| NPRSC | (Prostate) | 369 | 1.7 |
| NHEPF | (Liver) | 2085 | 1.7 |
| | Average | 561 | 1.6 |
| Tumor Cells | | | |
| H630R10 | (Colon) | 65 | 41.6 |
| HT1080 | (Colon) | 449 | 0.8 |
| COLO320 | (Colon) | 401 | 1.5 |
| COLO205 | (Colon) | 105 | 1.3 |
| SW620 | (Colon) | 374 | 4.6 |
| SKCO1 | (Colon) | 184 | 1.4 |
| HCTC | (Colon) | 280 | 2.8 |
| MCF7 | (Breast) | 141 | 1.0 |
| MDAMB361 | (Breast) | 365 | 5.0 |
| MDAMB468 | (Breast) | 172 | 4.4 |
| SW527 | (Breast) | 431 | 4.3 |
| NCI H520 | (Lung) | 135 | 0.6 |
| SKLU1 | (Lung) | 270 | 7.9 |
| SOAS2 | (Bone) | 232 | 1.4 |
| PANC1 | (Pancreas) | 492 | 1.9 |
| SKOV3 | (Ovary) | 484 | 3.0 |
| PC3 | (Prostate) | 184 | 0.9 |
| HEPG2 | (Liver) | 704 | 22.8 |
| SKHEP1 | (Liver) | 247 | 1.7 |
| A431 | (Skin) | 266 | 0.2 |
| MCIxc | (Brain) | 61 | 1.2 |
| | Average | 288 | 5.3 |
| | | NB101.1 | 5FU |
| Therapeutic index (N/T) | | 1.95 | 0.30 |

Cells were analyzed for response to either NB1011 or 5FU in the alamar blue assay (Methods). All assays were performed at least three times. The standard deviation is less than 0%. Therapeutic index was calculated as the ratio of IC$_{50}$ (mean of all cell types) to IC$_{50}$ (mean of all tumor cell lines).

TABLE 5

NB1011 cytotoxicity on cell lines engineered to express HuTS.

| | | IC$_{50}$ | | | |
|---|---|---|---|---|---|
| Cell Line | TS Level (%) | NB1011 (μM) | FUDR (μM) | 5-FU (μM) | TDX (μM) |
| C/HT1080 | 100 | 320 | <0.1 | 1.0 | 3.6 |
| TSL/HT1080 | 409 | 196 | 2.2 | 1.7 | 24 |
| TSL/HT1080 | 702 | 0.8 | 3.1 | 3.5 | 153 |

A cDNA encoding rHuTS was subcloned into ventor pEGFP-C3, in-frame with GFP. The construct was transfected into HT1080 cells and selected with G418 (750 ug/ml) in order to obtain clones that stably express fusion rHuTS. Individual cells were cloned based upon high or low fluorescence expression as described in Methods. *TS levels were determined by using Western blot analysis, the quantified expression levels were expressed as values relative to that of cell strain CCD18co.

TABLE 6

Tomudex Inhibits NB1011 Mediated Cytotoxicity

| [Tomudex] (nM) | 0 nM | 1 mM | 10 nM | 100 nM | 1000 nM |
|---|---|---|---|---|---|
| NB1011 IC$_{50}$ ($\mu$M) | 5.7 | 25.5 | 87.7 | 140.3 | 103.0 |
| Fold Protection | 1 | 4.5 x | 15.4 x | 24.6 x | 18.1 x |

The Tomudex rescue assay (alamar blue) was done with TDX-resistant MCF7 breast tumor cells as described in Methods. "Fold Protection" was calculated as the ratio of IC$_{50}$ with and without added TDX.

TABLE 7

Impact of Folate Inhibitors

| Inhibitor | BVdUMP, with THF | BVdUMP, w/o THF | dUMP, with THF |
|---|---|---|---|
| None | 100% | 138% | 100% |
| MTX | 10% | 24% | 31% |
| LV | 17% | 97% | 77% |
| TDX | 0% | 25% | 18% |

Cell-free assays using rHuTS, the appropriate substrate and other components were combined as described in Methods. MTX (140 $\mu$M), LV (140 $\mu$M) or TDX (5 $\mu$M) were added to evaluate their inhibitory activity. Utilization of substrate (either BVdUMP or THF) was employed as a measure of reaction rate. The numbers indicate remaining activity.

TABLE 8

NB1011 activity is more associated with TS protein than with tritium release

| Cell Line | Drug Selection | TS Protein | Tritium Release | NB1011-IC$_{50}$ |
|---|---|---|---|---|
| H630 | None | 288 | 3206 | 414 |
| Colon cancer | 5FU | 2350 | 1840 | 65 |
|  | TDX | 671 | 3980 | 2.3 |
| RKO | None | 142 | 4920 | 136 |
| Colon cancer | TDX | 279 | 1625 | 28 |
| MCF7 | None | 178 | 5185 | 327 |
| Breast cancer | TDX | 1980 | 875 | 2.8 |
| N1S1 | None | 197 | 12,565 | 494 |
|  | 5FU | 1241 | ND | 204 |

TABLE 9

MDF7 TDX cells selected for resistance to NB1011 are more sensitive to 5-Fluorouracil and Tomudex

| | IC$_{50}$ (micromolar)* | | | Relative TS Protein Level |
|---|---|---|---|---|
| | 5-FU | Tomudex | NB1011 | |
| MCF7 | 10- | .026- | 291- | 1 X- |
| MCF7 TDX | 32 | >10 | 2 | 11 X |
| MCF7 TDX/1011 | 2 | .041 | 240 | 4 X |

*as determined by the alamar blue assay described in Materials and Methods
TDX = Tomudex; 1011 = NB1011

What is claimed is:

1. A method for screening for therapeutic agents for administration in combination with (E)-5-(2-bromovinyl)-2'-deoxy-5'-uridyl phenyl L-alaninylphosphoramidate or (E)-5-(2-bromovinyl)-2'-deoxy-5'-uridyl phenyl L-alaninyl monophosphate, comprising contacting the candidate therapeutic agent and (E)-5-(2-bromovinyl)-2'-deoxy-5'-uridyl phenyl L-alaninylphosphoramidate or (E)-5-(2-bromovinyl)-2'-deoxy-5'-uridyl phenyl monophosphate with a cancer cell selected from the group consisting of a breast cancer cell, a non-small cell lung cancer cell, a rectal cancer cell, a head and neck cancer cell, a stomach cancer cell, a pancreatic cancer cell, a colon cancer cell, a liver cancer cell, a gastric cancer cell, a skin cancer cell, a bone cancer cell, a bone marrow cancer cell, a testicular cancer cell, a brain cancer cell, a lung cancer cell, a prostate cancer cell and an ovarian cancer cell, and wherein said cell endogenously overexpresses, intracellular thymidylate synthase enzyme and assaying for cell death.

2. The method of claim 1, further comprising contacting a normal cell with the candidate therapeutic agent and (E)-5-(2-bromovinyl)-2'-deoxy-5'-uridyl phenyl L-alaninylphosphoramidate or (E)-5-(2-bromovinyl)-2'-deoxy-5'-uridyl phenyl monophosphate and assaying for cell death.

3. The method of claim 1, wherein the candidate therapeutic agent is contacted with the cell subsequent to contacting the cell with (E)-5-(2-bromovinyl)-2'-deoxy-5'-uridyl phenyl L-alaninylphosphoramidate.

4. The method of claim 1, wherein the cell is resistant to (E)-5-(2-bromovinyl)-2'-deoxy-5'-uridyl phenyl L-alaninylphosphoramidate.

* * * * *